US009745340B2

(12) United States Patent
Jonasson et al.

(10) Patent No.: US 9,745,340 B2
(45) Date of Patent: Aug. 29, 2017

(54) METHOD FOR THE SEPARATION OF PROTEINS CONTAINING AN ALBUMIN-BINDING

(71) Applicant: AFFIBODY AB, Solna (SE)

(72) Inventors: Per Jonasson, Stockholm (SE); Pär Eklund, Stockholm (SE)

(73) Assignee: AFFIBODY AB, Solna (SE)

( * ) Notice: Subject to any disclaimer, the term of this patent is extended or adjusted under 35 U.S.C. 154(b) by 0 days.

(21) Appl. No.: 14/436,150

(22) PCT Filed: Oct. 25, 2013

(86) PCT No.: PCT/EP2013/072365
§ 371 (c)(1),
(2) Date: Apr. 16, 2015

(87) PCT Pub. No.: WO2014/064238
PCT Pub. Date: May 1, 2014

(65) Prior Publication Data
US 2015/0274771 A1    Oct. 1, 2015

Related U.S. Application Data

(60) Provisional application No. 61/718,246, filed on Oct. 25, 2012.

(30) Foreign Application Priority Data

Oct. 25, 2012   (EP) ..................................... 12189948

(51) Int. Cl.
| | | |
|---|---|---|
| *C07K 1/22* | (2006.01) | |
| *C07K 14/00* | (2006.01) | |
| *C07K 1/14* | (2006.01) | |
| *C07K 1/16* | (2006.01) | |
| *C07K 14/315* | (2006.01) | |
| *C07K 14/31* | (2006.01) | |

(52) U.S. Cl.
CPC ................ *C07K 1/22* (2013.01); *C07K 14/00* (2013.01); *C07K 14/31* (2013.01); *C07K 14/315* (2013.01); *C07K 2319/70* (2013.01)

(58) Field of Classification Search
None
See application file for complete search history.

(56) References Cited

FOREIGN PATENT DOCUMENTS

| EP | 2077272 A1 | 7/2009 |
|---|---|---|
| WO | 9101743 A1 | 2/1991 |
| WO | 0145746 A2 | 6/2001 |
| WO | 2009016043 A2 | 2/2009 |
| WO | 2009019117 A1 | 2/2009 |
| WO | 2009077175 A1 | 6/2009 |
| WO | 2010056550 A1 | 5/2010 |
| WO | 2011056124 A1 | 5/2011 |
| WO | 2012004384 A2 | 1/2012 |
| WO | 2013126006 A1 | 8/2013 |

OTHER PUBLICATIONS

Ahmad et al., "Novel High-Affinity Binders of Human Interferon Gamma Derived from Albumin-Binding Domain of Protein G", Proteins; 80; 2011; pp. 774-789.
Alm et al., "A Small Bispecific Protein Selected for Orthogonal Affinity Purification", Biotechnol. J. 5; (2010); 605-617.
Braisted et al., "Minimizing a Binding Domain From Protein A", Proc. Natl. Acad. Sci. USA; 93; (1996); pp. 5688-5692.
Cramer et al., "Crystal Structure of a Bacterial Albumin-Binding Domain at 1.4 Å Resolution", FEBS Letters; 581; (2007); pp. 3178-3182.
de Chateau et al., "Protein PAB, a Mosaic Albumin-Binding Bacterial Protein Representing the First Contemporary Example of Module Shuffling", The Journal of Biological Chemistry; vol. 269; No. 16; Issue of Apr. 22, 1994; pp. 12147-12151.
He et al., "An Artificially Evolved Albumin Binding Module Facilitates Chemical Shift Epitope Mapping of GA Domain Interactions with Phylogenetically Diverse Albumins", Protein Science; 16; (2007); pp. 1490-1494.
International Preliminary Report on Patentability and Written Opinion of the International Searching Authority for International Patent App No. PCT/EP2013/072365; International Filing Date: Oct. 25, 2013; Date of Mailing: May 7, 2015; 8 Pages.
International Search Report of the International Searching Authority for International Patent Application No. PCT/EP2013/072359; International Filing Date: Oct. 25, 2013; Date of Mailing: Feb. 26, 2014; 7 Pages.
Lejon et al., "Crystal Structure and Biological Implications of a Bacterial Albumin Binding Module in Complex with Human Serum Albumin"; The Journal of Biological Chemistry; 279; (2004); pp. 42924-42928.
Lofblom et al., "Affibody Molecules: Engineered Proteins for Therapeutic, Diagnostic and Biotechnological Applications", FEBS Letters; 584; (2010); pp. 2670-2680.
Nilvebrant et al., "Engineering Bispecificity Into a Single Albumin-Binding Domain", vol. 6; Issue 10; (2011); pp. e25791-e25791.
Nord et al., "Binding Proteins Selected from Combinatiorial Libraries of an α-helical Bacterial receptor Domain", Nature Biotechnology; vol. 15; (1997); pp. 772-777.
Nygren "Alternative Binding Proteins: Affibody Binding Proteins Developed From a Small Three-Helix Bundle Scaffold", FEBS Journal; 275; (2008); pp. 2668-2676.

(Continued)

*Primary Examiner* — Marcela M Cordero Garcia
*Assistant Examiner* — Catherine Mader
(74) *Attorney, Agent, or Firm* — Cantor Colburn LLP

(57) ABSTRACT

The disclosure provides a method of separation of at least one ABD-containing molecule present in a liquid from other constituents in the liquid, comprising a step of affinity separation, in which step is used, as affinity ligand, an ABD binding polypeptide comprising an ABD binding motif BM, which motif consists of an amino acid sequence selected from (SEQ ID NO: 166)
$EX_2X_3X_4AX_6X_7EIX_{10}X_{11}LPNLX_{16}X_{17}X_{18}QX_{20}X_{21}AFIX_{25}X_{26}LX_{28}D$ and amino acid sequences with at least 89% identity thereto.

14 Claims, 26 Drawing Sheets

(56) References Cited

OTHER PUBLICATIONS

Tashiro et al., "High-Resolution Solution NMR Structure of the Z Domain of Staphylococcal Protein A", J. Mol. Biol.; 272; (1997); pp. 573-590.
Wahlberg et al., "An Affibody in Complex With a Target Protein: Structure and Coupled Folding", PNAS; vol. 100; No. 6; Mar. 18, 2003; pp. 3185-3190.
International Search Report of the International Searching Authority for International Patent Application No. PCT/EP2013/072365; International Filing Date: Oct. 25, 2013; Date of Mailing: Jan. 17, 2014; 3 Pages.
Nord et al. "Binding Proteins Selected from Combinatorial Libraries of an a-helical Bacterial Receptor Domain" Nature Biotechnology; vol. 15, Aug. 1997; pp. 772-777.
Nord et al., "A Combinatorial Library of an Alpha-helical Bacterial Receptor Domain" Protein Engineering, Oxford University Press, vol. 8, No. 6, pp. 601-608, XP 000615264 (1995).
GenBank Entry AAA61965.1; PPmABPXM precursor [*Staphylococcus carnosus*]; Feb. 7, 1995.
Johansson et al.; "Structure, Specificity, and Mode of Interaction for Bacterial Albumin-binding Modules"; J. Bio. Chem., vol. 277, No. 10; 2002; pp. 8114-8120.

| Designation | Amino acid sequence | SEQ ID NO |
|---|---|---|
| BM06677 | ELKVAFKEINTLPNLTHQRIAFIIKLDD | 1 |
| BM06638 | ELVNAFSEIKALPNLTLHQRLAFIVKLDD | 2 |
| BM06608 | ELHHAFREIKFLPNLTFHQRLAFIVKLDD | 3 |
| BM06650 | EFKLALQEIHYLPNLTLDQRLAFILKLDD | 4 |
| BM06678 | ELRWALNEIRRLPNLTFKQHIAFIVKLDD | 5 |
| BM06620 | EFRAALLEIKLLPNLTFIQRLAFIVKLDD | 6 |
| BM06695 | EFTIALREIHALPNLTLHQRLAFIIKLDD | 7 |
| BM06681 | ELRKAFHEIQILPNLTLSQRLAFIVKLDD | 8 |
| BM06655 | EFKDALDEIKDLPNLTSMQRIAFIVKLDD | 9 |
| BM06602 | ELTTAFAEIQKLPNLTIFEQKIAFIIKLDD | 10 |
| BM06670 | EFREAIIEIRRLPNLTLHQRLAFIMKLDD | 11 |
| BM06668 | EIKTAFAEIRVLPNLTFAQRLAFIIKLDD | 12 |
| BM06690 | ERRYAFREIRLLPNLTFSQRIAFIVKLDD | 13 |
| BM06667 | ELKAAFREINDLPNLTHTQRIAFILKLDD | 14 |
| BM06641 | ELKMAFQEIRYLPNLTRLQRIAFIVKLDD | 15 |
| BM06686 | EWKKALREIHYLPNLTLTQRLAFIVKLDD | 16 |
| BM06664 | EFEKALVEIKTLPNLTAIQRIAFIVKLDD | 17 |
| BM06583 | EFIFALSEIKVLPNLTHVQKIAFIVKLDD | 18 |
| BM06687 | EFKYAIQEIKDLPNLTSGQRIAFIVKLDD | 19 |
| BM06700 | ELNQALWEIRQLPNLTFNQRVAFIVKLDD | 20 |
| BM06661 | ELQGALTEIKNLPNLTGHQRIAFIVKLDD | 21 |
| BM06669 | ELADALYEIKNLPNLTHEQHIAFIVKLDD | 22 |
| BM06676 | ELGVALKEIGQLPNLTHTQRIAFIIKLDD | 23 |
| BM06680 | ELSIALNEIKGLPNLTSLQKIAFIVKLDD | 24 |
| BM06531 | EIRSAYKEINVLPNLTFSQKIAFIYKLED | 25 |
| BM06665 | ELSSALLEISHLPNLTHQQRIAFIVKLDD | 26 |
| BM06683 | ELVHAFGEIRYLPNLTHSQRIAFIIKLDD | 27 |
| BM06698 | ELHNAFSEIKQLPNLTTQQRIAFIIKLDD | 28 |
| BM06692 | EGVNAFNEIKGLPNLTFHQKIAFIVKLDD | 29 |

FIGURE 1A

| Designation | Amino acid sequence | SEQ ID NO |
|---|---|---|
| BM06660 | ELKYALMEIRYLPNLTHRQKIAFILKLDD | 30 |
| BM06645 | ELRWAVSEIRHLPNLTFHQRIAFIVKLDD | 31 |
| BM06508 | ELQRAFAEIQSLPNLTLNQHIAFIYKLED | 32 |
| BM06649 | ELKAAFREIRTLPNLTFGQRTAFIVKLDD | 33 |
| BM06666 | ELTTAMKEIQALPNLTHQQRIAFIVKLDD | 34 |
| BM06549 | EDMRAFHEINKLPNLTLAQRVAFIYKLED | 35 |
| BM06552 | ELNAAFTEISSLPNLTLDQRLAFIFKLDD | 36 |
| BM06672 | ELRWALNEIHILPNLTLEQKVAFIVKLDD | 37 |
| BM06484 | ELKNAFTEIKNLPNLTTNQTLAFIVKLDD | 38 |
| BM06652 | ELSLAFVEIHKLPNLTHHQRLAFIVKLDD | 39 |
| BM06480 | ELQWAFNEIHNLPNLTYQRIAFIVKLDD | 40 |
| BM06512 | EEQTAMQEINSLPNLTLEQRIAFIFKLED | 41 |
| BM06648 | ELGWAFREIRNLPNLTHYQRIAFIMKLDD | 42 |
| BM06691 | ENLWAFNEIKGLPNLTHDQRIAFIVKLDD | 43 |
| BM06501 | ELSFAFSEINVLPNLTFHQKIAFIYKLED | 44 |
| BM06544 | EFRGAIAEIRDLPNLTLEQKYAFIFKLED | 45 |
| BM06487 | EEENAYKEIGSLPNLTLAQKVAFILKLED | 46 |
| BM06688 | ELRQALQEIHILPNLTHSQRVAFIVKLDD | 47 |
| BM06503 | ENHAAFQEILSLPNLTLNQRLAFITKLDD | 48 |
| BM06491 | ETNYAFKEIDLLPNLTLMQKLAFIVKLDD | 49 |
| BM06675 | EISLAFKEIKALPNLTGQQRFAFILKLDD | 50 |
| BM06584 | ELSKALTEIRMLPNLTFRQRIAFIIKLDD | 51 |
| BM06540 | ELDMAYTEIGLLPNLTFSQLLAFIIKLDD | 52 |
| P06677 | KELKVAFKEINTLPNLTHQQRIAFIIKLDDDPSQSSELLAEAKKLNDAQ | 53 |
| P06638 | KELVNAFSEIKALPNLTLHQRLAFTVKLDDDPSQSSELLAEAKKLNDAQ | 54 |
| P06608 | KELHHAFREIKFLPNLTFHQRLAFTVKLDDDPSQSSELLAEAKKLNDAQ | 55 |
| P06650 | KEFKLALQEIHYLPNLTLDQRLAFILKLDDDPSQSSELLAEAKKLNDAQ | 56 |
| P06678 | KELRWALNEIRRLPNLTFKQHIAFIVKLDDDPSQSSELLAEAKKLNDAQ | 57 |
| P06620 | KEFRAALLEIKLLPNLTFIQRLAFIVKLDDDPSQSSELLAEAKKLNDAQ | 58 |

FIGURE 1B

| Designation | Amino acid sequence | SEQ ID NO |
|---|---|---|
| P06695 | KEFTIALREIHALPNLITHQRLAFIIKLDDDPSQSSELLAEAKKLNDAQ | 59 |
| P06681 | KELRKAFHEIQILPNLTLSQRLAFIVKLDDDPSQSSELLAEAKKLNDAQ | 60 |
| P06655 | KEFKDALDEIKDLPNLTSMQRIAFIVKLDDDPSQSSELLAEAKKLNDAQ | 61 |
| P06602 | KELTTAFAEIQKLPNLTFEQKIAFIIKLDDDPSQSSELLAEAKKLNDAQ | 62 |
| P06670 | KEFREAIIEIRRLPNLTLHQRLAFIMKLDDDPSQSSELLAEAKKLNDAQ | 63 |
| P06668 | KEIKTAFAEIRVLPNLTFAQRLAFIIKLDDDPSQSSELLAEAKKLNDAQ | 64 |
| P06690 | KERRYAFREIRLLPNLTFSQRIAFIVKLDDDPSQSSELLAEAKKLNDAQ | 65 |
| P06667 | KELKAAFREINDLPNLTHTQRIAFILKLDDDPSQSSELLAEAKKLNDAQ | 66 |
| P06641 | KELKMAFQEIRYLPNLTRLQRIAFIVKLDDDPSQSSELLAEAKKLNDAQ | 67 |
| P06686 | KEWKKALREIHYLPNLTLTQRLAFIVKLDDDPSQSSELLAEAKKLNDAQ | 68 |
| P06664 | KEFEKALVEIKTLPNLITAIQRIAFIVKLDDDPSQSSELLAEAKKLNDAQ | 69 |
| P06583 | KEFIFALSEIKVLPNLTHVQKIAFIVKLDDDPSQSSELLAEAKKLNDAQ | 70 |
| P06687 | KEFKYAIQEIKDLPNLTSGQRIAFIVKLDDDPSQSSELLAEAKKLNDAQ | 71 |
| P06700 | KELNQALWEIRQLPNLTFNQRVAFIVKLDDDPSQSSELLAEAKKLNDAQ | 72 |
| P06661 | KELQGALTEIKNLPNLIGHQRIAFIVKLDDDPSQSSELLAEAKKLNDAQ | 73 |
| P06669 | KELADALYEIKNLPNLTHEQHIAFIVKLDDDPSQSSELLAEAKKLNDAQ | 74 |
| P06676 | KELGVALKEIGQLPNLTHTQRIAFIVKLDDDPSQSSELLAEAKKLNDAQ | 75 |
| P06680 | KELSIALNEIKGLPNLTSLQKIAFIVKLDDDPSQSSELLAEAKKLNDAQ | 76 |
| P06531 | KEIRSAYKEINVLPNLTFSQKIAFIYKLEDDPSQSSELLAEAKKLNDAQ | 77 |
| P06665 | KELSSALLEISHLPNLTHQQRIAFIIKLDDDPSQSSELLAEAKKLNDAQ | 78 |
| P06683 | KELVHAFGEIRYLPNLTHSQRIAFIVKLDDDPSQSSELLAEAKKLNDAQ | 79 |
| P06698 | KELHNAFSEIKQLPNLTTQQRIAFIVKLDDDPSQSSELLAEAKKLNDAQ | 80 |
| P06692 | KEGVNAFNEIKGLPNLTFHQKIAFIVKLDDDPSQSSELLAEAKKLNDAQ | 81 |
| P06660 | KELRKYALMEIRYLPNLTHRQKIAFIVKLDDDPSQSSELLAEAKKLNDAQ | 82 |
| P06645 | KELRWAVSEIRHLPNLTFHQRIAFIVKLDDDPSQSSELLAEAKKLNDAQ | 83 |
| P06508 | KELQRAFAEIQSLPNLTLNQHIAFIVKLDDDPSQSSELLAEAKKLNDAQ | 84 |
| P06649 | KELKAAFREIRTLPNLTFGQRTAFIVKLDDDPSQSSELLAEAKKLNDAQ | 85 |
| P06666 | KELTTAMKEIQAIPNLTHQQRIAFIVKLDDDPSQSSELLAEAKKLNDAQ | 86 |
| P06549 | KEDMRAFHEINKLPNLTLAQRVAFIYKLEDDPSQSSELLAEAKKLNDAQ | 87 |

FIGURE 1C

| Designation | Amino acid sequence | SEQ ID NO |
|---|---|---|
| P06552 | KELNAAFTEISSLPNLTLDQRLAFIFKLDDDPSQSSELLAEAKKLNDAQ | 88 |
| P06672 | KELRWALNEIHILPNLTLEQKVAFIVKLDDDPSQSSELLAEAKKLNDAQ | 89 |
| P06484 | KELKNAFIEIKNLPNLTTNQTLAFIVKLDDDPSQSSELLAEAKKLNDAQ | 90 |
| P06652 | KELSLAFVEIHKLPNLTHHQRLAFIVKLDDDPSQSSELLAEAKKLNDAQ | 91 |
| P06480 | KELQWAFNEIHNLPNLTYVQRIAFIVKLDDDPSQSSELLAEAKKLNDAQ | 92 |
| P06512 | KEEQTAMQEINSLPNLTLEQRIAFIFKLEDDPSQSSELLAEAKKLNDAQ | 93 |
| P06648 | KELGWAFREIRNLPNLTHYQRIAFIMKLDDDPSQSSELLAEAKKLNDAQ | 94 |
| P06691 | KENLWAFNEIKGLPNLTHDQRIAFIVKLDDDPSQSSELLAEAKKLNDAQ | 95 |
| P06501 | KELSFAFSEINVLPNLTFHQKIAFIYKLEDDPSQSSELLAEAKKLNDAQ | 96 |
| P06544 | KEFRGAIAEIRDLPNLTIEQKYAFIFKLEDDPSQSSELLAEAKKLNDAQ | 97 |
| P06487 | KEEENAYKEIGSLPNLTLAQKVAFILKLEDDPSQSSELLAEAKKLNDAQ | 98 |
| P06688 | KELRQALQEIHILPNLTHSQRVAFIVKLDDDPSQSSELLAEAKKLNDAQ | 99 |
| P06503 | KENHAAFQEILSLPNLTNQRLAFITKLDDDPSQSSELLAEAKKLNDAQ | 100 |
| P06491 | KETNYAFKEIDLLPNLTMQKLAFIVKLDDDPSQSSELLAEAKKLNDAQ | 101 |
| P06675 | KEISLAFKEIKALPNLTGQQRFAFIAFILKLDDDPSQSSELLAEAKKLNDAQ | 102 |
| P06584 | KELSKALTEIRMLPNLTFRQRIAFIIKLDDDPSQSSELLAEAKKLNDAQ | 103 |
| P06540 | KELDMAYTEIGLLPNLTFSQLLAFIIKLDDDPSQSSELLAEAKKLNDAQ | 104 |
| Z06677 | VDAKYAKELKVAFKEINTLPNLTHQQRIAFIIKLDDDPSQSSELLAEAKKLNDAQAPK | 105 |
| Z06638 | VDAKYAKELVNAFSEIKALPNLTLHQRLAFIVKLDDDPSQSSELLAEAKKLNDAQAPK | 106 |
| Z06608 | VDAKYAKELHHAFREIKFLPNLTFHQRLAFIVKLDDDPSQSSELLAEAKKLNDAQAPK | 107 |
| Z06650 | VDAKYAKEFKLALQEIHYLPNLTLDQRLAFILKLDDDPSQSSELLAEAKKLNDAQAPK | 108 |
| Z06678 | VDAKYAKELRWALNEIRRLPNLTFKQHIAFIVKLDDDPSQSSELLAEAKKLNDAQAPK | 109 |
| Z06620 | VDAKYAKEFRAALLEIKLLPNLTFIQRLAFIVKLDDDPSQSSELLAEAKKLNDAQAPK | 110 |
| Z06695 | VDAKYAKEFTIALREIHALPNLTLHQRLAFIIKLDDDPSQSSELLAEAKKLNDAQAPK | 111 |
| Z06681 | VDAKYAKELRKAFHEIQILPNLTLSQRLAFIVKLDDDPSQSSELLAEAKKLNDAQAPK | 112 |
| Z06655 | VDAKYAKEFKDALDEIKDLPNLTSMQRIAFIVKLDDDPSQSSELLAEAKKLNDAQAPK | 113 |
| Z06602 | VDAKYAKELTTAFAEIQKLPNLTFEQKIAFITFAFEIRVLPNLTFAQRLAFIIKLDDDPSQSSELLAEAKKLNDAQAPK | 114 |
| Z06670 | VDAKYAKEFREAIIEIRRLPNLTLHQRLAFIMKLDDDPSQSSELLAEAKKLNDAQAPK | 115 |
| Z06668 | VDAKYAKEIKTAFAEIRVLPNLTFAQRLAFIIKLDDDPSQSSELLAEAKKLNDAQAPK | 116 |

FIGURE 1D

| Designation | Amino acid sequence | SEQ ID NO |
|---|---|---|
| Z06690 | VDAKYAKERRYAFREIRLLPNLTFSQRIAFIVKLDDDPSQSSELLAEAKKLNDAQAPK | 117 |
| Z06667 | VDAKYAKELKAAFREINDLPNLTHTQRIAFILKLDDDPSQSSELLAEAKKLNDAQAPK | 118 |
| Z06641 | VDAKYAKELKMAFQEIRYLPNLTRLQRIAFTVKLDDDPSQSSELLAEAKKLNDAQAPK | 119 |
| Z06686 | VDAKYAKEWKKALREIHYLPNLTLTQRLAFIVKLDDDPSQSSELLAEAKKLNDAQAPK | 120 |
| Z06664 | VDAKYAKEFEKALVEIKTLPNLTAIQRIAFIVKLDDDPSQSSELLAEAKKLNDAQAPK | 121 |
| Z06583 | VDAKYAKEFIFALSEIKVLPNLTHVQKIAFIVKLDDDPSQSSELLAEAKKLNDAQAPK | 122 |
| Z06687 | VDAKYAKEFKYAIQEIKDLPNLTSGQRIAFIVKLDDDPSQSSELLAEAKKLNDAQAPK | 123 |
| Z06700 | VDAKYAKELNQALMEIRQLPNLTFNQRVAFIVKLDDDPSQSSELLAEAKKLNDAQAPK | 124 |
| Z06661 | VDAKYAKELQGALTEIKNLPNLTGHQRIAFIVKLDDDPSQSSELLAEAKKLNDAQAPK | 125 |
| Z06669 | VDAKYAKELADALYEIKNLPNLTHEQHIAFTVKLDDDPSQSSELLAEAKKLNDAQAPK | 126 |
| Z06676 | VDAKYAKELGVALKEIGQLPNLTHTQRIAFIVKLDDDPSQSSELLAEAKKLNDAQAPK | 127 |
| Z06680 | VDAKYAKELSIALNEIKGLPNLTSLQKIAFIIKLDDDPSQSSELLAEAKKLNDAQAPK | 128 |
| Z06531 | VDAKYAKEIRSAYKEINVLPNLTFSQKIAFIVKLDDDPSQSSELLAEAKKLNDAQAPK | 129 |
| Z06665 | VDAKYAKELSSALLEISHLPNLTHQQRIAFIVKLDDDPSQSSELLAEAKKLNDAQAPK | 130 |
| Z06683 | VDAKYAKELVHAFGEIRYLPNLTHSQRIAFIIKLDDDPSQSSELLAEAKKLNDAQAPK | 131 |
| Z06698 | VDAKYAKELHNAFSEIKQLPNLTTQQRIAFIVKLDDDPSQSSELLAEAKKLNDAQAPK | 132 |
| Z06692 | VDAKYAKEGVNAFNEIKGLPNLTFHQKIAFIVKLDDDPSQSSELLAEAKKLNDAQAPK | 133 |
| Z06660 | VDAKYAKELKYALMEIRYLPNLTHRQKIAFIVKLDDDPSQSSELLAEAKKLNDAQAPK | 134 |
| Z06645 | VDAKYAKELRWAVSEIRHLPNLTFHQRIAFTVKLDDDPSQSSELLAEAKKLNDAQAPK | 135 |
| Z06508 | VDAKYAKELQRAFAEIQSLPNLTRTLPNLTFGQRTAFIVKLDDDPSQSSELLAEAKKLNDAQAPK | 136 |
| Z06649 | VDAKYAKELKAAFREIRTLPNLTFGQRTAFIVKLDDDPSQSSELLAEAKKLNDAQAPK | 137 |
| Z06666 | VDAKYAKELTTAMKEIQALPNLTHQQRIAFTVKLDDDPSQSSELLAEAKKLNDAQAPK | 138 |
| Z06549 | VDAKYAKEDMRAFHEINKLPNLTLAQRVAFIYKLEDDPSQSSELLAEAKKLNDAQAPK | 139 |
| Z06552 | VDAKYAKELNAAFTEISSLPNLTLDQRLAFIFKLDDDPSQSSELLAEAKKLNDAQAPK | 140 |
| Z06672 | VDAKYAKELRWALNEIHILPNLTLEQKVAFTVKLDDDPSQSSELLAEAKKLNDAQAPK | 141 |
| Z06484 | VDAKYAKELKNAFIEIKNLPNLTTNQTLAFIVKLDDDPSQSSELLAEAKKLNDAQAPK | 142 |
| Z06652 | VDAKYAKELSLAFVEIHKLPNLTHHQRIAFIVKLDDDPSQSSELLAEAKKLNDAQAPK | 143 |
| Z06480 | VDAKYAKELQWAFNEIHNLPNLTYVQRIAFIVKLDDDPSQSSELLAEAKKLNDAQAPK | 144 |
| Z06512 | VDAKYAKEEQTAMQEINSLPNLTLEQRIAFIFKLEDDPSQSSELLAEAKKLNDAQAPK | 145 |

FIGURE 1E

| Designation | Amino acid sequence | SEQ ID NO |
|---|---|---|
| Z06648 | VDAKYAKELGWAFREIRNLPNLTHYQRIAFIMKLDDDPSQSSELLAEAKKLNDAQAPK | 146 |
| Z06691 | VDAKYAKENLWAFNEIKGLPNLTHDQRIAFIVKLDDDPSQSSELLAEAKKLNDAQAPK | 147 |
| Z06501 | VDAKYAKELSFAFSEINVLPNLTFHQKIAFIYKLEDDPSQSSELLAEAKKLNDAQAPK | 148 |
| Z06544 | VDAKYAKEFRGAIAEIRDLPNLTLEQKYAFIFKLEDDPSQSSELLAEAKKLNDAQAPK | 149 |
| Z06487 | VDAKYAKEENAYKEIGSLPNLTLAQKVAFILKLEDDPSQSSELLAEAKKLNDAQAPK | 150 |
| Z06688 | VDAKYAKELRQALQEIHILPNLTHSQRVAFIVKLDDDPSQSSELLAEAKKLNDAQAPK | 151 |
| Z06503 | VDAKYAKENHAAFQEILSLPNLTLNQRLAFITKLDDDPSQSSELLAEAKKLNDAQAPK | 152 |
| Z06491 | VDAKYAKETNYAFKEIDLLPNLTIMQKLAFIVKLDDDPSQSSELLAEAKKLNDAQAPK | 153 |
| Z06675 | VDAKYAKEISLAFKEIKALPNLTGQQREAFILKLDDDPSQSSELLAEAKKLNDAQAPK | 154 |
| Z06584 | VDAKYAKELSKALTEIRMLPNLTFRQRIAFIIKLDDDPSQSSELLAEAKKLNDAQAPK | 155 |
| Z06540 | VDAKYAKELDMAYTEIGLLPNLTFSQLLAFIIKLDDDPSQSSELLAEAKKLNDAQAPK | 156 |
| ABD001 | LAEAKVLANRELDKYGVSDYYKNLINNAKTVEGVKALIDEILAALP | 157 |
| C-ABD001 | CLAEAKVLANRELDKYGVSDYYKNLINNAKTVEGVKALIDEILAALP | 158 |
| ABD035 | LAEAKVLANRELDKYGVSDFYKRLINKAKTVEGVEALKLHILAALP | 159 |
| PP013 | LAEAKEAANAELDSYGVSDFYKRLIDKAKTVEGVEALKDAILAALP | 160 |
| PEP07986 | GSLAEAKEAANAELDSYGVSDFYKRLIDKAKTVEGVEALKDAILAALP | 161 |
| PEP07911 | GLASAKEAANAELDCYGVSDFYKRLIDKAKTVEGVEALKDAILAALP | 162 |

FIGURE 1F

SEQUENCE LISTING

```
<160> NUMBER OF SEQ ID NOS: 187

<210> SEQ ID NO 1
<211> LENGTH: 29
<212> TYPE: PRT
<213> ORGANISM: Artificial sequence
<220> FEATURE:
<223> OTHER INFORMATION: Engineered ABD binding polypeptide

<400> SEQUENCE: 1

Glu Leu Lys Val Ala Phe Lys Glu Ile Asn Thr Leu Pro Asn Leu Thr
1               5                   10                  15

His Gln Gln Arg Ile Ala Phe Ile Ile Lys Leu Asp Asp
            20                  25

<210> SEQ ID NO 2
<211> LENGTH: 29
<212> TYPE: PRT
<213> ORGANISM: Artificial sequence
<220> FEATURE:
<223> OTHER INFORMATION: Engineered ABD binding polypeptide

<400> SEQUENCE: 2

Glu Leu Val Asn Ala Phe Ser Glu Ile Lys Ala Leu Pro Asn Leu Thr
1               5                   10                  15

Leu His Gln Arg Leu Ala Phe Ile Val Lys Leu Asp Asp
            20                  25

<210> SEQ ID NO 3
<211> LENGTH: 29
<212> TYPE: PRT
<213> ORGANISM: Artificial sequence
<220> FEATURE:
<223> OTHER INFORMATION: Engineered ABD binding polypeptide

<400> SEQUENCE: 3

Glu Leu His His Ala Phe Arg Glu Ile Lys Phe Leu Pro Asn Leu Thr
1               5                   10                  15
```

Phe His Gln Arg Leu Ala Phe Ile Val Lys Leu Asp Asp
            20                  25

<210> SEQ ID NO 4
<211> LENGTH: 29
<212> TYPE: PRT
<213> ORGANISM: Artificial sequence
<220> FEATURE:
<223> OTHER INFORMATION: Engineered ABD binding polypeptide

<400> SEQUENCE: 4

Glu Phe Lys Leu Ala Leu Gln Glu Ile His Tyr Leu Pro Asn Leu Thr
1               5                   10                  15

Leu Asp Gln Arg Leu Ala Phe Ile Leu Lys Leu Asp Asp
            20                  25

<210> SEQ ID NO 5
<211> LENGTH: 29
<212> TYPE: PRT
<213> ORGANISM: Artificial sequence
<220> FEATURE:
<223> OTHER INFORMATION: Engineered ABD binding polypeptide

<400> SEQUENCE: 5

Glu Leu Arg Trp Ala Leu Asn Glu Ile Arg Arg Leu Pro Asn Leu Thr
1               5                   10                  15

Phe Lys Gln His Ile Ala Phe Ile Val Lys Leu Asp Asp
            20                  25

<210> SEQ ID NO 6
<211> LENGTH: 29
<212> TYPE: PRT
<213> ORGANISM: Artificial sequence
<220> FEATURE:
<223> OTHER INFORMATION: Engineered ABD binding polypeptide

<400> SEQUENCE: 6

Glu Phe Arg Ala Ala Leu Leu Glu Ile Lys Leu Leu Pro Asn Leu Thr
1               5                   10                  15

Phe Ile Gln Arg Leu Ala Phe Ile Val Lys Leu Asp Asp
            20                  25

<210> SEQ ID NO 7
<211> LENGTH: 29
<212> TYPE: PRT
<213> ORGANISM: Artificial sequence
<220> FEATURE:
<223> OTHER INFORMATION: Engineered ABD binding polypeptide

<400> SEQUENCE: 7

Glu Phe Thr Ile Ala Leu Arg Glu Ile His Ala Leu Pro Asn Leu Thr
1               5                   10                  15

Leu His Gln Arg Leu Ala Phe Ile Ile Lys Leu Asp Asp
            20                  25

<210> SEQ ID NO 8
<211> LENGTH: 29
<212> TYPE: PRT
<213> ORGANISM: Artificial sequence
<220> FEATURE:
<223> OTHER INFORMATION: Engineered ABD binding polypeptide

<400> SEQUENCE: 8

Glu Leu Arg Lys Ala Phe His Glu Ile Gln Ile Leu Pro Asn Leu Thr
1               5                   10                  15

```
Leu Ser Gln Arg Leu Ala Phe Ile Val Lys Leu Asp Asp
            20                  25
```

```
<210> SEQ ID NO 9
<211> LENGTH: 29
<212> TYPE: PRT
<213> ORGANISM: Artificial sequence
<220> FEATURE:
<223> OTHER INFORMATION: Engineered ABD binding polypeptide

<400> SEQUENCE: 9

Glu Phe Lys Asp Ala Leu Asp Glu Ile Lys Asp Leu Pro Asn Leu Thr
1               5                   10                  15

Ser Met Gln Arg Ile Ala Phe Ile Val Lys Leu Asp Asp
            20                  25
```

```
<210> SEQ ID NO 10
<211> LENGTH: 29
<212> TYPE: PRT
<213> ORGANISM: Artificial sequence
<220> FEATURE:
<223> OTHER INFORMATION: Engineered ABD binding polypeptide

<400> SEQUENCE: 10

Glu Leu Thr Thr Ala Phe Ala Glu Ile Gln Lys Leu Pro Asn Leu Thr
1               5                   10                  15

Phe Glu Gln Lys Ile Ala Phe Ile Ile Lys Leu Asp Asp
            20                  25
```

```
<210> SEQ ID NO 11
<211> LENGTH: 29
<212> TYPE: PRT
<213> ORGANISM: Artificial sequence
<220> FEATURE:
<223> OTHER INFORMATION: Engineered ABD binding polypeptide

<400> SEQUENCE: 11

Glu Phe Arg Glu Ala Ile Ile Glu Ile Arg Arg Leu Pro Asn Leu Thr
1               5                   10                  15

Leu His Gln Arg Leu Ala Phe Ile Met Lys Leu Asp Asp
            20                  25
```

```
<210> SEQ ID NO 12
<211> LENGTH: 29
<212> TYPE: PRT
<213> ORGANISM: Artificial sequence
<220> FEATURE:
<223> OTHER INFORMATION: Engineered ABD binding polypeptide

<400> SEQUENCE: 12

Glu Ile Lys Thr Ala Phe Ala Glu Ile Arg Val Leu Pro Asn Leu Thr
1               5                   10                  15

Phe Ala Gln Arg Leu Ala Phe Ile Ile Lys Leu Asp Asp
            20                  25
```

```
<210> SEQ ID NO 13
<211> LENGTH: 29
<212> TYPE: PRT
<213> ORGANISM: Artificial sequence
<220> FEATURE:
<223> OTHER INFORMATION: Engineered ABD binding polypeptide

<400> SEQUENCE: 13

Glu Arg Arg Tyr Ala Phe Arg Glu Ile Arg Leu Leu Pro Asn Leu Thr
```

```
                1               5                   10                  15
Phe Ser Gln Arg Ile Ala Phe Ile Val Lys Leu Asp Asp
            20                  25

<210> SEQ ID NO 14
<211> LENGTH: 29
<212> TYPE: PRT
<213> ORGANISM: Artificial sequence
<220> FEATURE:
<223> OTHER INFORMATION: Engineered ABD binding polypeptide

<400> SEQUENCE: 14

Glu Leu Lys Ala Ala Phe Arg Glu Ile Asn Asp Leu Pro Asn Leu Thr
1               5                   10                  15

His Thr Gln Arg Ile Ala Phe Ile Leu Lys Leu Asp Asp
            20                  25

<210> SEQ ID NO 15
<211> LENGTH: 29
<212> TYPE: PRT
<213> ORGANISM: Artificial sequence
<220> FEATURE:
<223> OTHER INFORMATION: Engineered ABD binding polypeptide

<400> SEQUENCE: 15

Glu Leu Lys Met Ala Phe Gln Glu Ile Arg Tyr Leu Pro Asn Leu Thr
1               5                   10                  15

Arg Leu Gln Arg Ile Ala Phe Ile Val Lys Leu Asp Asp
            20                  25

<210> SEQ ID NO 16
<211> LENGTH: 29
<212> TYPE: PRT
<213> ORGANISM: Artificial sequence
<220> FEATURE:
<223> OTHER INFORMATION: Engineered ABD binding polypeptide

<400> SEQUENCE: 16

Glu Trp Lys Lys Ala Leu Arg Glu Ile His Tyr Leu Pro Asn Leu Thr
1               5                   10                  15

Leu Thr Gln Arg Leu Ala Phe Ile Val Lys Leu Asp Asp
            20                  25

<210> SEQ ID NO 17
<211> LENGTH: 29
<212> TYPE: PRT
<213> ORGANISM: Artificial sequence
<220> FEATURE:
<223> OTHER INFORMATION: Engineered ABD binding polypeptide

<400> SEQUENCE: 17

Glu Phe Glu Lys Ala Leu Val Glu Ile Lys Thr Leu Pro Asn Leu Thr
1               5                   10                  15

Ala Ile Gln Arg Ile Ala Phe Ile Val Lys Leu Asp Asp
            20                  25

<210> SEQ ID NO 18
<211> LENGTH: 29
<212> TYPE: PRT
<213> ORGANISM: Artificial sequence
<220> FEATURE:
<223> OTHER INFORMATION: Engineered ABD binding polypeptide

<400> SEQUENCE: 18
```

```
Glu Phe Ile Phe Ala Leu Ser Glu Ile Lys Val Leu Pro Asn Leu Thr
1               5                   10                  15

His Val Gln Lys Ile Ala Phe Ile Val Lys Leu Asp Asp
            20                  25
```

<210> SEQ ID NO 19
<211> LENGTH: 29
<212> TYPE: PRT
<213> ORGANISM: Artificial sequence
<220> FEATURE:
<223> OTHER INFORMATION: Engineered ABD binding polypeptide

<400> SEQUENCE: 19

```
Glu Phe Lys Tyr Ala Ile Gln Glu Ile Lys Asp Leu Pro Asn Leu Thr
1               5                   10                  15

Ser Gly Gln Arg Ile Ala Phe Ile Val Lys Leu Asp Asp
            20                  25
```

<210> SEQ ID NO 20
<211> LENGTH: 29
<212> TYPE: PRT
<213> ORGANISM: Artificial sequence
<220> FEATURE:
<223> OTHER INFORMATION: Engineered ABD binding polypeptide

<400> SEQUENCE: 20

```
Glu Leu Asn Gln Ala Leu Trp Glu Ile Arg Gln Leu Pro Asn Leu Thr
1               5                   10                  15

Phe Asn Gln Arg Val Ala Phe Ile Val Lys Leu Asp Asp
            20                  25
```

<210> SEQ ID NO 21
<211> LENGTH: 29
<212> TYPE: PRT
<213> ORGANISM: Artificial sequence
<220> FEATURE:
<223> OTHER INFORMATION: Engineered ABD binding polypeptide

<400> SEQUENCE: 21

```
Glu Leu Gln Gly Ala Leu Thr Glu Ile Lys Asn Leu Pro Asn Leu Thr
1               5                   10                  15

Gly His Gln Arg Ile Ala Phe Ile Val Lys Leu Asp Asp
            20                  25
```

<210> SEQ ID NO 22
<211> LENGTH: 29
<212> TYPE: PRT
<213> ORGANISM: Artificial sequence
<220> FEATURE:
<223> OTHER INFORMATION: Engineered ABD binding polypeptide

<400> SEQUENCE: 22

```
Glu Leu Ala Asp Ala Leu Tyr Glu Ile Lys Asn Leu Pro Asn Leu Thr
1               5                   10                  15

His Glu Gln His Ile Ala Phe Ile Val Lys Leu Asp Asp
            20                  25
```

<210> SEQ ID NO 23
<211> LENGTH: 29
<212> TYPE: PRT
<213> ORGANISM: Artificial sequence
<220> FEATURE:
<223> OTHER INFORMATION: Engineered ABD binding polypeptide

<400> SEQUENCE: 23

Glu Leu Gly Val Ala Leu Lys Glu Ile Gly Gln Leu Pro Asn Leu Thr
1               5                   10                  15

His Thr Gln Arg Ile Ala Phe Ile Ile Lys Leu Asp Asp
            20                  25

<210> SEQ ID NO 24
<211> LENGTH: 29
<212> TYPE: PRT
<213> ORGANISM: Artificial sequence
<220> FEATURE:
<223> OTHER INFORMATION: Engineered ABD binding polypeptide

<400> SEQUENCE: 24

Glu Leu Ser Ile Ala Leu Asn Glu Ile Lys Gly Leu Pro Asn Leu Thr
1               5                   10                  15

Ser Leu Gln Lys Ile Ala Phe Ile Val Lys Leu Asp Asp
            20                  25

<210> SEQ ID NO 25
<211> LENGTH: 29
<212> TYPE: PRT
<213> ORGANISM: Artificial sequence
<220> FEATURE:
<223> OTHER INFORMATION: Engineered ABD binding polypeptide

<400> SEQUENCE: 25

Glu Ile Arg Ser Ala Tyr Lys Glu Ile Asn Val Leu Pro Asn Leu Thr
1               5                   10                  15

Phe Ser Gln Lys Ile Ala Phe Ile Tyr Lys Leu Glu Asp
            20                  25

<210> SEQ ID NO 26
<211> LENGTH: 29
<212> TYPE: PRT
<213> ORGANISM: Artificial sequence
<220> FEATURE:
<223> OTHER INFORMATION: Engineered ABD binding polypeptide

<400> SEQUENCE: 26

Glu Leu Ser Ser Ala Leu Leu Glu Ile Ser His Leu Pro Asn Leu Thr
1               5                   10                  15

His Gln Gln Arg Ile Ala Phe Ile Val Lys Leu Asp Asp
            20                  25

<210> SEQ ID NO 27
<211> LENGTH: 29
<212> TYPE: PRT
<213> ORGANISM: Artificial sequence
<220> FEATURE:
<223> OTHER INFORMATION: Engineered ABD binding polypeptide

<400> SEQUENCE: 27

Glu Leu Val His Ala Phe Gly Glu Ile Arg Tyr Leu Pro Asn Leu Thr
1               5                   10                  15

His Ser Gln Arg Ile Ala Phe Ile Ile Lys Leu Asp Asp
            20                  25

<210> SEQ ID NO 28
<211> LENGTH: 29
<212> TYPE: PRT
<213> ORGANISM: Artificial sequence
<220> FEATURE:
<223> OTHER INFORMATION: Engineered ABD binding polypeptide

```
<400> SEQUENCE: 28

Glu Leu His Asn Ala Phe Ser Glu Ile Lys Gln Leu Pro Asn Leu Thr
1               5                   10                  15

Thr Gln Gln Arg Ile Ala Phe Ile Ile Lys Leu Asp Asp
            20                  25

<210> SEQ ID NO 29
<211> LENGTH: 29
<212> TYPE: PRT
<213> ORGANISM: Artificial sequence
<220> FEATURE:
<223> OTHER INFORMATION: Engineered ABD binding polypeptide

<400> SEQUENCE: 29

Glu Gly Val Asn Ala Phe Asn Glu Ile Lys Gly Leu Pro Asn Leu Thr
1               5                   10                  15

Phe His Gln Lys Ile Ala Phe Ile Val Lys Leu Asp Asp
            20                  25

<210> SEQ ID NO 30
<211> LENGTH: 29
<212> TYPE: PRT
<213> ORGANISM: Artificial sequence
<220> FEATURE:
<223> OTHER INFORMATION: Engineered ABD binding polypeptide

<400> SEQUENCE: 30

Glu Leu Lys Tyr Ala Leu Met Glu Ile Arg Tyr Leu Pro Asn Leu Thr
1               5                   10                  15

His Arg Gln Lys Ile Ala Phe Ile Leu Lys Leu Asp Asp
            20                  25

<210> SEQ ID NO 31
<211> LENGTH: 29
<212> TYPE: PRT
<213> ORGANISM: Artificial sequence
<220> FEATURE:
<223> OTHER INFORMATION: Engineered ABD binding polypeptide

<400> SEQUENCE: 31

Glu Leu Arg Trp Ala Val Ser Glu Ile Arg His Leu Pro Asn Leu Thr
1               5                   10                  15

Phe His Gln Arg Ile Ala Phe Ile Val Lys Leu Asp Asp
            20                  25

<210> SEQ ID NO 32
<211> LENGTH: 29
<212> TYPE: PRT
<213> ORGANISM: Artificial sequence
<220> FEATURE:
<223> OTHER INFORMATION: Engineered ABD binding polypeptide

<400> SEQUENCE: 32

Glu Leu Gln Arg Ala Phe Ala Glu Ile Gln Ser Leu Pro Asn Leu Thr
1               5                   10                  15

Leu Asn Gln His Ile Ala Phe Ile Tyr Lys Leu Glu Asp
            20                  25

<210> SEQ ID NO 33
<211> LENGTH: 29
<212> TYPE: PRT
<213> ORGANISM: Artificial sequence
<220> FEATURE:
<223> OTHER INFORMATION: Engineered ABD binding polypeptide
```

<400> SEQUENCE: 33

Glu Leu Lys Ala Ala Phe Arg Glu Ile Arg Thr Leu Pro Asn Leu Thr
1               5                   10                  15

Phe Gly Gln Arg Thr Ala Phe Ile Val Lys Leu Asp Asp
            20                  25

<210> SEQ ID NO 34
<211> LENGTH: 29
<212> TYPE: PRT
<213> ORGANISM: Artificial sequence
<220> FEATURE:
<223> OTHER INFORMATION: Engineered ABD binding polypeptide

<400> SEQUENCE: 34

Glu Leu Thr Thr Ala Met Lys Glu Ile Gln Ala Leu Pro Asn Leu Thr
1               5                   10                  15

His Gln Gln Arg Ile Ala Phe Ile Val Lys Leu Asp Asp
            20                  25

<210> SEQ ID NO 35
<211> LENGTH: 29
<212> TYPE: PRT
<213> ORGANISM: Artificial sequence
<220> FEATURE:
<223> OTHER INFORMATION: Engineered ABD binding polypeptide

<400> SEQUENCE: 35

Glu Asp Met Arg Ala Phe His Glu Ile Asn Lys Leu Pro Asn Leu Thr
1               5                   10                  15

Leu Ala Gln Arg Val Ala Phe Ile Tyr Lys Leu Glu Asp
            20                  25

<210> SEQ ID NO 36
<211> LENGTH: 29
<212> TYPE: PRT
<213> ORGANISM: Artificial sequence
<220> FEATURE:
<223> OTHER INFORMATION: Engineered ABD binding polypeptide

<400> SEQUENCE: 36

Glu Leu Asn Ala Ala Phe Thr Glu Ile Ser Ser Leu Pro Asn Leu Thr
1               5                   10                  15

Leu Asp Gln Arg Leu Ala Phe Ile Phe Lys Leu Asp Asp
            20                  25

<210> SEQ ID NO 37
<211> LENGTH: 29
<212> TYPE: PRT
<213> ORGANISM: Artificial sequence
<220> FEATURE:
<223> OTHER INFORMATION: Engineered ABD binding polypeptide

<400> SEQUENCE: 37

Glu Leu Arg Trp Ala Leu Asn Glu Ile His Ile Leu Pro Asn Leu Thr
1               5                   10                  15

Leu Glu Gln Lys Val Ala Phe Ile Val Lys Leu Asp Asp
            20                  25

<210> SEQ ID NO 38
<211> LENGTH: 29
<212> TYPE: PRT
<213> ORGANISM: Artificial sequence
<220> FEATURE:

-continued

<223> OTHER INFORMATION: Engineered ABD binding polypeptide

<400> SEQUENCE: 38

Glu Leu Lys Asn Ala Phe Ile Glu Ile Lys Asn Leu Pro Asn Leu Thr
1               5                   10                  15

Thr Asn Gln Thr Leu Ala Phe Ile Val Lys Leu Asp Asp
            20                  25

<210> SEQ ID NO 39
<211> LENGTH: 29
<212> TYPE: PRT
<213> ORGANISM: Artificial sequence
<220> FEATURE:
<223> OTHER INFORMATION: Engineered ABD binding polypeptide

<400> SEQUENCE: 39

Glu Leu Ser Leu Ala Phe Val Glu Ile His Lys Leu Pro Asn Leu Thr
1               5                   10                  15

His His Gln Arg Leu Ala Phe Ile Val Lys Leu Asp Asp
            20                  25

<210> SEQ ID NO 40
<211> LENGTH: 29
<212> TYPE: PRT
<213> ORGANISM: Artificial sequence
<220> FEATURE:
<223> OTHER INFORMATION: Engineered ABD binding polypeptide

<400> SEQUENCE: 40

Glu Leu Gln Trp Ala Phe Asn Glu Ile His Asn Leu Pro Asn Leu Thr
1               5                   10                  15

Tyr Val Gln Arg Ile Ala Phe Ile Val Lys Leu Asp Asp
            20                  25

<210> SEQ ID NO 41
<211> LENGTH: 29
<212> TYPE: PRT
<213> ORGANISM: Artificial sequence
<220> FEATURE:
<223> OTHER INFORMATION: Engineered ABD binding polypeptide

<400> SEQUENCE: 41

Glu Glu Gln Thr Ala Met Gln Glu Ile Asn Ser Leu Pro Asn Leu Thr
1               5                   10                  15

Leu Glu Gln Arg Ile Ala Phe Ile Phe Lys Leu Glu Asp
            20                  25

<210> SEQ ID NO 42
<211> LENGTH: 29
<212> TYPE: PRT
<213> ORGANISM: Artificial sequence
<220> FEATURE:
<223> OTHER INFORMATION: Engineered ABD binding polypeptide

<400> SEQUENCE: 42

Glu Leu Gly Trp Ala Phe Arg Glu Ile Arg Asn Leu Pro Asn Leu Thr
1               5                   10                  15

His Tyr Gln Arg Ile Ala Phe Ile Met Lys Leu Asp Asp
            20                  25

<210> SEQ ID NO 43
<211> LENGTH: 29
<212> TYPE: PRT
<213> ORGANISM: Artificial sequence

```
<220> FEATURE:
<223> OTHER INFORMATION: Engineered ABD binding polypeptide

<400> SEQUENCE: 43

Glu Asn Leu Trp Ala Phe Asn Glu Ile Lys Gly Leu Pro Asn Leu Thr
1               5                   10                  15

His Asp Gln Arg Ile Ala Phe Ile Val Lys Leu Asp Asp
            20                  25

<210> SEQ ID NO 44
<211> LENGTH: 29
<212> TYPE: PRT
<213> ORGANISM: Artificial sequence
<220> FEATURE:
<223> OTHER INFORMATION: Engineered ABD binding polypeptide

<400> SEQUENCE: 44

Glu Leu Ser Phe Ala Phe Ser Glu Ile Asn Val Leu Pro Asn Leu Thr
1               5                   10                  15

Phe His Gln Lys Ile Ala Phe Ile Tyr Lys Leu Glu Asp
            20                  25

<210> SEQ ID NO 45
<211> LENGTH: 29
<212> TYPE: PRT
<213> ORGANISM: Artificial sequence
<220> FEATURE:
<223> OTHER INFORMATION: Engineered ABD binding polypeptide

<400> SEQUENCE: 45

Glu Phe Arg Gly Ala Ile Ala Glu Ile Arg Asp Leu Pro Asn Leu Thr
1               5                   10                  15

Leu Glu Gln Lys Tyr Ala Phe Ile Phe Lys Leu Glu Asp
            20                  25

<210> SEQ ID NO 46
<211> LENGTH: 29
<212> TYPE: PRT
<213> ORGANISM: Artificial sequence
<220> FEATURE:
<223> OTHER INFORMATION: Engineered ABD binding polypeptide

<400> SEQUENCE: 46

Glu Glu Glu Asn Ala Tyr Lys Glu Ile Gly Ser Leu Pro Asn Leu Thr
1               5                   10                  15

Leu Ala Gln Lys Val Ala Phe Ile Leu Lys Leu Glu Asp
            20                  25

<210> SEQ ID NO 47
<211> LENGTH: 29
<212> TYPE: PRT
<213> ORGANISM: Artificial sequence
<220> FEATURE:
<223> OTHER INFORMATION: Engineered ABD binding polypeptide

<400> SEQUENCE: 47

Glu Leu Arg Gln Ala Leu Gln Glu Ile His Ile Leu Pro Asn Leu Thr
1               5                   10                  15

His Ser Gln Arg Val Ala Phe Ile Val Lys Leu Asp Asp
            20                  25

<210> SEQ ID NO 48
<211> LENGTH: 29
<212> TYPE: PRT
```

<213> ORGANISM: Artificial sequence
<220> FEATURE:
<223> OTHER INFORMATION: Engineered ABD binding polypeptide

<400> SEQUENCE: 48

Glu Asn His Ala Ala Phe Gln Glu Ile Leu Ser Leu Pro Asn Leu Thr
1               5                   10                  15

Leu Asn Gln Arg Leu Ala Phe Ile Thr Lys Leu Asp Asp
            20                  25

<210> SEQ ID NO 49
<211> LENGTH: 29
<212> TYPE: PRT
<213> ORGANISM: Artificial sequence
<220> FEATURE:
<223> OTHER INFORMATION: Engineered ABD binding polypeptide

<400> SEQUENCE: 49

Glu Thr Asn Tyr Ala Phe Lys Glu Ile Asp Leu Leu Pro Asn Leu Thr
1               5                   10                  15

Leu Met Gln Lys Leu Ala Phe Ile Val Lys Leu Asp Asp
            20                  25

<210> SEQ ID NO 50
<211> LENGTH: 29
<212> TYPE: PRT
<213> ORGANISM: Artificial sequence
<220> FEATURE:
<223> OTHER INFORMATION: Engineered ABD binding polypeptide

<400> SEQUENCE: 50

Glu Ile Ser Leu Ala Phe Lys Glu Ile Lys Ala Leu Pro Asn Leu Thr
1               5                   10                  15

Gly Gln Gln Arg Phe Ala Phe Ile Leu Lys Leu Asp Asp
            20                  25

<210> SEQ ID NO 51
<211> LENGTH: 29
<212> TYPE: PRT
<213> ORGANISM: Artificial sequence
<220> FEATURE:
<223> OTHER INFORMATION: Engineered ABD binding polypeptide

<400> SEQUENCE: 51

Glu Leu Ser Lys Ala Leu Thr Glu Ile Arg Met Leu Pro Asn Leu Thr
1               5                   10                  15

Phe Arg Gln Arg Ile Ala Phe Ile Ile Lys Leu Asp Asp
            20                  25

<210> SEQ ID NO 52
<211> LENGTH: 29
<212> TYPE: PRT
<213> ORGANISM: Artificial sequence
<220> FEATURE:
<223> OTHER INFORMATION: Engineered ABD binding polypeptide

<400> SEQUENCE: 52

Glu Leu Asp Met Ala Tyr Thr Glu Ile Gly Leu Leu Pro Asn Leu Thr
1               5                   10                  15

Phe Ser Gln Leu Leu Ala Phe Ile Ile Lys Leu Asp Asp
            20                  25

<210> SEQ ID NO 53
<211> LENGTH: 49

<212> TYPE: PRT
<213> ORGANISM: Artificial sequence
<220> FEATURE:
<223> OTHER INFORMATION: Engineered ABD binding polypeptide

<400> SEQUENCE: 53

Lys Glu Leu Lys Val Ala Phe Lys Glu Ile Asn Thr Leu Pro Asn Leu
1               5                   10                  15

Thr His Gln Gln Arg Ile Ala Phe Ile Ile Lys Leu Asp Asp Asp Pro
            20                  25                  30

Ser Gln Ser Ser Glu Leu Leu Ala Glu Ala Lys Lys Leu Asn Asp Ala
        35                  40                  45

Gln

<210> SEQ ID NO 54
<211> LENGTH: 49
<212> TYPE: PRT
<213> ORGANISM: Artificial sequence
<220> FEATURE:
<223> OTHER INFORMATION: Engineered ABD binding polypeptide

<400> SEQUENCE: 54

Lys Glu Leu Val Asn Ala Phe Ser Glu Ile Lys Ala Leu Pro Asn Leu
1               5                   10                  15

Thr Leu His Gln Arg Leu Ala Phe Ile Val Lys Leu Asp Asp Asp Pro
            20                  25                  30

Ser Gln Ser Ser Glu Leu Leu Ala Glu Ala Lys Lys Leu Asn Asp Ala
        35                  40                  45

Gln

<210> SEQ ID NO 55
<211> LENGTH: 49
<212> TYPE: PRT
<213> ORGANISM: Artificial sequence
<220> FEATURE:
<223> OTHER INFORMATION: Engineered ABD binding polypeptide

<400> SEQUENCE: 55

Lys Glu Leu His His Ala Phe Arg Glu Ile Lys Phe Leu Pro Asn Leu
1               5                   10                  15

Thr Phe His Gln Arg Leu Ala Phe Ile Val Lys Leu Asp Asp Asp Pro
            20                  25                  30

Ser Gln Ser Ser Glu Leu Leu Ala Glu Ala Lys Lys Leu Asn Asp Ala
        35                  40                  45

Gln

<210> SEQ ID NO 56
<211> LENGTH: 49
<212> TYPE: PRT
<213> ORGANISM: Artificial sequence
<220> FEATURE:
<223> OTHER INFORMATION: Engineered ABD binding polypeptide

<400> SEQUENCE: 56

Lys Glu Phe Lys Leu Ala Leu Gln Glu Ile His Tyr Leu Pro Asn Leu
1               5                   10                  15

Thr Leu Asp Gln Arg Leu Ala Phe Ile Leu Lys Leu Asp Asp Asp Pro
            20                  25                  30

Ser Gln Ser Ser Glu Leu Leu Ala Glu Ala Lys Lys Leu Asn Asp Ala
        35                  40                  45

Gln

<210> SEQ ID NO 57
<211> LENGTH: 49
<212> TYPE: PRT
<213> ORGANISM: Artificial sequence
<220> FEATURE:
<223> OTHER INFORMATION: Engineered ABD binding polypeptide

<400> SEQUENCE: 57

Lys Glu Leu Arg Trp Ala Leu Asn Glu Ile Arg Arg Leu Pro Asn Leu
1               5                   10                  15

Thr Phe Lys Gln His Ile Ala Phe Ile Val Lys Leu Asp Asp Asp Pro
            20                  25                  30

Ser Gln Ser Ser Glu Leu Leu Ala Glu Ala Lys Lys Leu Asn Asp Ala
        35                  40                  45

Gln

<210> SEQ ID NO 58
<211> LENGTH: 49
<212> TYPE: PRT
<213> ORGANISM: Artificial sequence
<220> FEATURE:
<223> OTHER INFORMATION: Engineered ABD binding polypeptide

<400> SEQUENCE: 58

Lys Glu Phe Arg Ala Ala Leu Leu Glu Ile Lys Leu Leu Pro Asn Leu
1               5                   10                  15

Thr Phe Ile Gln Arg Leu Ala Phe Ile Val Lys Leu Asp Asp Asp Pro
            20                  25                  30

Ser Gln Ser Ser Glu Leu Leu Ala Glu Ala Lys Lys Leu Asn Asp Ala
        35                  40                  45

Gln

<210> SEQ ID NO 59
<211> LENGTH: 49
<212> TYPE: PRT
<213> ORGANISM: Artificial sequence
<220> FEATURE:
<223> OTHER INFORMATION: Engineered ABD binding polypeptide

<400> SEQUENCE: 59

Lys Glu Phe Thr Ile Ala Leu Arg Glu Ile His Ala Leu Pro Asn Leu
1               5                   10                  15

Thr Leu His Gln Arg Leu Ala Phe Ile Ile Lys Leu Asp Asp Asp Pro
            20                  25                  30

Ser Gln Ser Ser Glu Leu Leu Ala Glu Ala Lys Lys Leu Asn Asp Ala
        35                  40                  45

Gln

<210> SEQ ID NO 60
<211> LENGTH: 49
<212> TYPE: PRT
<213> ORGANISM: Artificial sequence
<220> FEATURE:
<223> OTHER INFORMATION: Engineered ABD binding polypeptide

<400> SEQUENCE: 60

Lys Glu Leu Arg Lys Ala Phe His Glu Ile Gln Ile Leu Pro Asn Leu
1               5                   10                  15

Thr Leu Ser Gln Arg Leu Ala Phe Ile Val Lys Leu Asp Asp Asp Pro

```
                    20                  25                  30

Ser Gln Ser Ser Glu Leu Leu Ala Glu Ala Lys Lys Leu Asn Asp Ala
        35                  40                  45

Gln

<210> SEQ ID NO 61
<211> LENGTH: 49
<212> TYPE: PRT
<213> ORGANISM: Artificial sequence
<220> FEATURE:
<223> OTHER INFORMATION: Engineered ABD binding polypeptide

<400> SEQUENCE: 61

Lys Glu Phe Lys Asp Ala Leu Asp Glu Ile Lys Asp Leu Pro Asn Leu
1               5                   10                  15

Thr Ser Met Gln Arg Ile Ala Phe Ile Val Lys Leu Asp Asp Asp Pro
                20                  25                  30

Ser Gln Ser Ser Glu Leu Leu Ala Glu Ala Lys Lys Leu Asn Asp Ala
        35                  40                  45

Gln

<210> SEQ ID NO 62
<211> LENGTH: 49
<212> TYPE: PRT
<213> ORGANISM: Artificial sequence
<220> FEATURE:
<223> OTHER INFORMATION: Engineered ABD binding polypeptide

<400> SEQUENCE: 62

Lys Glu Leu Thr Thr Ala Phe Ala Glu Ile Gln Lys Leu Pro Asn Leu
1               5                   10                  15

Thr Phe Glu Gln Lys Ile Ala Phe Ile Ile Lys Leu Asp Asp Asp Pro
                20                  25                  30

Ser Gln Ser Ser Glu Leu Leu Ala Glu Ala Lys Lys Leu Asn Asp Ala
        35                  40                  45

Gln

<210> SEQ ID NO 63
<211> LENGTH: 49
<212> TYPE: PRT
<213> ORGANISM: Artificial sequence
<220> FEATURE:
<223> OTHER INFORMATION: Engineered ABD binding polypeptide

<400> SEQUENCE: 63

Lys Glu Phe Arg Glu Ala Ile Ile Glu Ile Arg Arg Leu Pro Asn Leu
1               5                   10                  15

Thr Leu His Gln Arg Leu Ala Phe Ile Met Lys Leu Asp Asp Asp Pro
                20                  25                  30

Ser Gln Ser Ser Glu Leu Leu Ala Glu Ala Lys Lys Leu Asn Asp Ala
        35                  40                  45

Gln

<210> SEQ ID NO 64
<211> LENGTH: 49
<212> TYPE: PRT
<213> ORGANISM: Artificial sequence
<220> FEATURE:
<223> OTHER INFORMATION: Engineered ABD binding polypeptide

<400> SEQUENCE: 64
```

-continued

Lys Glu Ile Lys Thr Ala Phe Ala Glu Ile Arg Val Leu Pro Asn Leu
1               5                   10                  15

Thr Phe Ala Gln Arg Leu Ala Phe Ile Ile Lys Leu Asp Asp Pro
            20                  25                  30

Ser Gln Ser Ser Glu Leu Leu Ala Glu Ala Lys Lys Leu Asn Asp Ala
        35                  40                  45

Gln

<210> SEQ ID NO 65
<211> LENGTH: 49
<212> TYPE: PRT
<213> ORGANISM: Artificial sequence
<220> FEATURE:
<223> OTHER INFORMATION: Engineered ABD binding polypeptide

<400> SEQUENCE: 65

Lys Glu Arg Arg Tyr Ala Phe Arg Glu Ile Arg Leu Leu Pro Asn Leu
1               5                   10                  15

Thr Phe Ser Gln Arg Ile Ala Phe Ile Val Lys Leu Asp Asp Pro
            20                  25                  30

Ser Gln Ser Ser Glu Leu Leu Ala Glu Ala Lys Lys Leu Asn Asp Ala
        35                  40                  45

Gln

<210> SEQ ID NO 66
<211> LENGTH: 49
<212> TYPE: PRT
<213> ORGANISM: Artificial sequence
<220> FEATURE:
<223> OTHER INFORMATION: Engineered ABD binding polypeptide

<400> SEQUENCE: 66

Lys Glu Leu Lys Ala Ala Phe Arg Glu Ile Asn Asp Leu Pro Asn Leu
1               5                   10                  15

Thr His Thr Gln Arg Ile Ala Phe Ile Leu Lys Leu Asp Asp Pro
            20                  25                  30

Ser Gln Ser Ser Glu Leu Leu Ala Glu Ala Lys Lys Leu Asn Asp Ala
        35                  40                  45

Gln

<210> SEQ ID NO 67
<211> LENGTH: 49
<212> TYPE: PRT
<213> ORGANISM: Artificial sequence
<220> FEATURE:
<223> OTHER INFORMATION: Engineered ABD binding polypeptide

<400> SEQUENCE: 67

Lys Glu Leu Lys Met Ala Phe Gln Glu Ile Arg Tyr Leu Pro Asn Leu
1               5                   10                  15

Thr Arg Leu Gln Arg Ile Ala Phe Ile Val Lys Leu Asp Asp Pro
            20                  25                  30

Ser Gln Ser Ser Glu Leu Leu Ala Glu Ala Lys Lys Leu Asn Asp Ala
        35                  40                  45

Gln

<210> SEQ ID NO 68
<211> LENGTH: 49
<212> TYPE: PRT

```
<213> ORGANISM: Artificial sequence
<220> FEATURE:
<223> OTHER INFORMATION: Engineered ABD binding polypeptide

<400> SEQUENCE: 68

Lys Glu Trp Lys Lys Ala Leu Arg Glu Ile His Tyr Leu Pro Asn Leu
1               5                   10                  15

Thr Leu Thr Gln Arg Leu Ala Phe Ile Val Lys Leu Asp Asp Asp Pro
            20                  25                  30

Ser Gln Ser Ser Glu Leu Leu Ala Glu Ala Lys Lys Leu Asn Asp Ala
        35                  40                  45

Gln

<210> SEQ ID NO 69
<211> LENGTH: 49
<212> TYPE: PRT
<213> ORGANISM: Artificial sequence
<220> FEATURE:
<223> OTHER INFORMATION: Engineered ABD binding polypeptide

<400> SEQUENCE: 69

Lys Glu Phe Glu Lys Ala Leu Val Glu Ile Lys Thr Leu Pro Asn Leu
1               5                   10                  15

Thr Ala Ile Gln Arg Ile Ala Phe Ile Val Lys Leu Asp Asp Asp Pro
            20                  25                  30

Ser Gln Ser Ser Glu Leu Leu Ala Glu Ala Lys Lys Leu Asn Asp Ala
        35                  40                  45

Gln

<210> SEQ ID NO 70
<211> LENGTH: 49
<212> TYPE: PRT
<213> ORGANISM: Artificial sequence
<220> FEATURE:
<223> OTHER INFORMATION: Engineered ABD binding polypeptide

<400> SEQUENCE: 70

Lys Glu Phe Ile Phe Ala Leu Ser Glu Ile Lys Val Leu Pro Asn Leu
1               5                   10                  15

Thr His Val Gln Lys Ile Ala Phe Ile Val Lys Leu Asp Asp Asp Pro
            20                  25                  30

Ser Gln Ser Ser Glu Leu Leu Ala Glu Ala Lys Lys Leu Asn Asp Ala
        35                  40                  45

Gln

<210> SEQ ID NO 71
<211> LENGTH: 49
<212> TYPE: PRT
<213> ORGANISM: Artificial sequence
<220> FEATURE:
<223> OTHER INFORMATION: Engineered ABD binding polypeptide

<400> SEQUENCE: 71

Lys Glu Phe Lys Tyr Ala Ile Gln Glu Ile Lys Asp Leu Pro Asn Leu
1               5                   10                  15

Thr Ser Gly Gln Arg Ile Ala Phe Ile Val Lys Leu Asp Asp Asp Pro
            20                  25                  30

Ser Gln Ser Ser Glu Leu Leu Ala Glu Ala Lys Lys Leu Asn Asp Ala
        35                  40                  45

Gln
```

```
<210> SEQ ID NO 72
<211> LENGTH: 49
<212> TYPE: PRT
<213> ORGANISM: Artificial sequence
<220> FEATURE:
<223> OTHER INFORMATION: Engineered ABD binding polypeptide

<400> SEQUENCE: 72

Lys Glu Leu Asn Gln Ala Leu Trp Glu Ile Arg Gln Leu Pro Asn Leu
1               5                   10                  15

Thr Phe Asn Gln Arg Val Ala Phe Ile Val Lys Leu Asp Asp Asp Pro
            20                  25                  30

Ser Gln Ser Ser Glu Leu Leu Ala Glu Ala Lys Lys Leu Asn Asp Ala
        35                  40                  45

Gln

<210> SEQ ID NO 73
<211> LENGTH: 49
<212> TYPE: PRT
<213> ORGANISM: Artificial sequence
<220> FEATURE:
<223> OTHER INFORMATION: Engineered ABD binding polypeptide

<400> SEQUENCE: 73

Lys Glu Leu Gln Gly Ala Leu Thr Glu Ile Lys Asn Leu Pro Asn Leu
1               5                   10                  15

Thr Gly His Gln Arg Ile Ala Phe Ile Val Lys Leu Asp Asp Asp Pro
            20                  25                  30

Ser Gln Ser Ser Glu Leu Leu Ala Glu Ala Lys Lys Leu Asn Asp Ala
        35                  40                  45

Gln

<210> SEQ ID NO 74
<211> LENGTH: 49
<212> TYPE: PRT
<213> ORGANISM: Artificial sequence
<220> FEATURE:
<223> OTHER INFORMATION: Engineered ABD binding polypeptide

<400> SEQUENCE: 74

Lys Glu Leu Ala Asp Ala Leu Tyr Glu Ile Lys Asn Leu Pro Asn Leu
1               5                   10                  15

Thr His Glu Gln His Ile Ala Phe Ile Val Lys Leu Asp Asp Asp Pro
            20                  25                  30

Ser Gln Ser Ser Glu Leu Leu Ala Glu Ala Lys Lys Leu Asn Asp Ala
        35                  40                  45

Gln

<210> SEQ ID NO 75
<211> LENGTH: 49
<212> TYPE: PRT
<213> ORGANISM: Artificial sequence
<220> FEATURE:
<223> OTHER INFORMATION: Engineered ABD binding polypeptide

<400> SEQUENCE: 75

Lys Glu Leu Gly Val Ala Leu Lys Glu Ile Gly Gln Leu Pro Asn Leu
1               5                   10                  15

Thr His Thr Gln Arg Ile Ala Phe Ile Ile Lys Leu Asp Asp Asp Pro
            20                  25                  30
```

Ser Gln Ser Ser Glu Leu Leu Ala Glu Ala Lys Lys Leu Asn Asp Ala
        35                  40                  45

Gln

<210> SEQ ID NO 76
<211> LENGTH: 49
<212> TYPE: PRT
<213> ORGANISM: Artificial sequence
<220> FEATURE:
<223> OTHER INFORMATION: Engineered ABD binding polypeptide

<400> SEQUENCE: 76

Lys Glu Leu Ser Ile Ala Leu Asn Glu Ile Lys Gly Leu Pro Asn Leu
1               5                   10                  15

Thr Ser Leu Gln Lys Ile Ala Phe Ile Val Lys Leu Asp Asp Asp Pro
            20                  25                  30

Ser Gln Ser Ser Glu Leu Leu Ala Glu Ala Lys Lys Leu Asn Asp Ala
        35                  40                  45

Gln

<210> SEQ ID NO 77
<211> LENGTH: 49
<212> TYPE: PRT
<213> ORGANISM: Artificial sequence
<220> FEATURE:
<223> OTHER INFORMATION: Engineered ABD binding polypeptide

<400> SEQUENCE: 77

Lys Glu Ile Arg Ser Ala Tyr Lys Glu Ile Asn Val Leu Pro Asn Leu
1               5                   10                  15

Thr Phe Ser Gln Lys Ile Ala Phe Ile Tyr Lys Leu Glu Asp Asp Pro
            20                  25                  30

Ser Gln Ser Ser Glu Leu Leu Ala Glu Ala Lys Lys Leu Asn Asp Ala
        35                  40                  45

Gln

<210> SEQ ID NO 78
<211> LENGTH: 49
<212> TYPE: PRT
<213> ORGANISM: Artificial sequence
<220> FEATURE:
<223> OTHER INFORMATION: Engineered ABD binding polypeptide

<400> SEQUENCE: 78

Lys Glu Leu Ser Ser Ala Leu Leu Glu Ile Ser His Leu Pro Asn Leu
1               5                   10                  15

Thr His Gln Gln Arg Ile Ala Phe Ile Val Lys Leu Asp Asp Asp Pro
            20                  25                  30

Ser Gln Ser Ser Glu Leu Leu Ala Glu Ala Lys Lys Leu Asn Asp Ala
        35                  40                  45

Gln

<210> SEQ ID NO 79
<211> LENGTH: 49
<212> TYPE: PRT
<213> ORGANISM: Artificial sequence
<220> FEATURE:
<223> OTHER INFORMATION: Engineered ABD binding polypeptide

<400> SEQUENCE: 79

```
Lys Glu Leu Val His Ala Phe Gly Glu Ile Arg Tyr Leu Pro Asn Leu
1               5                   10                  15

Thr His Ser Gln Arg Ile Ala Phe Ile Ile Lys Leu Asp Asp Asp Pro
                20                  25                  30

Ser Gln Ser Ser Glu Leu Leu Ala Glu Ala Lys Lys Leu Asn Asp Ala
        35                  40                  45

Gln
```

<210> SEQ ID NO 80
<211> LENGTH: 49
<212> TYPE: PRT
<213> ORGANISM: Artificial sequence
<220> FEATURE:
<223> OTHER INFORMATION: Engineered ABD binding polypeptide

<400> SEQUENCE: 80

```
Lys Glu Leu His Asn Ala Phe Ser Glu Ile Lys Gln Leu Pro Asn Leu
1               5                   10                  15

Thr Thr Gln Gln Arg Ile Ala Phe Ile Ile Lys Leu Asp Asp Asp Pro
                20                  25                  30

Ser Gln Ser Ser Glu Leu Leu Ala Glu Ala Lys Lys Leu Asn Asp Ala
        35                  40                  45

Gln
```

<210> SEQ ID NO 81
<211> LENGTH: 49
<212> TYPE: PRT
<213> ORGANISM: Artificial sequence
<220> FEATURE:
<223> OTHER INFORMATION: Engineered ABD binding polypeptide

<400> SEQUENCE: 81

```
Lys Glu Gly Val Asn Ala Phe Asn Glu Ile Lys Gly Leu Pro Asn Leu
1               5                   10                  15

Thr Phe His Gln Lys Ile Ala Phe Ile Val Lys Leu Asp Asp Asp Pro
                20                  25                  30

Ser Gln Ser Ser Glu Leu Leu Ala Glu Ala Lys Lys Leu Asn Asp Ala
        35                  40                  45

Gln
```

<210> SEQ ID NO 82
<211> LENGTH: 49
<212> TYPE: PRT
<213> ORGANISM: Artificial sequence
<220> FEATURE:
<223> OTHER INFORMATION: Engineered ABD binding polypeptide

<400> SEQUENCE: 82

```
Lys Glu Leu Lys Tyr Ala Leu Met Glu Ile Arg Tyr Leu Pro Asn Leu
1               5                   10                  15

Thr His Arg Gln Lys Ile Ala Phe Ile Leu Lys Leu Asp Asp Asp Pro
                20                  25                  30

Ser Gln Ser Ser Glu Leu Leu Ala Glu Ala Lys Lys Leu Asn Asp Ala
        35                  40                  45

Gln
```

<210> SEQ ID NO 83
<211> LENGTH: 49
<212> TYPE: PRT
<213> ORGANISM: Artificial sequence

```
<220> FEATURE:
<223> OTHER INFORMATION: Engineered ABD binding polypeptide

<400> SEQUENCE: 83

Lys Glu Leu Arg Trp Ala Val Ser Glu Ile Arg His Leu Pro Asn Leu
1               5                   10                  15

Thr Phe His Gln Arg Ile Ala Phe Ile Val Lys Leu Asp Asp Asp Pro
            20                  25                  30

Ser Gln Ser Ser Glu Leu Leu Ala Glu Ala Lys Lys Leu Asn Asp Ala
        35                  40                  45

Gln

<210> SEQ ID NO 84
<211> LENGTH: 49
<212> TYPE: PRT
<213> ORGANISM: Artificial sequence
<220> FEATURE:
<223> OTHER INFORMATION: Engineered ABD binding polypeptide

<400> SEQUENCE: 84

Lys Glu Leu Gln Arg Ala Phe Ala Glu Ile Gln Ser Leu Pro Asn Leu
1               5                   10                  15

Thr Leu Asn Gln His Ile Ala Phe Ile Tyr Lys Leu Glu Asp Asp Pro
            20                  25                  30

Ser Gln Ser Ser Glu Leu Leu Ala Glu Ala Lys Lys Leu Asn Asp Ala
        35                  40                  45

Gln

<210> SEQ ID NO 85
<211> LENGTH: 49
<212> TYPE: PRT
<213> ORGANISM: Artificial sequence
<220> FEATURE:
<223> OTHER INFORMATION: Engineered ABD binding polypeptide

<400> SEQUENCE: 85

Lys Glu Leu Lys Ala Ala Phe Arg Glu Ile Arg Thr Leu Pro Asn Leu
1               5                   10                  15

Thr Phe Gly Gln Arg Thr Ala Phe Ile Val Lys Leu Asp Asp Asp Pro
            20                  25                  30

Ser Gln Ser Ser Glu Leu Leu Ala Glu Ala Lys Lys Leu Asn Asp Ala
        35                  40                  45

Gln

<210> SEQ ID NO 86
<211> LENGTH: 49
<212> TYPE: PRT
<213> ORGANISM: Artificial sequence
<220> FEATURE:
<223> OTHER INFORMATION: Engineered ABD binding polypeptide

<400> SEQUENCE: 86

Lys Glu Leu Thr Thr Ala Met Lys Glu Ile Gln Ala Leu Pro Asn Leu
1               5                   10                  15

Thr His Gln Gln Arg Ile Ala Phe Ile Val Lys Leu Asp Asp Asp Pro
            20                  25                  30

Ser Gln Ser Ser Glu Leu Leu Ala Glu Ala Lys Lys Leu Asn Asp Ala
        35                  40                  45

Gln
```

```
<210> SEQ ID NO 87
<211> LENGTH: 49
<212> TYPE: PRT
<213> ORGANISM: Artificial sequence
<220> FEATURE:
<223> OTHER INFORMATION: Engineered ABD binding polypeptide

<400> SEQUENCE: 87

Lys Glu Asp Met Arg Ala Phe His Glu Ile Asn Lys Leu Pro Asn Leu
1               5                   10                  15

Thr Leu Ala Gln Arg Val Ala Phe Ile Tyr Lys Leu Glu Asp Asp Pro
            20                  25                  30

Ser Gln Ser Ser Glu Leu Leu Ala Glu Ala Lys Lys Leu Asn Asp Ala
        35                  40                  45

Gln

<210> SEQ ID NO 88
<211> LENGTH: 49
<212> TYPE: PRT
<213> ORGANISM: Artificial sequence
<220> FEATURE:
<223> OTHER INFORMATION: Engineered ABD binding polypeptide

<400> SEQUENCE: 88

Lys Glu Leu Asn Ala Ala Phe Thr Glu Ile Ser Ser Leu Pro Asn Leu
1               5                   10                  15

Thr Leu Asp Gln Arg Leu Ala Phe Ile Phe Lys Leu Asp Asp Asp Pro
            20                  25                  30

Ser Gln Ser Ser Glu Leu Leu Ala Glu Ala Lys Lys Leu Asn Asp Ala
        35                  40                  45

Gln

<210> SEQ ID NO 89
<211> LENGTH: 49
<212> TYPE: PRT
<213> ORGANISM: Artificial sequence
<220> FEATURE:
<223> OTHER INFORMATION: Engineered ABD binding polypeptide

<400> SEQUENCE: 89

Lys Glu Leu Arg Trp Ala Leu Asn Glu Ile His Ile Leu Pro Asn Leu
1               5                   10                  15

Thr Leu Glu Gln Lys Val Ala Phe Ile Val Lys Leu Asp Asp Asp Pro
            20                  25                  30

Ser Gln Ser Ser Glu Leu Leu Ala Glu Ala Lys Lys Leu Asn Asp Ala
        35                  40                  45

Gln

<210> SEQ ID NO 90
<211> LENGTH: 49
<212> TYPE: PRT
<213> ORGANISM: Artificial sequence
<220> FEATURE:
<223> OTHER INFORMATION: Engineered ABD binding polypeptide

<400> SEQUENCE: 90

Lys Glu Leu Lys Asn Ala Phe Ile Glu Ile Lys Asn Leu Pro Asn Leu
1               5                   10                  15

Thr Thr Asn Gln Thr Leu Ala Phe Ile Val Lys Leu Asp Asp Asp Pro
            20                  25                  30
```

```
Ser Gln Ser Ser Glu Leu Leu Ala Glu Ala Lys Lys Leu Asn Asp Ala
        35                  40                  45

Gln

<210> SEQ ID NO 91
<211> LENGTH: 49
<212> TYPE: PRT
<213> ORGANISM: Artificial sequence
<220> FEATURE:
<223> OTHER INFORMATION: Engineered ABD binding polypeptide

<400> SEQUENCE: 91

Lys Glu Leu Ser Leu Ala Phe Val Glu Ile His Lys Leu Pro Asn Leu
  1               5                  10                  15

Thr His His Gln Arg Leu Ala Phe Ile Val Lys Leu Asp Asp Asp Pro
             20                  25                  30

Ser Gln Ser Ser Glu Leu Leu Ala Glu Ala Lys Lys Leu Asn Asp Ala
        35                  40                  45

Gln

<210> SEQ ID NO 92
<211> LENGTH: 49
<212> TYPE: PRT
<213> ORGANISM: Artificial sequence
<220> FEATURE:
<223> OTHER INFORMATION: Engineered ABD binding polypeptide

<400> SEQUENCE: 92

Lys Glu Leu Gln Trp Ala Phe Asn Glu Ile His Asn Leu Pro Asn Leu
  1               5                  10                  15

Thr Tyr Val Gln Arg Ile Ala Phe Ile Val Lys Leu Asp Asp Asp Pro
             20                  25                  30

Ser Gln Ser Ser Glu Leu Leu Ala Glu Ala Lys Lys Leu Asn Asp Ala
        35                  40                  45

Gln

<210> SEQ ID NO 93
<211> LENGTH: 49
<212> TYPE: PRT
<213> ORGANISM: Artificial sequence
<220> FEATURE:
<223> OTHER INFORMATION: Engineered ABD binding polypeptide

<400> SEQUENCE: 93

Lys Glu Glu Gln Thr Ala Met Gln Glu Ile Asn Ser Leu Pro Asn Leu
  1               5                  10                  15

Thr Leu Glu Gln Arg Ile Ala Phe Ile Phe Lys Leu Glu Asp Asp Pro
             20                  25                  30

Ser Gln Ser Ser Glu Leu Leu Ala Glu Ala Lys Lys Leu Asn Asp Ala
        35                  40                  45

Gln

<210> SEQ ID NO 94
<211> LENGTH: 49
<212> TYPE: PRT
<213> ORGANISM: Artificial sequence
<220> FEATURE:
<223> OTHER INFORMATION: Engineered ABD binding polypeptide

<400> SEQUENCE: 94

Lys Glu Leu Gly Trp Ala Phe Arg Glu Ile Arg Asn Leu Pro Asn Leu
```

```
                1               5                  10                 15
Thr His Tyr Gln Arg Ile Ala Phe Ile Met Lys Leu Asp Asp Pro
                20                 25                 30

Ser Gln Ser Ser Glu Leu Leu Ala Glu Ala Lys Lys Leu Asn Asp Ala
        35                 40                 45

Gln

<210> SEQ ID NO 95
<211> LENGTH: 49
<212> TYPE: PRT
<213> ORGANISM: Artificial sequence
<220> FEATURE:
<223> OTHER INFORMATION: Engineered ABD binding polypeptide

<400> SEQUENCE: 95

Lys Glu Asn Leu Trp Ala Phe Asn Glu Ile Lys Gly Leu Pro Asn Leu
1               5                  10                 15

Thr His Asp Gln Arg Ile Ala Phe Ile Val Lys Leu Asp Asp Pro
                20                 25                 30

Ser Gln Ser Ser Glu Leu Leu Ala Glu Ala Lys Lys Leu Asn Asp Ala
        35                 40                 45

Gln

<210> SEQ ID NO 96
<211> LENGTH: 49
<212> TYPE: PRT
<213> ORGANISM: Artificial sequence
<220> FEATURE:
<223> OTHER INFORMATION: Engineered ABD binding polypeptide

<400> SEQUENCE: 96

Lys Glu Leu Ser Phe Ala Phe Ser Glu Ile Asn Val Leu Pro Asn Leu
1               5                  10                 15

Thr Phe His Gln Lys Ile Ala Phe Ile Tyr Lys Leu Glu Asp Asp Pro
                20                 25                 30

Ser Gln Ser Ser Glu Leu Leu Ala Glu Ala Lys Lys Leu Asn Asp Ala
        35                 40                 45

Gln

<210> SEQ ID NO 97
<211> LENGTH: 49
<212> TYPE: PRT
<213> ORGANISM: Artificial sequence
<220> FEATURE:
<223> OTHER INFORMATION: Engineered ABD binding polypeptide

<400> SEQUENCE: 97

Lys Glu Phe Arg Gly Ala Ile Ala Glu Ile Arg Asp Leu Pro Asn Leu
1               5                  10                 15

Thr Leu Glu Gln Lys Tyr Ala Phe Ile Phe Lys Leu Glu Asp Asp Pro
                20                 25                 30

Ser Gln Ser Ser Glu Leu Leu Ala Glu Ala Lys Lys Leu Asn Asp Ala
        35                 40                 45

Gln

<210> SEQ ID NO 98
<211> LENGTH: 49
<212> TYPE: PRT
<213> ORGANISM: Artificial sequence
<220> FEATURE:
```

<223> OTHER INFORMATION: Engineered ABD binding polypeptide

<400> SEQUENCE: 98

Lys Glu Glu Glu Asn Ala Tyr Lys Glu Ile Gly Ser Leu Pro Asn Leu
1               5                   10                  15

Thr Leu Ala Gln Lys Val Ala Phe Ile Leu Lys Leu Glu Asp Asp Pro
            20                  25                  30

Ser Gln Ser Ser Glu Leu Leu Ala Glu Ala Lys Lys Leu Asn Asp Ala
        35                  40                  45

Gln

<210> SEQ ID NO 99
<211> LENGTH: 49
<212> TYPE: PRT
<213> ORGANISM: Artificial sequence
<220> FEATURE:
<223> OTHER INFORMATION: Engineered ABD binding polypeptide

<400> SEQUENCE: 99

Lys Glu Leu Arg Gln Ala Leu Gln Glu Ile His Ile Leu Pro Asn Leu
1               5                   10                  15

Thr His Ser Gln Arg Val Ala Phe Ile Val Lys Leu Asp Asp Asp Pro
            20                  25                  30

Ser Gln Ser Ser Glu Leu Leu Ala Glu Ala Lys Lys Leu Asn Asp Ala
        35                  40                  45

Gln

<210> SEQ ID NO 100
<211> LENGTH: 49
<212> TYPE: PRT
<213> ORGANISM: Artificial sequence
<220> FEATURE:
<223> OTHER INFORMATION: Engineered ABD binding polypeptide

<400> SEQUENCE: 100

Lys Glu Asn His Ala Ala Phe Gln Glu Ile Leu Ser Leu Pro Asn Leu
1               5                   10                  15

Thr Leu Asn Gln Arg Leu Ala Phe Ile Thr Lys Leu Asp Asp Asp Pro
            20                  25                  30

Ser Gln Ser Ser Glu Leu Leu Ala Glu Ala Lys Lys Leu Asn Asp Ala
        35                  40                  45

Gln

<210> SEQ ID NO 101
<211> LENGTH: 49
<212> TYPE: PRT
<213> ORGANISM: Artificial sequence
<220> FEATURE:
<223> OTHER INFORMATION: Engineered ABD binding polypeptide

<400> SEQUENCE: 101

Lys Glu Thr Asn Tyr Ala Phe Lys Glu Ile Asp Leu Leu Pro Asn Leu
1               5                   10                  15

Thr Leu Met Gln Lys Leu Ala Phe Ile Val Lys Leu Asp Asp Asp Pro
            20                  25                  30

Ser Gln Ser Ser Glu Leu Leu Ala Glu Ala Lys Lys Leu Asn Asp Ala
        35                  40                  45

Gln

```
<210> SEQ ID NO 102
<211> LENGTH: 49
<212> TYPE: PRT
<213> ORGANISM: Artificial sequence
<220> FEATURE:
<223> OTHER INFORMATION: Engineered ABD binding polypeptide

<400> SEQUENCE: 102

Lys Glu Ile Ser Leu Ala Phe Lys Glu Ile Lys Ala Leu Pro Asn Leu
1               5                   10                  15

Thr Gly Gln Gln Arg Phe Ala Phe Ile Leu Lys Leu Asp Asp Asp Pro
            20                  25                  30

Ser Gln Ser Ser Glu Leu Leu Ala Glu Ala Lys Lys Leu Asn Asp Ala
        35                  40                  45

Gln

<210> SEQ ID NO 103
<211> LENGTH: 49
<212> TYPE: PRT
<213> ORGANISM: Artificial sequence
<220> FEATURE:
<223> OTHER INFORMATION: Engineered ABD binding polypeptide

<400> SEQUENCE: 103

Lys Glu Leu Ser Lys Ala Leu Thr Glu Ile Arg Met Leu Pro Asn Leu
1               5                   10                  15

Thr Phe Arg Gln Arg Ile Ala Phe Ile Ile Lys Leu Asp Asp Asp Pro
            20                  25                  30

Ser Gln Ser Ser Glu Leu Leu Ala Glu Ala Lys Lys Leu Asn Asp Ala
        35                  40                  45

Gln

<210> SEQ ID NO 104
<211> LENGTH: 49
<212> TYPE: PRT
<213> ORGANISM: Artificial sequence
<220> FEATURE:
<223> OTHER INFORMATION: Engineered ABD binding polypeptide

<400> SEQUENCE: 104

Lys Glu Leu Asp Met Ala Tyr Thr Glu Ile Gly Leu Leu Pro Asn Leu
1               5                   10                  15

Thr Phe Ser Gln Leu Leu Ala Phe Ile Ile Lys Leu Asp Asp Asp Pro
            20                  25                  30

Ser Gln Ser Ser Glu Leu Leu Ala Glu Ala Lys Lys Leu Asn Asp Ala
        35                  40                  45

Gln

<210> SEQ ID NO 105
<211> LENGTH: 58
<212> TYPE: PRT
<213> ORGANISM: Artificial sequence
<220> FEATURE:
<223> OTHER INFORMATION: Engineered ABD binding polypeptide

<400> SEQUENCE: 105

Val Asp Ala Lys Tyr Ala Lys Glu Leu Lys Val Ala Phe Lys Glu Ile
1               5                   10                  15

Asn Thr Leu Pro Asn Leu Thr His Gln Gln Arg Ile Ala Phe Ile Ile
            20                  25                  30

Lys Leu Asp Asp Asp Pro Ser Gln Ser Ser Glu Leu Leu Ala Glu Ala
```

-continued

```
                35                  40                  45
Lys Lys Leu Asn Asp Ala Gln Ala Pro Lys
    50                  55

<210> SEQ ID NO 106
<211> LENGTH: 58
<212> TYPE: PRT
<213> ORGANISM: Artificial sequence
<220> FEATURE:
<223> OTHER INFORMATION: Engineered ABD binding polypeptide

<400> SEQUENCE: 106

Val Asp Ala Lys Tyr Ala Lys Glu Leu Val Asn Ala Phe Ser Glu Ile
1               5                   10                  15

Lys Ala Leu Pro Asn Leu Thr Leu His Gln Arg Leu Ala Phe Ile Val
            20                  25                  30

Lys Leu Asp Asp Asp Pro Ser Gln Ser Ser Glu Leu Leu Ala Glu Ala
        35                  40                  45

Lys Lys Leu Asn Asp Ala Gln Ala Pro Lys
    50                  55

<210> SEQ ID NO 107
<211> LENGTH: 58
<212> TYPE: PRT
<213> ORGANISM: Artificial sequence
<220> FEATURE:
<223> OTHER INFORMATION: Engineered ABD binding polypeptide

<400> SEQUENCE: 107

Val Asp Ala Lys Tyr Ala Lys Glu Leu His His Ala Phe Arg Glu Ile
1               5                   10                  15

Lys Phe Leu Pro Asn Leu Thr Phe His Gln Arg Leu Ala Phe Ile Val
            20                  25                  30

Lys Leu Asp Asp Asp Pro Ser Gln Ser Ser Glu Leu Leu Ala Glu Ala
        35                  40                  45

Lys Lys Leu Asn Asp Ala Gln Ala Pro Lys
    50                  55

<210> SEQ ID NO 108
<211> LENGTH: 58
<212> TYPE: PRT
<213> ORGANISM: Artificial sequence
<220> FEATURE:
<223> OTHER INFORMATION: Engineered ABD binding polypeptide

<400> SEQUENCE: 108

Val Asp Ala Lys Tyr Ala Lys Glu Phe Lys Leu Ala Leu Gln Glu Ile
1               5                   10                  15

His Tyr Leu Pro Asn Leu Thr Leu Asp Gln Arg Leu Ala Phe Ile Leu
            20                  25                  30

Lys Leu Asp Asp Asp Pro Ser Gln Ser Ser Glu Leu Leu Ala Glu Ala
        35                  40                  45

Lys Lys Leu Asn Asp Ala Gln Ala Pro Lys
    50                  55

<210> SEQ ID NO 109
<211> LENGTH: 58
<212> TYPE: PRT
<213> ORGANISM: Artificial sequence
<220> FEATURE:
<223> OTHER INFORMATION: Engineered ABD binding polypeptide
```

```
<400> SEQUENCE: 109

Val Asp Ala Lys Tyr Ala Lys Glu Leu Arg Trp Ala Leu Asn Glu Ile
1               5                   10                  15

Arg Arg Leu Pro Asn Leu Thr Phe Lys Gln His Ile Ala Phe Ile Val
                20                  25                  30

Lys Leu Asp Asp Pro Ser Gln Ser Ser Glu Leu Leu Ala Glu Ala
            35                  40                  45

Lys Lys Leu Asn Asp Ala Gln Ala Pro Lys
    50                  55

<210> SEQ ID NO 110
<211> LENGTH: 58
<212> TYPE: PRT
<213> ORGANISM: Artificial sequence
<220> FEATURE:
<223> OTHER INFORMATION: Engineered ABD binding polypeptide

<400> SEQUENCE: 110

Val Asp Ala Lys Tyr Ala Lys Glu Phe Arg Ala Ala Leu Leu Glu Ile
1               5                   10                  15

Lys Leu Leu Pro Asn Leu Thr Phe Ile Gln Arg Leu Ala Phe Ile Val
                20                  25                  30

Lys Leu Asp Asp Pro Ser Gln Ser Ser Glu Leu Leu Ala Glu Ala
            35                  40                  45

Lys Lys Leu Asn Asp Ala Gln Ala Pro Lys
    50                  55

<210> SEQ ID NO 111
<211> LENGTH: 58
<212> TYPE: PRT
<213> ORGANISM: Artificial sequence
<220> FEATURE:
<223> OTHER INFORMATION: Engineered ABD binding polypeptide

<400> SEQUENCE: 111

Val Asp Ala Lys Tyr Ala Lys Glu Phe Thr Ile Ala Leu Arg Glu Ile
1               5                   10                  15

His Ala Leu Pro Asn Leu Thr Leu His Gln Arg Leu Ala Phe Ile Ile
                20                  25                  30

Lys Leu Asp Asp Pro Ser Gln Ser Ser Glu Leu Leu Ala Glu Ala
            35                  40                  45

Lys Lys Leu Asn Asp Ala Gln Ala Pro Lys
    50                  55

<210> SEQ ID NO 112
<211> LENGTH: 58
<212> TYPE: PRT
<213> ORGANISM: Artificial sequence
<220> FEATURE:
<223> OTHER INFORMATION: Engineered ABD binding polypeptide

<400> SEQUENCE: 112

Val Asp Ala Lys Tyr Ala Lys Glu Leu Arg Lys Ala Phe His Glu Ile
1               5                   10                  15

Gln Ile Leu Pro Asn Leu Thr Leu Ser Gln Arg Leu Ala Phe Ile Val
                20                  25                  30

Lys Leu Asp Asp Pro Ser Gln Ser Ser Glu Leu Leu Ala Glu Ala
            35                  40                  45

Lys Lys Leu Asn Asp Ala Gln Ala Pro Lys
    50                  55
```

<210> SEQ ID NO 113
<211> LENGTH: 58
<212> TYPE: PRT
<213> ORGANISM: Artificial sequence
<220> FEATURE:
<223> OTHER INFORMATION: Engineered ABD binding polypeptide

<400> SEQUENCE: 113

Val Asp Ala Lys Tyr Ala Lys Glu Phe Lys Asp Ala Leu Asp Glu Ile
1               5                   10                  15

Lys Asp Leu Pro Asn Leu Thr Ser Met Gln Arg Ile Ala Phe Ile Val
            20                  25                  30

Lys Leu Asp Asp Asp Pro Ser Gln Ser Ser Glu Leu Leu Ala Glu Ala
        35                  40                  45

Lys Lys Leu Asn Asp Ala Gln Ala Pro Lys
        50                  55

<210> SEQ ID NO 114
<211> LENGTH: 58
<212> TYPE: PRT
<213> ORGANISM: Artificial sequence
<220> FEATURE:
<223> OTHER INFORMATION: Engineered ABD binding polypeptide

<400> SEQUENCE: 114

Val Asp Ala Lys Tyr Ala Lys Glu Leu Thr Thr Ala Phe Ala Glu Ile
1               5                   10                  15

Gln Lys Leu Pro Asn Leu Thr Phe Glu Gln Lys Ile Ala Phe Ile Ile
            20                  25                  30

Lys Leu Asp Asp Asp Pro Ser Gln Ser Ser Glu Leu Leu Ala Glu Ala
        35                  40                  45

Lys Lys Leu Asn Asp Ala Gln Ala Pro Lys
        50                  55

<210> SEQ ID NO 115
<211> LENGTH: 58
<212> TYPE: PRT
<213> ORGANISM: Artificial sequence
<220> FEATURE:
<223> OTHER INFORMATION: Engineered ABD binding polypeptide

<400> SEQUENCE: 115

Val Asp Ala Lys Tyr Ala Lys Glu Phe Arg Glu Ala Ile Ile Glu Ile
1               5                   10                  15

Arg Arg Leu Pro Asn Leu Thr Leu His Gln Arg Leu Ala Phe Ile Met
            20                  25                  30

Lys Leu Asp Asp Asp Pro Ser Gln Ser Ser Glu Leu Leu Ala Glu Ala
        35                  40                  45

Lys Lys Leu Asn Asp Ala Gln Ala Pro Lys
        50                  55

<210> SEQ ID NO 116
<211> LENGTH: 58
<212> TYPE: PRT
<213> ORGANISM: Artificial sequence
<220> FEATURE:
<223> OTHER INFORMATION: Engineered ABD binding polypeptide

<400> SEQUENCE: 116

Val Asp Ala Lys Tyr Ala Lys Glu Ile Lys Thr Ala Phe Ala Glu Ile
1               5                   10                  15

```
Arg Val Leu Pro Asn Leu Thr Phe Ala Gln Arg Leu Ala Phe Ile Ile
            20                  25                  30

Lys Leu Asp Asp Asp Pro Ser Gln Ser Ser Glu Leu Leu Ala Glu Ala
        35                  40                  45

Lys Lys Leu Asn Asp Ala Gln Ala Pro Lys
    50                  55
```

<210> SEQ ID NO 117
<211> LENGTH: 58
<212> TYPE: PRT
<213> ORGANISM: Artificial sequence
<220> FEATURE:
<223> OTHER INFORMATION: Engineered ABD binding polypeptide

<400> SEQUENCE: 117

```
Val Asp Ala Lys Tyr Ala Lys Glu Arg Arg Tyr Ala Phe Arg Glu Ile
1               5                   10                  15

Arg Leu Leu Pro Asn Leu Thr Phe Ser Gln Arg Ile Ala Phe Ile Val
            20                  25                  30

Lys Leu Asp Asp Asp Pro Ser Gln Ser Ser Glu Leu Leu Ala Glu Ala
        35                  40                  45

Lys Lys Leu Asn Asp Ala Gln Ala Pro Lys
    50                  55
```

<210> SEQ ID NO 118
<211> LENGTH: 58
<212> TYPE: PRT
<213> ORGANISM: Artificial sequence
<220> FEATURE:
<223> OTHER INFORMATION: Engineered ABD binding polypeptide

<400> SEQUENCE: 118

```
Val Asp Ala Lys Tyr Ala Lys Glu Leu Lys Ala Ala Phe Arg Glu Ile
1               5                   10                  15

Asn Asp Leu Pro Asn Leu Thr His Thr Gln Arg Ile Ala Phe Ile Leu
            20                  25                  30

Lys Leu Asp Asp Asp Pro Ser Gln Ser Ser Glu Leu Leu Ala Glu Ala
        35                  40                  45

Lys Lys Leu Asn Asp Ala Gln Ala Pro Lys
    50                  55
```

<210> SEQ ID NO 119
<211> LENGTH: 58
<212> TYPE: PRT
<213> ORGANISM: Artificial sequence
<220> FEATURE:
<223> OTHER INFORMATION: Engineered ABD binding polypeptide

<400> SEQUENCE: 119

```
Val Asp Ala Lys Tyr Ala Lys Glu Leu Lys Met Ala Phe Gln Glu Ile
1               5                   10                  15

Arg Tyr Leu Pro Asn Leu Thr Arg Leu Gln Arg Ile Ala Phe Ile Val
            20                  25                  30

Lys Leu Asp Asp Asp Pro Ser Gln Ser Ser Glu Leu Leu Ala Glu Ala
        35                  40                  45

Lys Lys Leu Asn Asp Ala Gln Ala Pro Lys
    50                  55
```

<210> SEQ ID NO 120
<211> LENGTH: 58

```
<212> TYPE: PRT
<213> ORGANISM: Artificial sequence
<220> FEATURE:
<223> OTHER INFORMATION: Engineered ABD binding polypeptide

<400> SEQUENCE: 120

Val Asp Ala Lys Tyr Ala Lys Glu Trp Lys Lys Ala Leu Arg Glu Ile
1               5                   10                  15

His Tyr Leu Pro Asn Leu Thr Leu Thr Gln Arg Leu Ala Phe Ile Val
            20                  25                  30

Lys Leu Asp Asp Asp Pro Ser Gln Ser Ser Glu Leu Leu Ala Glu Ala
        35                  40                  45

Lys Lys Leu Asn Asp Ala Gln Ala Pro Lys
    50                  55

<210> SEQ ID NO 121
<211> LENGTH: 58
<212> TYPE: PRT
<213> ORGANISM: Artificial sequence
<220> FEATURE:
<223> OTHER INFORMATION: Engineered ABD binding polypeptide

<400> SEQUENCE: 121

Val Asp Ala Lys Tyr Ala Lys Glu Phe Glu Lys Ala Leu Val Glu Ile
1               5                   10                  15

Lys Thr Leu Pro Asn Leu Thr Ala Ile Gln Arg Ile Ala Phe Ile Val
            20                  25                  30

Lys Leu Asp Asp Asp Pro Ser Gln Ser Ser Glu Leu Leu Ala Glu Ala
        35                  40                  45

Lys Lys Leu Asn Asp Ala Gln Ala Pro Lys
    50                  55

<210> SEQ ID NO 122
<211> LENGTH: 58
<212> TYPE: PRT
<213> ORGANISM: Artificial sequence
<220> FEATURE:
<223> OTHER INFORMATION: Engineered ABD binding polypeptide

<400> SEQUENCE: 122

Val Asp Ala Lys Tyr Ala Lys Glu Phe Ile Phe Ala Leu Ser Glu Ile
1               5                   10                  15

Lys Val Leu Pro Asn Leu Thr His Val Gln Lys Ile Ala Phe Ile Val
            20                  25                  30

Lys Leu Asp Asp Asp Pro Ser Gln Ser Ser Glu Leu Leu Ala Glu Ala
        35                  40                  45

Lys Lys Leu Asn Asp Ala Gln Ala Pro Lys
    50                  55

<210> SEQ ID NO 123
<211> LENGTH: 58
<212> TYPE: PRT
<213> ORGANISM: Artificial sequence
<220> FEATURE:
<223> OTHER INFORMATION: Engineered ABD binding polypeptide

<400> SEQUENCE: 123

Val Asp Ala Lys Tyr Ala Lys Glu Phe Lys Tyr Ala Ile Gln Glu Ile
1               5                   10                  15

Lys Asp Leu Pro Asn Leu Thr Ser Gly Gln Arg Ile Ala Phe Ile Val
            20                  25                  30
```

Lys Leu Asp Asp Asp Pro Ser Gln Ser Ser Glu Leu Leu Ala Glu Ala
        35                  40                  45
Lys Lys Leu Asn Asp Ala Gln Ala Pro Lys
    50                  55

<210> SEQ ID NO 124
<211> LENGTH: 58
<212> TYPE: PRT
<213> ORGANISM: Artificial sequence
<220> FEATURE:
<223> OTHER INFORMATION: Engineered ABD binding polypeptide

<400> SEQUENCE: 124

Val Asp Ala Lys Tyr Ala Lys Glu Leu Asn Gln Ala Leu Trp Glu Ile
1               5                   10                  15
Arg Gln Leu Pro Asn Leu Thr Phe Asn Gln Arg Val Ala Phe Ile Val
            20                  25                  30
Lys Leu Asp Asp Asp Pro Ser Gln Ser Ser Glu Leu Leu Ala Glu Ala
        35                  40                  45
Lys Lys Leu Asn Asp Ala Gln Ala Pro Lys
    50                  55

<210> SEQ ID NO 125
<211> LENGTH: 58
<212> TYPE: PRT
<213> ORGANISM: Artificial sequence
<220> FEATURE:
<223> OTHER INFORMATION: Engineered ABD binding polypeptide

<400> SEQUENCE: 125

Val Asp Ala Lys Tyr Ala Lys Glu Leu Gln Gly Ala Leu Thr Glu Ile
1               5                   10                  15
Lys Asn Leu Pro Asn Leu Thr Gly His Gln Arg Ile Ala Phe Ile Val
            20                  25                  30
Lys Leu Asp Asp Asp Pro Ser Gln Ser Ser Glu Leu Leu Ala Glu Ala
        35                  40                  45
Lys Lys Leu Asn Asp Ala Gln Ala Pro Lys
    50                  55

<210> SEQ ID NO 126
<211> LENGTH: 58
<212> TYPE: PRT
<213> ORGANISM: Artificial sequence
<220> FEATURE:
<223> OTHER INFORMATION: Engineered ABD binding polypeptide

<400> SEQUENCE: 126

Val Asp Ala Lys Tyr Ala Lys Glu Leu Ala Asp Ala Leu Tyr Glu Ile
1               5                   10                  15
Lys Asn Leu Pro Asn Leu Thr His Glu Gln His Ile Ala Phe Ile Val
            20                  25                  30
Lys Leu Asp Asp Asp Pro Ser Gln Ser Ser Glu Leu Leu Ala Glu Ala
        35                  40                  45
Lys Lys Leu Asn Asp Ala Gln Ala Pro Lys
    50                  55

<210> SEQ ID NO 127
<211> LENGTH: 58
<212> TYPE: PRT
<213> ORGANISM: Artificial sequence
<220> FEATURE:
<223> OTHER INFORMATION: Engineered ABD binding polypeptide -continued

<400> SEQUENCE: 127

Val Asp Ala Lys Tyr Ala Lys Glu Leu Gly Val Ala Leu Lys Glu Ile
1               5                   10                  15

Gly Gln Leu Pro Asn Leu Thr His Thr Gln Arg Ile Ala Phe Ile Ile
            20                  25                  30

Lys Leu Asp Asp Pro Ser Gln Ser Ser Glu Leu Leu Ala Glu Ala
        35                  40                  45

Lys Lys Leu Asn Asp Ala Gln Ala Pro Lys
    50                  55

<210> SEQ ID NO 128
<211> LENGTH: 58
<212> TYPE: PRT
<213> ORGANISM: Artificial sequence
<220> FEATURE:
<223> OTHER INFORMATION: Engineered ABD binding polypeptide

<400> SEQUENCE: 128

Val Asp Ala Lys Tyr Ala Lys Glu Leu Ser Ile Ala Leu Asn Glu Ile
1               5                   10                  15

Lys Gly Leu Pro Asn Leu Thr Ser Leu Gln Lys Ile Ala Phe Ile Val
            20                  25                  30

Lys Leu Asp Asp Pro Ser Gln Ser Ser Glu Leu Leu Ala Glu Ala
        35                  40                  45

Lys Lys Leu Asn Asp Ala Gln Ala Pro Lys
    50                  55

<210> SEQ ID NO 129
<211> LENGTH: 58
<212> TYPE: PRT
<213> ORGANISM: Artificial sequence
<220> FEATURE:
<223> OTHER INFORMATION: Engineered ABD binding polypeptide

<400> SEQUENCE: 129

Val Asp Ala Lys Tyr Ala Lys Glu Ile Arg Ser Ala Tyr Lys Glu Ile
1               5                   10                  15

Asn Val Leu Pro Asn Leu Thr Phe Ser Gln Lys Ile Ala Phe Ile Tyr
            20                  25                  30

Lys Leu Glu Asp Pro Ser Gln Ser Ser Glu Leu Leu Ala Glu Ala
        35                  40                  45

Lys Lys Leu Asn Asp Ala Gln Ala Pro Lys
    50                  55

<210> SEQ ID NO 130
<211> LENGTH: 58
<212> TYPE: PRT
<213> ORGANISM: Artificial sequence
<220> FEATURE:
<223> OTHER INFORMATION: Engineered ABD binding polypeptide

<400> SEQUENCE: 130

Val Asp Ala Lys Tyr Ala Lys Glu Leu Ser Ser Ala Leu Leu Glu Ile
1               5                   10                  15

Ser His Leu Pro Asn Leu Thr His Gln Gln Arg Ile Ala Phe Ile Val
            20                  25                  30

Lys Leu Asp Asp Pro Ser Gln Ser Ser Glu Leu Leu Ala Glu Ala
        35                  40                  45

Lys Lys Leu Asn Asp Ala Gln Ala Pro Lys

-continued

```
              50                  55

<210> SEQ ID NO 131
<211> LENGTH: 58
<212> TYPE: PRT
<213> ORGANISM: Artificial sequence
<220> FEATURE:
<223> OTHER INFORMATION: Engineered ABD binding polypeptide

<400> SEQUENCE: 131

Val Asp Ala Lys Tyr Ala Lys Glu Leu Val His Ala Phe Gly Glu Ile
1               5                   10                  15

Arg Tyr Leu Pro Asn Leu Thr His Ser Gln Arg Ile Ala Phe Ile Ile
            20                  25                  30

Lys Leu Asp Asp Asp Pro Ser Gln Ser Ser Glu Leu Leu Ala Glu Ala
        35                  40                  45

Lys Lys Leu Asn Asp Ala Gln Ala Pro Lys
    50                  55

<210> SEQ ID NO 132
<211> LENGTH: 58
<212> TYPE: PRT
<213> ORGANISM: Artificial sequence
<220> FEATURE:
<223> OTHER INFORMATION: Engineered ABD binding polypeptide

<400> SEQUENCE: 132

Val Asp Ala Lys Tyr Ala Lys Glu Leu His Asn Ala Phe Ser Glu Ile
1               5                   10                  15

Lys Gln Leu Pro Asn Leu Thr Thr Gln Gln Arg Ile Ala Phe Ile Ile
            20                  25                  30

Lys Leu Asp Asp Asp Pro Ser Gln Ser Ser Glu Leu Leu Ala Glu Ala
        35                  40                  45

Lys Lys Leu Asn Asp Ala Gln Ala Pro Lys
50                  55

<210> SEQ ID NO 133
<211> LENGTH: 58
<212> TYPE: PRT
<213> ORGANISM: Artificial sequence
<220> FEATURE:
<223> OTHER INFORMATION: Engineered ABD binding polypeptide

<400> SEQUENCE: 133

Val Asp Ala Lys Tyr Ala Lys Glu Gly Val Asn Ala Phe Asn Glu Ile
1               5                   10                  15

Lys Gly Leu Pro Asn Leu Thr Phe His Gln Lys Ile Ala Phe Ile Val
            20                  25                  30

Lys Leu Asp Asp Asp Pro Ser Gln Ser Ser Glu Leu Leu Ala Glu Ala
        35                  40                  45

Lys Lys Leu Asn Asp Ala Gln Ala Pro Lys
    50                  55

<210> SEQ ID NO 134
<211> LENGTH: 58
<212> TYPE: PRT
<213> ORGANISM: Artificial sequence
<220> FEATURE:
<223> OTHER INFORMATION: Engineered ABD binding polypeptide

<400> SEQUENCE: 134

Val Asp Ala Lys Tyr Ala Lys Glu Leu Lys Tyr Ala Leu Met Glu Ile
```

```
                1               5                  10                  15
Arg Tyr Leu Pro Asn Leu Thr His Arg Gln Lys Ile Ala Phe Ile Leu
                20                  25                  30
Lys Leu Asp Asp Pro Ser Gln Ser Ser Glu Leu Leu Ala Glu Ala
            35                  40                  45
Lys Lys Leu Asn Asp Ala Gln Ala Pro Lys
        50                  55
```

<210> SEQ ID NO 135
<211> LENGTH: 58
<212> TYPE: PRT
<213> ORGANISM: Artificial sequence
<220> FEATURE:
<223> OTHER INFORMATION: Engineered ABD binding polypeptide

<400> SEQUENCE: 135

```
Val Asp Ala Lys Tyr Ala Lys Glu Leu Arg Trp Ala Val Ser Glu Ile
1               5                   10                  15
Arg His Leu Pro Asn Leu Thr Phe His Gln Arg Ile Ala Phe Ile Val
                20                  25                  30
Lys Leu Asp Asp Pro Ser Gln Ser Ser Glu Leu Leu Ala Glu Ala
            35                  40                  45
Lys Lys Leu Asn Asp Ala Gln Ala Pro Lys
        50                  55
```

<210> SEQ ID NO 136
<211> LENGTH: 58
<212> TYPE: PRT
<213> ORGANISM: Artificial sequence
<220> FEATURE:
<223> OTHER INFORMATION: Engineered ABD binding polypeptide

<400> SEQUENCE: 136

```
Val Asp Ala Lys Tyr Ala Lys Glu Leu Gln Arg Ala Phe Ala Glu Ile
1               5                   10                  15
Gln Ser Leu Pro Asn Leu Thr Leu Asn Gln His Ile Ala Phe Ile Tyr
                20                  25                  30
Lys Leu Glu Asp Pro Ser Gln Ser Ser Glu Leu Leu Ala Glu Ala
            35                  40                  45
Lys Lys Leu Asn Asp Ala Gln Ala Pro Lys
        50                  55
```

<210> SEQ ID NO 137
<211> LENGTH: 58
<212> TYPE: PRT
<213> ORGANISM: Artificial sequence
<220> FEATURE:
<223> OTHER INFORMATION: Engineered ABD binding polypeptide

<400> SEQUENCE: 137

```
Val Asp Ala Lys Tyr Ala Lys Glu Leu Lys Ala Ala Phe Arg Glu Ile
1               5                   10                  15
Arg Thr Leu Pro Asn Leu Thr Phe Gly Gln Arg Thr Ala Phe Ile Val
                20                  25                  30
Lys Leu Asp Asp Pro Ser Gln Ser Ser Glu Leu Leu Ala Glu Ala
            35                  40                  45
Lys Lys Leu Asn Asp Ala Gln Ala Pro Lys
        50                  55
```

<210> SEQ ID NO 138

```
<211> LENGTH: 58
<212> TYPE: PRT
<213> ORGANISM: Artificial sequence
<220> FEATURE:
<223> OTHER INFORMATION: Engineered ABD binding polypeptide

<400> SEQUENCE: 138

Val Asp Ala Lys Tyr Ala Lys Glu Leu Thr Thr Ala Met Lys Glu Ile
1               5                   10                  15

Gln Ala Leu Pro Asn Leu Thr His Gln Gln Arg Ile Ala Phe Ile Val
            20                  25                  30

Lys Leu Asp Asp Asp Pro Ser Gln Ser Ser Glu Leu Leu Ala Glu Ala
        35                  40                  45

Lys Lys Leu Asn Asp Ala Gln Ala Pro Lys
    50                  55

<210> SEQ ID NO 139
<211> LENGTH: 58
<212> TYPE: PRT
<213> ORGANISM: Artificial sequence
<220> FEATURE:
<223> OTHER INFORMATION: Engineered ABD binding polypeptide

<400> SEQUENCE: 139

Val Asp Ala Lys Tyr Ala Lys Glu Asp Met Arg Ala Phe His Glu Ile
1               5                   10                  15

Asn Lys Leu Pro Asn Leu Thr Leu Ala Gln Arg Val Ala Phe Ile Tyr
            20                  25                  30

Lys Leu Glu Asp Asp Pro Ser Gln Ser Ser Glu Leu Leu Ala Glu Ala
        35                  40                  45

Lys Lys Leu Asn Asp Ala Gln Ala Pro Lys
    50                  55

<210> SEQ ID NO 140
<211> LENGTH: 58
<212> TYPE: PRT
<213> ORGANISM: Artificial sequence
<220> FEATURE:
<223> OTHER INFORMATION: Engineered ABD binding polypeptide

<400> SEQUENCE: 140

Val Asp Ala Lys Tyr Ala Lys Glu Leu Asn Ala Ala Phe Thr Glu Ile
1               5                   10                  15

Ser Ser Leu Pro Asn Leu Thr Leu Asp Gln Arg Leu Ala Phe Ile Phe
            20                  25                  30

Lys Leu Asp Asp Asp Pro Ser Gln Ser Ser Glu Leu Leu Ala Glu Ala
        35                  40                  45

Lys Lys Leu Asn Asp Ala Gln Ala Pro Lys
    50                  55

<210> SEQ ID NO 141
<211> LENGTH: 58
<212> TYPE: PRT
<213> ORGANISM: Artificial sequence
<220> FEATURE:
<223> OTHER INFORMATION: Engineered ABD binding polypeptide

<400> SEQUENCE: 141

Val Asp Ala Lys Tyr Ala Lys Glu Leu Arg Trp Ala Leu Asn Glu Ile
1               5                   10                  15

His Ile Leu Pro Asn Leu Thr Leu Glu Gln Lys Val Ala Phe Ile Val
            20                  25                  30
```

-continued

Lys Leu Asp Asp Asp Pro Ser Gln Ser Ser Glu Leu Leu Ala Glu Ala
        35                  40                  45

Lys Lys Leu Asn Asp Ala Gln Ala Pro Lys
    50                  55

<210> SEQ ID NO 142
<211> LENGTH: 58
<212> TYPE: PRT
<213> ORGANISM: Artificial sequence
<220> FEATURE:
<223> OTHER INFORMATION: Engineered ABD binding polypeptide

<400> SEQUENCE: 142

Val Asp Ala Lys Tyr Ala Lys Glu Leu Lys Asn Ala Phe Ile Glu Ile
1               5                   10                  15

Lys Asn Leu Pro Asn Leu Thr Thr Asn Gln Thr Leu Ala Phe Ile Val
            20                  25                  30

Lys Leu Asp Asp Asp Pro Ser Gln Ser Ser Glu Leu Leu Ala Glu Ala
        35                  40                  45

Lys Lys Leu Asn Asp Ala Gln Ala Pro Lys
    50                  55

<210> SEQ ID NO 143
<211> LENGTH: 58
<212> TYPE: PRT
<213> ORGANISM: Artificial sequence
<220> FEATURE:
<223> OTHER INFORMATION: Engineered ABD binding polypeptide

<400> SEQUENCE: 143

Val Asp Ala Lys Tyr Ala Lys Glu Leu Ser Leu Ala Phe Val Glu Ile
1               5                   10                  15

His Lys Leu Pro Asn Leu Thr His His Gln Arg Leu Ala Phe Ile Val
            20                  25                  30

Lys Leu Asp Asp Asp Pro Ser Gln Ser Ser Glu Leu Leu Ala Glu Ala
        35                  40                  45

Lys Lys Leu Asn Asp Ala Gln Ala Pro Lys
    50                  55

<210> SEQ ID NO 144
<211> LENGTH: 58
<212> TYPE: PRT
<213> ORGANISM: Artificial sequence
<220> FEATURE:
<223> OTHER INFORMATION: Engineered ABD binding polypeptide

<400> SEQUENCE: 144

Val Asp Ala Lys Tyr Ala Lys Glu Leu Gln Trp Ala Phe Asn Glu Ile
1               5                   10                  15

His Asn Leu Pro Asn Leu Thr Tyr Val Gln Arg Ile Ala Phe Ile Val
            20                  25                  30

Lys Leu Asp Asp Asp Pro Ser Gln Ser Ser Glu Leu Leu Ala Glu Ala
        35                  40                  45

Lys Lys Leu Asn Asp Ala Gln Ala Pro Lys
    50                  55

<210> SEQ ID NO 145
<211> LENGTH: 58
<212> TYPE: PRT
<213> ORGANISM: Artificial sequence
<220> FEATURE:

<223> OTHER INFORMATION: Engineered ABD binding polypeptide

<400> SEQUENCE: 145

Val Asp Ala Lys Tyr Ala Lys Glu Glu Gln Thr Ala Met Gln Glu Ile
1               5                   10                  15

Asn Ser Leu Pro Asn Leu Thr Leu Gln Arg Ile Ala Phe Ile Phe
            20                  25                  30

Lys Leu Glu Asp Asp Pro Ser Gln Ser Ser Glu Leu Leu Ala Glu Ala
        35                  40                  45

Lys Lys Leu Asn Asp Ala Gln Ala Pro Lys
    50                  55

<210> SEQ ID NO 146
<211> LENGTH: 58
<212> TYPE: PRT
<213> ORGANISM: Artificial sequence
<220> FEATURE:
<223> OTHER INFORMATION: Engineered ABD binding polypeptide

<400> SEQUENCE: 146

Val Asp Ala Lys Tyr Ala Lys Glu Leu Gly Trp Ala Phe Arg Glu Ile
1               5                   10                  15

Arg Asn Leu Pro Asn Leu Thr His Tyr Gln Arg Ile Ala Phe Ile Met
            20                  25                  30

Lys Leu Asp Asp Asp Pro Ser Gln Ser Ser Glu Leu Leu Ala Glu Ala
        35                  40                  45

Lys Lys Leu Asn Asp Ala Gln Ala Pro Lys
    50                  55

<210> SEQ ID NO 147
<211> LENGTH: 58
<212> TYPE: PRT
<213> ORGANISM: Artificial sequence
<220> FEATURE:
<223> OTHER INFORMATION: Engineered ABD binding polypeptide

<400> SEQUENCE: 147

Val Asp Ala Lys Tyr Ala Lys Glu Asn Leu Trp Ala Phe Asn Glu Ile
1               5                   10                  15

Lys Gly Leu Pro Asn Leu Thr His Asp Gln Arg Ile Ala Phe Ile Val
            20                  25                  30

Lys Leu Asp Asp Asp Pro Ser Gln Ser Ser Glu Leu Leu Ala Glu Ala
        35                  40                  45

Lys Lys Leu Asn Asp Ala Gln Ala Pro Lys
    50                  55

<210> SEQ ID NO 148
<211> LENGTH: 58
<212> TYPE: PRT
<213> ORGANISM: Artificial sequence
<220> FEATURE:
<223> OTHER INFORMATION: Engineered ABD binding polypeptide

<400> SEQUENCE: 148

Val Asp Ala Lys Tyr Ala Lys Glu Leu Ser Phe Ala Phe Ser Glu Ile
1               5                   10                  15

Asn Val Leu Pro Asn Leu Thr Phe His Gln Lys Ile Ala Phe Ile Tyr
            20                  25                  30

Lys Leu Glu Asp Asp Pro Ser Gln Ser Ser Glu Leu Leu Ala Glu Ala
        35                  40                  45

Lys Lys Leu Asn Asp Ala Gln Ala Pro Lys
    50                  55

<210> SEQ ID NO 149
<211> LENGTH: 58
<212> TYPE: PRT
<213> ORGANISM: Artificial sequence
<220> FEATURE:
<223> OTHER INFORMATION: Engineered ABD binding polypeptide

<400> SEQUENCE: 149

Val Asp Ala Lys Tyr Ala Lys Glu Phe Arg Gly Ala Ile Ala Glu Ile
1               5                   10                  15

Arg Asp Leu Pro Asn Leu Thr Leu Glu Gln Lys Tyr Ala Phe Ile Phe
            20                  25                  30

Lys Leu Glu Asp Asp Pro Ser Gln Ser Ser Glu Leu Leu Ala Glu Ala
        35                  40                  45

Lys Lys Leu Asn Asp Ala Gln Ala Pro Lys
    50                  55

<210> SEQ ID NO 150
<211> LENGTH: 58
<212> TYPE: PRT
<213> ORGANISM: Artificial sequence
<220> FEATURE:
<223> OTHER INFORMATION: Engineered ABD binding polypeptide

<400> SEQUENCE: 150

Val Asp Ala Lys Tyr Ala Lys Glu Glu Glu Asn Ala Tyr Lys Glu Ile
1               5                   10                  15

Gly Ser Leu Pro Asn Leu Thr Leu Ala Gln Lys Val Ala Phe Ile Leu
            20                  25                  30

Lys Leu Glu Asp Asp Pro Ser Gln Ser Ser Glu Leu Leu Ala Glu Ala
        35                  40                  45

Lys Lys Leu Asn Asp Ala Gln Ala Pro Lys
    50                  55

<210> SEQ ID NO 151
<211> LENGTH: 58
<212> TYPE: PRT
<213> ORGANISM: Artificial sequence
<220> FEATURE:
<223> OTHER INFORMATION: Engineered ABD binding polypeptide

<400> SEQUENCE: 151

Val Asp Ala Lys Tyr Ala Lys Glu Leu Arg Gln Ala Leu Gln Glu Ile
1               5                   10                  15

His Ile Leu Pro Asn Leu Thr His Ser Gln Arg Val Ala Phe Ile Val
            20                  25                  30

Lys Leu Asp Asp Asp Pro Ser Gln Ser Ser Glu Leu Leu Ala Glu Ala
        35                  40                  45

Lys Lys Leu Asn Asp Ala Gln Ala Pro Lys
    50                  55

<210> SEQ ID NO 152
<211> LENGTH: 58
<212> TYPE: PRT
<213> ORGANISM: Artificial sequence
<220> FEATURE:
<223> OTHER INFORMATION: Engineered ABD binding polypeptide

<400> SEQUENCE: 152

-continued

Val Asp Ala Lys Tyr Ala Lys Glu Asn His Ala Ala Phe Gln Glu Ile
1               5                   10                  15

Leu Ser Leu Pro Asn Leu Thr Leu Asn Gln Arg Leu Ala Phe Ile Thr
            20                  25                  30

Lys Leu Asp Asp Pro Ser Gln Ser Ser Glu Leu Leu Ala Glu Ala
        35                  40                  45

Lys Lys Leu Asn Asp Ala Gln Ala Pro Lys
    50                  55

<210> SEQ ID NO 153
<211> LENGTH: 58
<212> TYPE: PRT
<213> ORGANISM: Artificial sequence
<220> FEATURE:
<223> OTHER INFORMATION: Engineered ABD binding polypeptide

<400> SEQUENCE: 153

Val Asp Ala Lys Tyr Ala Lys Glu Thr Asn Tyr Ala Phe Lys Glu Ile
1               5                   10                  15

Asp Leu Leu Pro Asn Leu Thr Leu Met Gln Lys Leu Ala Phe Ile Val
            20                  25                  30

Lys Leu Asp Asp Pro Ser Gln Ser Ser Glu Leu Leu Ala Glu Ala
        35                  40                  45

Lys Lys Leu Asn Asp Ala Gln Ala Pro Lys
    50                  55

<210> SEQ ID NO 154
<211> LENGTH: 58
<212> TYPE: PRT
<213> ORGANISM: Artificial sequence
<220> FEATURE:
<223> OTHER INFORMATION: Engineered ABD binding polypeptide

<400> SEQUENCE: 154

Val Asp Ala Lys Tyr Ala Lys Glu Ile Ser Leu Ala Phe Lys Glu Ile
1               5                   10                  15

Lys Ala Leu Pro Asn Leu Thr Gly Gln Gln Arg Phe Ala Phe Ile Leu
            20                  25                  30

Lys Leu Asp Asp Pro Ser Gln Ser Ser Glu Leu Leu Ala Glu Ala
        35                  40                  45

Lys Lys Leu Asn Asp Ala Gln Ala Pro Lys
    50                  55

<210> SEQ ID NO 155
<211> LENGTH: 58
<212> TYPE: PRT
<213> ORGANISM: Artificial sequence
<220> FEATURE:
<223> OTHER INFORMATION: Engineered ABD binding polypeptide

<400> SEQUENCE: 155

Val Asp Ala Lys Tyr Ala Lys Glu Leu Ser Lys Ala Leu Thr Glu Ile
1               5                   10                  15

Arg Met Leu Pro Asn Leu Thr Phe Arg Gln Arg Ile Ala Phe Ile Ile
            20                  25                  30

Lys Leu Asp Asp Pro Ser Gln Ser Ser Glu Leu Leu Ala Glu Ala
        35                  40                  45

Lys Lys Leu Asn Asp Ala Gln Ala Pro Lys
    50                  55

-continued

<210> SEQ ID NO 156
<211> LENGTH: 58
<212> TYPE: PRT
<213> ORGANISM: Artificial sequence
<220> FEATURE:
<223> OTHER INFORMATION: Engineered ABD binding polypeptide

<400> SEQUENCE: 156

Val Asp Ala Lys Tyr Ala Lys Glu Leu Asp Met Ala Tyr Thr Glu Ile
1               5                   10                  15

Gly Leu Leu Pro Asn Leu Thr Phe Ser Gln Leu Leu Ala Phe Ile Ile
            20                  25                  30

Lys Leu Asp Asp Asp Pro Ser Gln Ser Ser Glu Leu Leu Ala Glu Ala
        35                  40                  45

Lys Lys Leu Asn Asp Ala Gln Ala Pro Lys
    50                  55

<210> SEQ ID NO 157
<211> LENGTH: 46
<212> TYPE: PRT
<213> ORGANISM: Streptococcus sp. G148

<400> SEQUENCE: 157

Leu Ala Glu Ala Lys Val Leu Ala Asn Arg Glu Leu Asp Lys Tyr Gly
1               5                   10                  15

Val Ser Asp Tyr Tyr Lys Asn Leu Ile Asn Asn Ala Lys Thr Val Glu
            20                  25                  30

Gly Val Lys Ala Leu Ile Asp Glu Ile Leu Ala Ala Leu Pro
        35                  40                  45

<210> SEQ ID NO 158
<211> LENGTH: 47
<212> TYPE: PRT
<213> ORGANISM: Artificial sequence
<220> FEATURE:
<223> OTHER INFORMATION: Engineered albumin binding domain

<400> SEQUENCE: 158

Cys Leu Ala Glu Ala Lys Val Leu Ala Asn Arg Glu Leu Asp Lys Tyr
1               5                   10                  15

Gly Val Ser Asp Tyr Tyr Lys Asn Leu Ile Asn Asn Ala Lys Thr Val
            20                  25                  30

Glu Gly Val Lys Ala Leu Ile Asp Glu Ile Leu Ala Ala Leu Pro
        35                  40                  45

<210> SEQ ID NO 159
<211> LENGTH: 46
<212> TYPE: PRT
<213> ORGANISM: Artificial sequence
<220> FEATURE:
<223> OTHER INFORMATION: Engineered albumin binding domain

<400> SEQUENCE: 159

Leu Ala Glu Ala Lys Val Leu Ala Asn Arg Glu Leu Asp Lys Tyr Gly
1               5                   10                  15

Val Ser Asp Phe Tyr Lys Arg Leu Ile Asn Lys Ala Lys Thr Val Glu
            20                  25                  30

Gly Val Glu Ala Leu Lys Leu His Ile Leu Ala Ala Leu Pro
        35                  40                  45

<210> SEQ ID NO 160
<211> LENGTH: 46

```
<212> TYPE: PRT
<213> ORGANISM: Artificial sequence
<220> FEATURE:
<223> OTHER INFORMATION: Engineered albumin binding domain

<400> SEQUENCE: 160

Leu Ala Glu Ala Lys Glu Ala Ala Asn Ala Glu Leu Asp Ser Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu Pro
        35                  40                  45

<210> SEQ ID NO 161
<211> LENGTH: 48
<212> TYPE: PRT
<213> ORGANISM: Artificial sequence
<220> FEATURE:
<223> OTHER INFORMATION: Engineered albumin binding domain

<400> SEQUENCE: 161

Gly Ser Leu Ala Glu Ala Lys Glu Ala Ala Asn Ala Glu Leu Asp Ser
1               5                   10                  15

Tyr Gly Val Ser Asp Phe Tyr Lys Arg Leu Ile Asp Lys Ala Lys Thr
            20                  25                  30

Val Glu Gly Val Glu Ala Leu Lys Asp Ala Ile Leu Ala Ala Leu Pro
        35                  40                  45

<210> SEQ ID NO 162
<211> LENGTH: 47
<212> TYPE: PRT
<213> ORGANISM: Artificial sequence
<220> FEATURE:
<223> OTHER INFORMATION: Engineered albumin binding domain

<400> SEQUENCE: 162

Gly Leu Ala Ser Ala Lys Glu Ala Ala Asn Ala Glu Leu Asp Cys Tyr
1               5                   10                  15

Gly Val Ser Asp Phe Tyr Lys Arg Leu Ile Asp Lys Ala Lys Thr Val
            20                  25                  30

Glu Gly Val Glu Ala Leu Lys Asp Ala Ile Leu Ala Ala Leu Pro
        35                  40                  45

<210> SEQ ID NO 163
<211> LENGTH: 24
<212> TYPE: DNA
<213> ORGANISM: Artificial sequence
<220> FEATURE:
<223> OTHER INFORMATION: Synthetic primer

<400> SEQUENCE: 163
tgcttccggc tcgtatgttg tgtg                                            24

<210> SEQ ID NO 164
<211> LENGTH: 21
<212> TYPE: DNA
<213> ORGANISM: Artificial sequence
<220> FEATURE:
<223> OTHER INFORMATION: Synthetic primer

<400> SEQUENCE: 164
cggaaccaga gccaccaccg g                                               21
```

```
<210> SEQ ID NO 165
<211> LENGTH: 21
<212> TYPE: DNA
<213> ORGANISM: Artificial sequence
<220> FEATURE:
<223> OTHER INFORMATION: Synthetic primer

<400> SEQUENCE: 165
cggaaccaga gccaccaccg g                                              21

<210> SEQ ID NO 166
<211> LENGTH: 29
<212> TYPE: PRT
<213> ORGANISM: Artificial Sequence
<220> FEATURE:
<223> OTHER INFORMATION: Engineered Polypeptide
<220> FEATURE:
<221> NAME/KEY: MISC_FEATURE
<222> LOCATION: (2)..(2)
<223> OTHER INFORMATION: Xaa is selected from F, I and L
<220> FEATURE:
<221> NAME/KEY: MISC_FEATURE
<222> LOCATION: (3)..(3)
<223> OTHER INFORMATION: Xaa is selected from H, K, N, Q, R, S, T and V
<220> FEATURE:
<221> NAME/KEY: MISC_FEATURE
<222> LOCATION: (4)..(4)
<223> OTHER INFORMATION: Xaa is selected from A, D, F, G, H, I, K, L, M,
      N, Q, R, S, T, V, W and Y
<220> FEATURE:
<221> NAME/KEY: MISC_FEATURE
<222> LOCATION: (6)..(6)
<223> OTHER INFORMATION: Xaa is selected from F, I, L and Y
<220> FEATURE:
<221> NAME/KEY: MISC_FEATURE
<222> LOCATION: (7)..(7)
<223> OTHER INFORMATION: Xaa is selected from A, H, I, K, L, N, Q, R, S,
      T and V
<220> FEATURE:
<221> NAME/KEY: MISC_FEATURE
<222> LOCATION: (10)..(10)
<223> OTHER INFORMATION: Xaa is selected from G, H, K, N, Q, R, and S
<220> FEATURE:
<221> NAME/KEY: MISC_FEATURE
<222> LOCATION: (11)..(11)
<223> OTHER INFORMATION: Xaa is selected from A, D, F, G, I, K, L, N, Q,
      R, S, T, V and Y
<220> FEATURE:
<221> NAME/KEY: MISC_FEATURE
<222> LOCATION: (16)..(16)
<223> OTHER INFORMATION: Xaa is selected from N and T
<220> FEATURE:
<221> NAME/KEY: MISC_FEATURE
<222> LOCATION: (17)..(17)
<223> OTHER INFORMATION: Xaa is selected from F, H, L, S and T
<220> FEATURE:
<221> NAME/KEY: MISC_FEATURE
<222> LOCATION: (18)..(18)
<223> OTHER INFORMATION: Xaa is selected from D, E, H, I, K, L, M, N, Q,
      R, S, T and V
<220> FEATURE:
<221> NAME/KEY: MISC_FEATURE
<222> LOCATION: (20)..(20)
<223> OTHER INFORMATION: Xaa is selected from H, K and R
<220> FEATURE:
<221> NAME/KEY: MISC_FEATURE
<222> LOCATION: (21)..(21)
<223> OTHER INFORMATION: Xaa is selected from I, L and V
<220> FEATURE:
<221> NAME/KEY: MISC_FEATURE
<222> LOCATION: (25)..(25)
<223> OTHER INFORMATION: Xaa is selected from F, I, L, V and Y
<220> FEATURE:
<221> NAME/KEY: MISC_FEATURE
<222> LOCATION: (26)..(26)
<223> OTHER INFORMATION: Xaa is selected from K and S
<220> FEATURE:
```

<221> NAME/KEY: MISC_FEATURE
<222> LOCATION: (28)..(28)
<223> OTHER INFORMATION: Xaa is selected from D and E

<400> SEQUENCE: 166

Glu Xaa Xaa Xaa Ala Xaa Xaa Glu Ile Xaa Xaa Leu Pro Asn Leu Xaa
1               5                   10                  15

Xaa Xaa Gln Xaa Xaa Ala Phe Ile Xaa Xaa Leu Xaa Asp
            20                  25

<210> SEQ ID NO 167
<211> LENGTH: 20
<212> TYPE: PRT
<213> ORGANISM: Artificial Sequence
<220> FEATURE:
<223> OTHER INFORMATION: Engineered Polypeptide
<220> FEATURE:
<221> NAME/KEY: MISC_FEATURE
<222> LOCATION: (1)..(2)
<223> OTHER INFORMATION: ABD Binding Motif
<220> FEATURE:
<221> NAME/KEY: MISC_FEATURE
<222> LOCATION: (7)..(7)
<223> OTHER INFORMATION: Xaa is selected from A and S
<220> FEATURE:
<221> NAME/KEY: MISC_FEATURE
<222> LOCATION: (8)..(8)
<223> OTHER INFORMATION: Xaa is selected from N and E
<220> FEATURE:
<221> NAME/KEY: MISC_FEATURE
<222> LOCATION: (11)..(11)
<223> OTHER INFORMATION: Xaa is selected from A, S and C
<220> FEATURE:
<221> NAME/KEY: MISC_FEATURE
<222> LOCATION: (19)..(19)
<223> OTHER INFORMATION: Xaa is selected from A and S

<400> SEQUENCE: 167

Lys Asp Pro Ser Gln Ser Xaa Xaa Leu Leu Xaa Glu Ala Lys Lys Leu
1               5                   10                  15

Asn Asp Xaa Gln
            20

<210> SEQ ID NO 168
<211> LENGTH: 24
<212> TYPE: PRT
<213> ORGANISM: Artificial Sequence
<220> FEATURE:
<223> OTHER INFORMATION: Engineered Polypeptide
<220> FEATURE:
<221> NAME/KEY: MISC_FEATURE
<222> LOCATION: (3)..(4)
<223> OTHER INFORMATION: ABD Binding Motif
<220> FEATURE:
<221> NAME/KEY: MISC_FEATURE
<222> LOCATION: (13)..(13)
<223> OTHER INFORMATION: Xaa is selected from S and C

<400> SEQUENCE: 168

Tyr Ala Lys Asp Pro Ser Gln Ser Ser Glu Leu Leu Xaa Glu Ala Lys
1               5                   10                  15

Lys Leu Asn Asp Ser Gln Ala Pro
            20

<210> SEQ ID NO 169
<211> LENGTH: 24
<212> TYPE: PRT
<213> ORGANISM: Artificial Sequence
<220> FEATURE:
<223> OTHER INFORMATION: Engineered Polypeptide

```
<220> FEATURE:
<221> NAME/KEY: MISC_FEATURE
<222> LOCATION: (3)..(4)
<223> OTHER INFORMATION: ABD Binding Motif
<220> FEATURE:
<221> NAME/KEY: MISC_FEATURE
<222> LOCATION: (13)..(13)
<223> OTHER INFORMATION: Xaa is selected from A and C

<400> SEQUENCE: 169

Tyr Ala Lys Asp Pro Ser Gln Ser Ser Glu Leu Leu Xaa Glu Ala Lys
1               5                   10                  15

Lys Leu Asn Asp Ala Gln Ala Pro
            20

<210> SEQ ID NO 170
<211> LENGTH: 24
<212> TYPE: PRT
<213> ORGANISM: Artificial Sequence
<220> FEATURE:
<223> OTHER INFORMATION: Engineered Polypeptide
<220> FEATURE:
<221> NAME/KEY: MISC_FEATURE
<222> LOCATION: (3)..(4)
<223> OTHER INFORMATION: ABD Binding Motif
<220> FEATURE:
<221> NAME/KEY: MISC_FEATURE
<222> LOCATION: (13)..(13)
<223> OTHER INFORMATION: Xaa is selected from A and C

<400> SEQUENCE: 170

Phe Asn Lys Asp Pro Ser Gln Ser Ala Asn Leu Leu Xaa Glu Ala Lys
1               5                   10                  15

Lys Leu Asn Asp Ala Gln Ala Pro
            20

<210> SEQ ID NO 171
<211> LENGTH: 29
<212> TYPE: PRT
<213> ORGANISM: Artificial Sequence
<220> FEATURE:
<223> OTHER INFORMATION: Engineered Polypeptide
<220> FEATURE:
<221> NAME/KEY: MISC_FEATURE
<222> LOCATION: (7)..(8)
<223> OTHER INFORMATION: ABD Binding Motif

<400> SEQUENCE: 171

Ala Asp Asn Asn Phe Asn Lys Asp Pro Ser Gln Ser Ala Asn Leu Leu
1               5                   10                  15

Ser Glu Ala Lys Lys Leu Asn Glu Ser Gln Ala Pro Lys
            20                  25

<210> SEQ ID NO 172
<211> LENGTH: 29
<212> TYPE: PRT
<213> ORGANISM: Artificial Sequence
<220> FEATURE:
<223> OTHER INFORMATION: Engineered Polypeptide
<220> FEATURE:
<221> NAME/KEY: MISC_FEATURE
<222> LOCATION: (7)..(8)
<223> OTHER INFORMATION: ABD Binding Motif

<400> SEQUENCE: 172

Ala Asp Asn Lys Phe Asn Lys Asp Pro Ser Gln Ser Ala Asn Leu Leu
1               5                   10                  15

Ala Glu Ala Lys Lys Leu Asn Asp Ala Gln Ala Pro Lys
```

```
                        20                  25

<210> SEQ ID NO 173
<211> LENGTH: 29
<212> TYPE: PRT
<213> ORGANISM: Artificial Sequence
<220> FEATURE:
<223> OTHER INFORMATION: Engineered Polypeptide
<220> FEATURE:
<221> NAME/KEY: MISC_FEATURE
<222> LOCATION: (7)..(8)
<223> OTHER INFORMATION: ABD Binding Motif

<400> SEQUENCE: 173

Ala Asp Asn Lys Phe Asn Lys Asp Pro Ser Val Ser Lys Glu Ile Leu
1               5                   10                  15

Ala Glu Ala Lys Lys Leu Asn Asp Ala Gln Ala Pro Lys
            20                  25

<210> SEQ ID NO 174
<211> LENGTH: 32
<212> TYPE: PRT
<213> ORGANISM: Artificial Sequence
<220> FEATURE:
<223> OTHER INFORMATION: Engineered Polypeptide
<220> FEATURE:
<221> NAME/KEY: MISC_FEATURE
<222> LOCATION: (10)..(11)
<223> OTHER INFORMATION: ABD Binding Motif

<400> SEQUENCE: 174

Ala Asp Ala Gln Gln Asn Asn Phe Asn Lys Asp Pro Ser Gln Ser Thr
1               5                   10                  15

Asn Val Leu Gly Glu Ala Lys Lys Leu Asn Glu Ser Gln Ala Pro Lys
            20                  25                  30

<210> SEQ ID NO 175
<211> LENGTH: 27
<212> TYPE: PRT
<213> ORGANISM: Artificial Sequence
<220> FEATURE:
<223> OTHER INFORMATION: Engineered Polypeptide
<220> FEATURE:
<221> NAME/KEY: MISC_FEATURE
<222> LOCATION: (5)..(6)
<223> OTHER INFORMATION: ABD Binding Motif

<400> SEQUENCE: 175

Ala Gln His Asp Glu Asp Pro Ser Gln Ser Ala Asn Val Leu Gly Glu
1               5                   10                  15

Ala Gln Lys Leu Asn Asp Ser Gln Ala Pro Lys
            20                  25

<210> SEQ ID NO 176
<211> LENGTH: 29
<212> TYPE: PRT
<213> ORGANISM: Artificial Sequence
<220> FEATURE:
<223> OTHER INFORMATION: Engineered Polypeptide
<220> FEATURE:
<221> NAME/KEY: MISC_FEATURE
<222> LOCATION: (7)..(8)
<223> OTHER INFORMATION: ABD Binding Motif

<400> SEQUENCE: 176

Val Asp Asn Lys Phe Asn Lys Asp Pro Ser Gln Ser Ala Asn Leu Leu
1               5                   10                  15
```

Ala Glu Ala Lys Lys Leu Asn Asp Ala Gln Ala Pro Lys
            20                  25

<210> SEQ ID NO 177
<211> LENGTH: 29
<212> TYPE: PRT
<213> ORGANISM: Artificial Sequence
<220> FEATURE:
<223> OTHER INFORMATION: Engineered Polypeptide
<220> FEATURE:
<221> NAME/KEY: MISC_FEATURE
<222> LOCATION: (7)..(8)
<223> OTHER INFORMATION: ABD Binding Motif

<400> SEQUENCE: 177

Ala Glu Ala Lys Tyr Ala Lys Asp Pro Ser Glu Ser Glu Leu Leu
1               5                   10                  15

Ser Glu Ala Lys Lys Leu Asn Lys Ser Gln Ala Pro Lys
            20                  25

<210> SEQ ID NO 178
<211> LENGTH: 29
<212> TYPE: PRT
<213> ORGANISM: Artificial Sequence
<220> FEATURE:
<223> OTHER INFORMATION: Engineered Polypeptide
<220> FEATURE:
<221> NAME/KEY: MISC_FEATURE
<222> LOCATION: (7)..(8)
<223> OTHER INFORMATION: ABD Binding Motif

<400> SEQUENCE: 178

Val Asp Ala Lys Tyr Ala Lys Asp Pro Ser Gln Ser Ser Glu Leu Leu
1               5                   10                  15

Ala Glu Ala Lys Lys Leu Asn Asp Ala Gln Ala Pro Lys
            20                  25

<210> SEQ ID NO 179
<211> LENGTH: 29
<212> TYPE: PRT
<213> ORGANISM: Artificial Sequence
<220> FEATURE:
<223> OTHER INFORMATION: Engineered Polypeptide
<220> FEATURE:
<221> NAME/KEY: MISC_FEATURE
<222> LOCATION: (7)..(8)
<223> OTHER INFORMATION: ABD Binding Motif

<400> SEQUENCE: 179

Val Asp Ala Lys Tyr Ala Lys Asp Pro Ser Gln Ser Ser Glu Leu Leu
1               5                   10                  15

Ala Glu Ala Lys Lys Leu Asn Asp Ser Gln Ala Pro Lys
            20                  25

<210> SEQ ID NO 180
<211> LENGTH: 29
<212> TYPE: PRT
<213> ORGANISM: Artificial Sequence
<220> FEATURE:
<223> OTHER INFORMATION: Engineered Polypeptide
<220> FEATURE:
<221> NAME/KEY: MISC_FEATURE
<222> LOCATION: (7)..(8)
<223> OTHER INFORMATION: ABD Binding Motif

<400> SEQUENCE: 180

Ala Glu Ala Lys Tyr Ala Lys Asp Pro Ser Gln Ser Ser Glu Leu Leu
1               5                   10                  15

Ser Glu Ala Lys Lys Leu Asn Asp Ser Gln Ala Pro Lys
            20                  25

<210> SEQ ID NO 181
<211> LENGTH: 29
<212> TYPE: PRT
<213> ORGANISM: Artificial Sequence
<220> FEATURE:
<223> OTHER INFORMATION: Engineered Polypeptide
<220> FEATURE:
<221> NAME/KEY: MISC_FEATURE
<222> LOCATION: (7)..(8)
<223> OTHER INFORMATION: ABD Binding Motif

<400> SEQUENCE: 181

Val Asp Ala Lys Tyr Ala Lys Asp Pro Ser Gln Ser Ser Glu Leu Leu
1               5                   10                  15

Ser Glu Ala Lys Lys Leu Asn Asp Ser Gln Ala Pro Lys
            20                  25

<210> SEQ ID NO 182
<211> LENGTH: 29
<212> TYPE: PRT
<213> ORGANISM: Artificial Sequence
<220> FEATURE:
<223> OTHER INFORMATION: Engineered Polypeptide
<220> FEATURE:
<221> NAME/KEY: MISC_FEATURE
<222> LOCATION: (7)..(8)
<223> OTHER INFORMATION: ABD Binding Motif

<400> SEQUENCE: 182

Val Asp Ala Lys Tyr Ala Lys Asp Pro Ser Gln Ser Ser Glu Leu Leu
1               5                   10                  15

Ala Glu Ala Lys Lys Leu Asn Lys Ala Gln Ala Pro Lys
            20                  25

<210> SEQ ID NO 183
<211> LENGTH: 29
<212> TYPE: PRT
<213> ORGANISM: Artificial Sequence
<220> FEATURE:
<223> OTHER INFORMATION: Engineered Polypeptide
<220> FEATURE:
<221> NAME/KEY: MISC_FEATURE
<222> LOCATION: (7)..(8)
<223> OTHER INFORMATION: ABD Binding Motif

<400> SEQUENCE: 183

Ala Glu Ala Lys Tyr Ala Lys Asp Pro Ser Gln Ser Ser Glu Leu Leu
1               5                   10                  15

Ala Glu Ala Lys Lys Leu Asn Lys Ala Gln Ala Pro Lys
            20                  25

<210> SEQ ID NO 184
<211> LENGTH: 29
<212> TYPE: PRT
<213> ORGANISM: Artificial Sequence
<220> FEATURE:
<223> OTHER INFORMATION: Engineered Polypeptide
<220> FEATURE:
<221> NAME/KEY: MISC_FEATURE
<222> LOCATION: (7)..(8)
<223> OTHER INFORMATION: ABD Binding Motif

<400> SEQUENCE: 184

Val Asp Ala Lys Tyr Ala Lys Asp Pro Ser Gln Ser Ser Glu Leu Leu

```
1               5                  10                 15
Ala Glu Ala Lys Lys Leu Asn Asp Ala Gln Ala Pro Lys
                20                 25
```

<210> SEQ ID NO 185
<211> LENGTH: 16
<212> TYPE: PRT
<213> ORGANISM: Artificial Sequence
<220> FEATURE:
<223> OTHER INFORMATION: Engineered Polypeptide
<220> FEATURE:
<221> NAME/KEY: MISC_FEATURE
<222> LOCATION: (8)..(9)
<223> OTHER INFORMATION: Z Variant
<220> FEATURE:
<221> NAME/KEY: MISC_FEATURE
<222> LOCATION: (12)..(13)
<223> OTHER INFORMATION: Z03639

<400> SEQUENCE: 185

```
Ala Gln His Asp Glu Ala Leu Glu Val Asp Tyr Val Tyr Val Pro Gly
1               5                  10                 15
```

<210> SEQ ID NO 186
<211> LENGTH: 15
<212> TYPE: PRT
<213> ORGANISM: Artificial Sequence
<220> FEATURE:
<223> OTHER INFORMATION: Engineered Polypeptide
<220> FEATURE:
<221> NAME/KEY: MISC_FEATURE
<222> LOCATION: (12)..(13)
<223> OTHER INFORMATION: Two Consecutive Z Variant

<400> SEQUENCE: 186

```
Met Gly Ser Ser His His His His His His Leu Gln Val Asp Cys
1               5                  10                 15
```

<210> SEQ ID NO 187
<211> LENGTH: 8
<212> TYPE: PRT
<213> ORGANISM: Artificial Sequence
<220> FEATURE:
<223> OTHER INFORMATION: Engineered Polypeptide
<220> FEATURE:
<221> NAME/KEY: MISC_FEATURE
<222> LOCATION: (5)..(6)
<223> OTHER INFORMATION: Two Consecutive Z06677

<400> SEQUENCE: 187

```
Gly Ser Ser Leu Gln Val Asp Cys
1               5
```

METHOD FOR THE SEPARATION OF PROTEINS CONTAINING AN ALBUMIN-BINDING

CROSS-REFERENCE TO RELATED APPLICATIONS

This Application is a U.S. National Stage Application of PCT/EP2013/072365, filed Oct. 25, 2013, which claims priority to U.S. Provisional Patent Application No. 61/718,246, filed Oct. 25, 2012, both of which are incorporated by reference in their entireties

FIELD OF THE INVENTION

This invention relates to a separation method employing polypeptides which bind to an albumin binding domain, ABD. The polypeptides disclosed herein have various industrial and pharmaceutical applications, for example use as an affinity ligand in separation technology or as a detection agent in molecular diagnostics.

BACKGROUND

Serum albumin is the most abundant protein in mammalian sera (35-50 g/l, i.e. 0.53-0.75 mM, in humans) and several strategies to covalently couple a peptide or protein to carrier molecule that will allow in vivo association to serum albumin have been described e.g. in WO91/01743, in WO01/45746 and in Dennis et al (J Biol Chem 277:35035-43, 2002). WO91/01743 describes inter alia the use of albumin binding peptides or proteins derived from streptococcal protein G (SpG) for increasing the half-life of other proteins. The idea is to fuse the bacterially derived, albumin binding peptide/protein to a therapeutically interesting peptide/protein, which has been shown to have a rapid elimination from blood. The generated fusion protein binds to serum albumin in vivo, and benefits from its longer half-life, which increases the net half-life of the fused therapeutically interesting peptide/protein. The half life of serum albumin is directly proportional to the size of the animal, where for example human serum albumin (HSA) has a half life of 19 days and rabbit serum albumin has a half life of about 5 days (McCurdy et al, J Lab Clin Med 143:115, 2004).

Streptococcal protein G (SpG) is a bi-functional receptor present on the surface of certain strains of streptococci and is capable of binding to both IgG and serum albumin (Björck et al, Mol Immunol 24:1113, 1987). The structure is highly repetitive, with several structurally and functionally different domains (Guss et al, EMBO J 5:1567, 1986), more precisely three Ig-binding domains and three serum albumin binding domains (Olsson et al, Eur J Biochem 168:319, 1987). The structure of one of the three serum albumin binding domains in SpG has been determined, showing a three-helix bundle fold (Kraulis et al, FEBS Lett 378:190, 1996, Johansson et al, J. Biol. Chem. 277:8114-20, 2002). A 46 amino acid motif was defined as ABD (albumin binding domain) and has subsequently also been designated G148-GA3 (GA for protein G-related albumin binding and G148 from the strain of Streptococcus from which it is derived).

Artificial variants of GA3-G148 having a very much improved affinity for human serum albumin were developed (Jonsson et al, Prot Eng Des Sel 21:515-27, 2008; WO2009/016043), as well as engineered high affinity variants with reduced immune stimulatory properties (WO2012/004384). The latter were motivated by the fact that a few T- and B-cell epitopes were experimentally identified within GA3-G148 (Goetsch et al, Clin Diagn Lab Immunol 10:125-32, 2003), making this domain as such less suitable for use in pharmaceutical compositions for human administration. Throughout the present text, GA3-G148 as well as the various engineered derivatives thereof presented e.g. in WO2009/016043 and WO2012/004384, are collectively referred to as "ABD". Thus, in the present disclosure, "ABD" denotes these classes of albumin binding polypeptides, rather than a specified polypeptide with a specific amino acid sequence.

With the increased interest in incorporating an albumin binding domain into therapeutic or diagnostic compositions follows a growing need for inexpensive and efficient purification strategies for isolation of molecules covalently linked to ABD, produced for instance by recombinant expression in prokaryotic or eukaryotic systems, or by direct chemical conjugation to ABD. A general strategy for purification of recombinantly expressed proteins would be to include a commonly used affinity tag such as a polyhistidine tag, a chitin binding protein (CBP), a maltose binding protein (MBP), a glutathione-S-transferase (GST)-tag or a FLAG-tag, and perform a classic affinity separation using commercial resins developed specifically for each tag. However, for certain applications, and in particular for molecules to be used as therapeutics, the end product must be homogeneous. Because the tag would need to be removed, e.g. by enzymatic or chemical cleavage, it is necessary to ensure complete cleavage to obtain a homogeneous product, or to suffer a loss of yield when removing incompletely cleaved product. Both of these issues serve to increase the production cost of the product. Therefore, a more motivated strategy would be to utilize the ABD moiety itself as a purification tag. One example of this would be to couple recombinant albumin to a solid support (see for example Jonsson et al, Prot Eng Des Sel 21:515-27, 2008; Andersen et al, J Biol Chem 286:5234-41, 2011). From a crude solute, compounds comprising an ABD tag are captured by albumin, non-specifically adsorbed contaminants are removed and ABD-tagged compounds are subsequently recovered by disrupting the specific but reversible interaction with albumin. However, albumin is a large natural carrier molecule with several interaction sites for different proteins, fatty acids, sterols, ions etc., and thus, the background binding of both specific and unspecific components may contaminate the recovered sample. Despite the fact that recombinant human albumin has been developed, it is still expensive to include as an affinity ligand in large-scale production of therapeutics, in particular because it is incompatible with standard procedures for cleaning in place, that would have to be applied for the repeated use of the albumin-coupled matrix. Furthermore, harsher elution conditions may be required to recover molecules containing ABD variants with an exceptionally high affinity for albumin. Such conditions may be unfavorable also for the ABD-tagged molecule.

Protein A from *Staphylococcus aureus* has long been used as an affinity ligand in the industrial production of monoclonal antibodies and Fc-fusion proteins, due to the native affinity of Protein A for the Fc portion of IgG. Protein A in its entirety, as well as the individual Fc-binding domains thereof, have subsequently served as starting points for the rational design of engineered affinity ligands with improved properties. For an introduction, see the papers by Nord K and co-workers in Prot Eng (Nord et al, Prot Eng 8:601-608; 1995) and Nat Biotech (Nord et al, Nat Biotech 15:772-777; 1997).

It is an object of the present disclosure to provide new methods for purification, separation and/or chromatography of protein molecules containing ABD, for example fusion proteins in which ABD is a fusion moiety. It is moreover an object of the disclosure to provide uses for ABD binding agents in biotechnology, for example in protein purification and separation applications.

DESCRIPTION OF THE INVENTION

These objects, and other objects apparent to the skilled person from the present disclosure, may be achieved by one or more of the various inventive aspects disclosed below.

Thus, in a first aspect, the disclosure provides a method of separation of at least one ABD-containing molecule present in a liquid from other constituents in the liquid, which method comprises a step of affinity separation, in which step is used, as affinity ligand, an ABD binding polypeptide comprising an ABD binding motif BM, which motif consists of an amino acid sequence selected from:

i)
(SEQ ID NO: 166)
$EX_2X_3X_4AX_6X_7EI\ X_{10}X_{11}LPNLX_{16}X_{17}X_{18}QX_{20}\ X_{21}AFIX_{25}X_{26}LX_{28}D$ wherein, independently from each other,
  $X_2$ is selected from F, I and L;
  $X_3$ is selected from H, K, N, Q, R, S, T and V;
  $X_4$ is selected from A, D, F, G, H, I, K, L, M, N, Q, R, S, T, V, W and Y;
  $X_6$ is selected from F, I, L and Y;
  $X_7$ is selected from A, H, I, K, L, N, Q, R, S, T and V;
  $X_{10}$ is selected from G, H, K, N, Q, R and S;
  $X_{11}$ is selected from A, D, F, G, I, K, L, N, Q, R, S, T, V and Y;
  $X_{16}$ is selected from N and T;
  $X_{17}$ is selected from F, H, L, S and T;
  $X_{18}$ is selected from D, E, H, I, K, L, M, N, Q, R, S, T and V;
  $X_{20}$ is selected from H, K and R;
  $X_{21}$ is selected from I, L and V;
  $X_{25}$ is selected from F, I, L, V and Y;
  $X_{26}$ is selected from K and S;
  $X_{28}$ is selected from D and E;
and
ii) an amino acid sequence which has at least 89% identity to the sequence defined in i).

As is will be realized by the person of skill in the art of affinity chromatography, the disclosed method of separation may be employed in the removal and/or purification of molecules comprising ABD, i.e. "ABD-containing molecules". Such molecules may in particular be fusion proteins, in which one fusion moiety comprises one or more ABD domains, and other fusion moieties have other functions, such as biologically active functions, for example therapeutic or diagnostic functions.

The method comprises a step of affinity separation, in which step a polypeptide as defined above is used. More specific variants and embodiments of the ABD binding polypeptide are given below. Thus, the invention provides the use of the polypeptide as described herein in a method of affinity separation. Suitably, the method involves a separation device. The separation device may suitably comprise a solid support, for example selected from chromatographic media, membranes, cellulose, silica, agarose, polyacrylamide, magnetic beads, two-phase systems and other such materials commonly used in separation. In one embodiment, the polypeptide defined herein has been coupled to a solid support of a separation device. The thus obtained separation device, having a polypeptide as defined herein coupled thereto, is referred to throughout the description and claims as an "affinity matrix" or "resin", and a particular embodiment thereof is referred to in the examples as "anti-ABD agarose".

For the purposes of purification of an ABD-containing molecule from a liquid, the liquid containing ABD-containing molecule to be purified is suitably applied to such an affinity matrix under conditions that are conducive to binding of ABD-containing molecule to the matrix. Thereafter, the affinity matrix is washed under conditions such that the binding of ABD-containing molecule to the matrix is maintained, but most, ideally all, other proteins and contaminants bound to the matrix are washed away. In an elution step, the matrix is treated such that ABD-containing molecule is released from the matrix in an ABD-containing molecule enriched fraction denoted "ABD-containing molecule fraction", which may be recovered.

If, conversely, the purpose of the separation is the removal of ABD-containing molecule, essentially the same steps as above are suitably followed, with some exceptions. The liquid containing ABD-containing molecule to be removed is suitably applied to an affinity matrix under conditions that are conducive to binding of ABD-containing molecule to the matrix. Thereafter, the affinity matrix is washed under conditions such that the binding of ABD-containing molecule to the matrix is maintained, but most, ideally all, other proteins are recovered in the flow-through, thus obtaining a "depleted fraction" with a substantial reduction in ABD-containing molecule content, which is recovered. Thus, the constituents of the liquid that are not ABD-containing molecules and that were discarded in the purification method above, may instead be retained and used and/or processed further.

As a further alternative of the inventive method, both the "depleted fraction" and the "ABD-containing molecule fraction" may be recovered from the same separation run. Then, once again, the liquid containing ABD-containing molecule is suitably applied to an affinity matrix under conditions that are conducive to binding of ABD-containing molecule to the matrix. Thereafter, the affinity matrix is washed, under conditions such that the binding of ABD-containing molecule to the matrix is maintained, but most, ideally all, other proteins are recovered in the flow-through. The thus obtained "depleted fraction" with a substantial reduction in ABD-containing molecule content is recovered. In an elution step, the matrix is treated such that ABD-containing molecule is released from the matrix in an ABD-containing molecule enriched fraction denoted "ABD-containing molecule fraction", which is recovered.

In one embodiment, the disclosed separation method is carried out in a batch setup. In another embodiment, the method is carried out in a column setup. In still another embodiment, the method is carried out using expanded bed adsorption. It is also possible to carry out the disclosed method using hybrid set-ups, such as binding in batch mode followed by wash and elution in a column setup. The person of skill in affinity chromatography is aware of the available alternatives and may put them into practice without undue effort.

The ABD binding polypeptide disclosed herein exhibits a set of characteristics, which, for example when coupled to a solid support, makes it suitable as an affinity ligand for separation of molecules comprising ABD. For example, in comparison with using human albumin as affinity ligand, the use of the disclosed ABD binding polypeptide in the disclosed separation method demonstrates the following advantages:

Higher separation capacity per ml ligand-coupled matrix.

Compatibility with repeated procedures for cleaning in place, for example using 0.5 M sodium hydroxide, which makes the ABD binding polypeptide useful in the large scale production of therapeutics.

Enablement of milder elution conditions, for example elution at a higher pH, which makes possible the separation of a wider range of different molecules comprising ABD.

In the context of the present disclosure, the terms "sample" and "liquid" may be used interchangeably. Neither term implies any limitations, for example with regard to the volume of liquid involved or other characteristics. The liquid may be of a small volume, such as an aliquot of a larger volume, e.g. for analytical purposes; or alternatively, the feed or liquid used in a large scale separation and/or purification process.

The method disclosed herein may be useful at one or more of the different stages of purification. Thus, it may be used without limitation at either one or more of a first capture step, in any intermediate purification step or in a final polishing step.

The skilled person will appreciate that successful purification of a target protein, using a method according to the present disclosure, employing a resin comprising an ABD binding polypeptide as described herein may be achieved regardless of where in the target protein the ABD moiety is situated. Hence, the ABD moiety may be placed at the N-terminus or at the C-terminus of the target protein. Alternatively, the target protein may be a fusion protein which comprises an ABD moiety flanked by other protein moieties on both sides.

In the context of the present disclosure, "ABD" refers to three-helix albumin binding domains from streptococcal protein G and their derivatives. In particular, "ABD" may refer to GA3-G148 (Johansson et al, supra, hereby incorporated by reference) or variants of GA3-G148 having improved affinity for albumin (WO2009/016043, hereby incorporated by reference), as well as high affinity variants with reduced immune stimulatory properties (WO2012/004384, hereby incorporated by reference). In other words, in the present disclosure, "ABD" denotes the classes of albumin binding polypeptides described in the referenced works, rather than a specified polypeptide with a specific amino acid sequence.

The above definition of a class of sequence related, ABD binding polypeptides for use in the disclosed separation method is based on a statistical analysis of a number of random polypeptide variants of a parent scaffold, that were selected for their interaction with ABD in several different selection experiments. The identified ABD binding motif, or "BM", corresponds to the target binding region of the parent scaffold, which region constitutes two alpha helices within a three-helical bundle protein domain. In the parent scaffold, the varied amino acid residues of the two BM helices constitute a binding surface for interaction with the constant Fc part of antibodies. In the present invention, the random variation of binding surface residues and subsequent selection of variants have replaced the Fc interaction capacity with a capacity for interaction with ABD.

As the skilled person will realize, the function of any polypeptide, such as the ABD binding capacity of the polypeptide for use in the disclosed separation method, is dependent on the tertiary structure of the polypeptide. It is therefore possible to make minor changes to the sequence of amino acids in a polypeptide without affecting the function thereof. Thus, the invention encompasses methods and uses with polypeptides comprising modified variants of the BM which are such that the resulting sequence is at least 89% identical to a sequence defined by i). In one embodiment, said modified variants of the BM are such that they are 93% identical to a sequence defined by i). In yet another embodiment, said BM variants are 96% identical to a sequence defined by i).

In some embodiments, such changes may be made in all positions of the sequences of the ABD binding polypeptide used in the disclosed separation method. In other embodiments, such changes may be made only in the non-variable positions, also denoted as scaffold amino acid residues. In such cases, changes are not allowed in the variable positions, i.e. positions denoted with an "X" in sequence i). For example, it is possible that an amino acid residue belonging to a certain functional grouping of amino acid residues (e.g. hydrophobic, hydrophilic, polar etc) could be exchanged for another amino acid residue from the same functional group.

The term "% identity", as used throughout, may be calculated as follows. The query sequence is aligned to the target sequence using the CLUSTAL W algorithm (Thompson et al, Nucleic Acids Research, 22: 4673-4680 (1994)). A comparison is made over the window corresponding to the shortest of the aligned sequences. The shortest of the aligned sequences may in some instances be the target sequence. In other instances, the query sequence may constitute the shortest of the aligned sequences. The amino acid residues at each position are compared, and the percentage of positions in the query sequence that have identical correspondences in the target sequence is reported as % identity.

In one embodiment, $X_2$ in sequence i) is selected from F and L.

In one embodiment, $X_2$ in sequence i) is F.

In one embodiment, $X_2$ in sequence i) is L.

In one embodiment, $X_3$ in sequence i) is selected from H, K, R, T and V.

In one embodiment, $X_3$ in sequence i) is selected from H, K, R and V.

In one embodiment, $X_3$ in sequence i) is selected from H, K and V.

In one embodiment, $X_3$ in sequence i) is selected from K and R.

In one embodiment, $X_3$ in sequence i) is K.

In one embodiment, $X_3$ in sequence i) is R.

In one embodiment, $X_3$ in sequence i) is V.

In one embodiment, $X_4$ in sequence i) is selected from A, H, I, L, N, V and W.

In one embodiment, $X_4$ in sequence i) is selected from H, L N, and V

In one embodiment, $X_4$ in sequence i) is V.

In one embodiment, $X_4$ in sequence i) is N.

In one embodiment, $X_4$ in sequence i) is H.

In one embodiment, $X_4$ in sequence i) is L.

In one embodiment, $X_4$ in sequence i) is selected from A, L, N, V and W.

In one embodiment, $X_4$ in sequence i) is selected from A, N, V and W.

In one embodiment, $X_4$ in sequence i) is selected from A, N and W.

In one embodiment, $X_6$ in sequence i) is selected from F and L.

In one embodiment, $X_6$ in sequence i) is F.

In one embodiment, $X_6$ in sequence i) is L.

In one embodiment, $X_7$ in sequence i) is selected from K, L, N, Q, R and S.

In one embodiment, $X_7$ in sequence i) is selected from K, N, Q, R and S.

In one embodiment, $X_7$ in sequence i) is selected from K, Q, R and S.

In one embodiment, $X_7$ in sequence i) is selected from K and R.

In one embodiment, $X_7$ in sequence i) is K.

In one embodiment, $X_7$ in sequence i) is R.

In one embodiment, $X_{10}$ in sequence i) is selected from H, K, N, and R.

In one embodiment, $X_{10}$ in sequence i) is selected from H, K and N.

In one embodiment, $X_{10}$ in sequence i) is selected from K, N and R.

In one embodiment, $X_{10}$ in sequence i) is selected from K and R.

In one embodiment, $X_{10}$ in sequence i) is N.

In one embodiment, $X_{10}$ in sequence i) is K.

In one embodiment, $X_{10}$ in sequence i) is R.

In one embodiment, $X_{10}$ in sequence i) is H.

In one embodiment, $X_{11}$ in sequence i) is selected from A, F, L, R, T and Y.

In one embodiment, $X_{11}$ in sequence i) is selected from A, F, T and Y.

In one embodiment, $X_{11}$ in sequence i) is T.

In one embodiment, $X_{11}$ in sequence i) is A.

In one embodiment, $X_{11}$ in sequence i) is Y.

In one embodiment, $X_{11}$ in sequence i) is F.

In one embodiment, $X_{11}$ in sequence i) is selected from A, L, T and Y.

In one embodiment, $X_{11}$ in sequence i) is selected from T and Y.

In one embodiment, $X_{16}$ in sequence i) is T.

In one embodiment, $X_{17}$ in sequence i) is selected from F, H and L.

In one embodiment, $X_{17}$ in sequence i) is selected from F and H.

In one embodiment, $X_{17}$ in sequence i) is selected from H and L.

In one embodiment, $X_{17}$ in sequence i) is F.

In one embodiment, $X_{17}$ in sequence i) is H.

In one embodiment, $X_{17}$ in sequence i) is L.

In one embodiment, $X_{18}$ in sequence i) is selected from D, H, I, K and Q.

In one embodiment, $X_{18}$ in sequence i) is selected from D, H and Q.

In one embodiment, $X_{18}$ in sequence i) is selected from H and Q.

In one embodiment, $X_{18}$ in sequence i) is H.

In one embodiment, $X_{18}$ in sequence i) is Q.

In one embodiment, $X_{18}$ in sequence i) is D.

In one embodiment, $X_{20}$ in sequence i) is selected from K and R.

In one embodiment, $X_{20}$ in sequence i) is selected from H and R.

In one embodiment, $X_{20}$ in sequence i) is R.

In one embodiment, $X_{20}$ in sequence i) is K.

In one embodiment, $X_{21}$ in sequence i) is selected from I and L.

In one embodiment, $X_{21}$ in sequence i) is I.

In one embodiment, $X_{21}$ in sequence i) is L.

In one embodiment, $X_{25}$ in sequence i) is selected from I, L and V.

In one embodiment, $X_{25}$ in sequence i) is selected from V and I.

In one embodiment, $X_{25}$ in sequence i) is I.

In one embodiment, $X_{25}$ in sequence i) is V.

In one embodiment, $X_{25}$ in sequence i) is L.

In one embodiment, $X_{26}$ in sequence i) is K.

In one embodiment, $X_{28}$ in sequence i) is D.

In one embodiment, sequence i) is defined as follows: independently from each other,
$X_2$ is selected from F and L;
$X_3$ is selected from H, K, R, T and V;
$X_4$ is selected from A, H, I, L, N, V and W;
$X_6$ is selected from F and L;
$X_7$ is selected from K, L, N, Q, R and S;
$X_{10}$ is selected from H, K, N and R;
$X_{11}$ is selected from A, F, L, R, T, and Y;
$X_{16}$ is T;
$X_{17}$ is selected from F, H and L;
$X_{18}$ is selected from D, H, I, K and Q;
$X_{20}$ is selected from H and R;
$X_{21}$ is selected from I and L;
$X_{25}$ is selected from I, L and V;
$X_{26}$ is K; and
$X_{28}$ is D.

In one embodiment, sequence i) is defined as follows: independently from each other,
$X_2$ is selected from F and L;
$X_3$ is selected from H, K, T and V;
$X_4$ is selected from H, L, N, and V;
$X_6$ is selected from F and L;
$X_7$ is selected from K, R, Q, and S;
$X_{10}$ is selected from H, K, and N;
$X_{11}$ is selected from A, F, T and Y;
$X_{16}$ is T;
$X_{17}$ is selected from F, H and L;
$X_{18}$ is selected from D, H and Q;
$X_{20}$ is R;
$X_{21}$ is selected from I and L;
$X_{25}$ is selected from I, L and V;
$X_{26}$ is K; and
$X_{28}$ is D.

In a more specific embodiment defining a sub-class of the ABD binding polypeptide, sequence i) fulfills at least four of the eight conditions I-VIII:

I. $X_2$ is selected from F and L;
II. $X_6$ is selected from F and L;
III. $X_{16}$ is T;
IV. $X_{20}$ is selected from H and R;
V. $X_{21}$ is selected from I and L;
VI. $X_{25}$ is selected from I and V;
VII. $X_{26}$ is K; and
VIII. $X_{28}$ is D.

In some examples of an ABD binding polypeptide for use in the disclosed separation method, sequence i) fulfils at least five of the eight conditions I-VIII. More specifically, sequence i) may fulfill at least six of the eight conditions I-VIII, such at least seven of the eight conditions I-VIII, such as all of the eight conditions I-VIII.

As described in detail in the experimental section to follow, the selection of ABD binding polypeptide variants has led to the identification of a number of individual ABD binding motif (BM) sequences. These sequences constitute individual embodiments of sequence i). The sequences of individual ABD binding motifs are presented in FIG. 1A-1F and as SEQ ID NO:1-52. In some embodiments of this aspect, sequence i) is selected from any one of SEQ ID NO:1-52. More specifically, sequence i) may be selected from any one of SEQ ID NO:1-7, such as from SEQ ID NO:1, SEQ ID NO:2, SEQ ID NO:3 and SEQ ID NO:4. In particular, sequence i) may be SEQ ID NO:1.

In some embodiments of the present disclosure, the BM as defined above "forms part of" a three-helix bundle protein domain. This is understood to mean that the sequence of the BM is "inserted" into or "grafted" onto the sequence of the original three-helix bundle domain, such that the BM replaces a similar structural motif in the original domain. For example, without wishing to be bound by theory, the BM is thought to constitute two of the three helices of a three-helix bundle, and can therefore replace such a two-helix motif within any three-helix bundle. As the skilled person will realize, the replacement of two helices of the three-helix bundle domain by the two BM helices has to be performed so as not to affect the basic structure of the polypeptide. That is, the overall folding of the Cα backbone of the polypeptide according to this embodiment of the invention is substantially the same as that of the three-helix bundle protein domain of which it forms a part, e.g. having the same elements of secondary structure in the same order etc. Thus, a BM according to the invention "forms part" of a three-helix bundle domain if the polypeptide according to this embodiment of the invention has the same fold as the original domain, implying that the basic structural properties are shared, those properties e.g. resulting in similar CD spectra. The skilled person is aware of other parameters that are relevant.

In particular embodiments, the ABD binding motif (BM) thus forms part of a three-helix bundle protein domain. For example, the BM may essentially constitute two alpha helices with an interconnecting loop, within said three-helix bundle protein domain. In particular embodiments, said three-helix bundle protein domain is selected from domains of bacterial receptor proteins. Non-limiting examples of such domains are the five different three-helical domains of Protein A from *Staphylococcus aureus*, such as domain B, and derivatives thereof. In some embodiments, the three-helical bundle protein domain is a variant of protein Z, which is derived from domain B of staphylococcal protein A.

In embodiments where the ABD binding polypeptide for use in the disclosed separation method forms part of a three-helix bundle protein domain, the ABD binding polypeptide may comprise an amino acid sequence selected from:

iii) (SEQ ID NO: 167)
K-[*BM*]-DPSQS $X_aX_b$LL$X_c$ EAKKL ND$X_d$Q;

wherein

[BM] is an ABD binding motif as defined above;
$X_a$ is selected from A and S;
$X_b$ is selected from N and E;
$X_c$ is selected from A, S and C;
$X_d$ is selected from A and S;

and iv) an amino acid sequence which has at least 81% identity to a sequence defined by iii).

As discussed above, use of polypeptides comprising minor changes as compared to the above amino acid sequences without largely affecting the tertiary structure and the function thereof are also within the scope of the present disclosure. Thus, in some embodiments, sequence iv) has at least 83%, such as at least 85%, such as at least 87%, such as at least 89%, such as at least 91%, such as at least 93%, such as at least 95%, such as at least 97% identity to a sequence defined by iii).

In one embodiment of the ABD binding polypeptide for use in the disclosed separation method, $X_a$ in sequence iii) is A. In an alternative embodiment, $X_a$ in sequence iii) is S.

In one embodiment of the ABD binding polypeptide for use in the disclosed separation method, $X_b$ in sequence iii) is N. In an alternative embodiment, $X_b$ in sequence iii) is E.

In one embodiment of the ABD binding polypeptide for use in the disclosed separation method, $X_c$ in sequence iii) is A. In an alternative embodiment, $X_c$ in sequence iii) is S. In yet another alternative embodiment, $X_c$ in sequence iii) is C.

In one embodiment of the ABD binding polypeptide for use in the disclosed separation method, $X_d$ in sequence iii) is A. In an alternative embodiment, $X_d$ in sequence iii) is S.

In one embodiment of the ABD binding polypeptide for use in the disclosed separation method, in sequence iii), $X_a$ is A; $X_b$ is N; $X_c$ is A and $X_d$ is A.

In a further embodiment of the ABD binding polypeptide for use in the disclosed separation method, in sequence iii), $X_a$ is A; $X_b$ is N; $X_c$ is C and $X_d$ is A.

In a further embodiment of the ABD binding polypeptide for use in the disclosed separation method, in sequence iii), $X_a$ is S; $X_b$ is E; $X_c$ is S and $X_d$ is S.

In a further embodiment of the ABD binding polypeptide for use in the disclosed separation method, in sequence iii), $X_a$ is S; $X_b$ is E; $X_c$ is C and $X_d$ is S.

In a further embodiment of the ABD binding polypeptide for use in the disclosed separation method, in sequence iii), $X_a$ is S; $X_b$ is E; $X_c$ is A and $X_d$ is A.

In a further embodiment of the ABD binding polypeptide for use in the disclosed separation method, in sequence iii), $X_a$ is S; $X_b$ is E; $X_c$ is C and $X_d$ is A.

In yet a further embodiment, sequence iii) in the definition of ABD binding polypeptides above is selected from SEQ ID NO:53-104, in particular from SEQ ID NO:53-59. In a further embodiment, sequence iii) is selected from SEQ ID NO:53, SEQ ID NO:54, SEQ ID NO:55 and SEQ ID NO:56. In particular, sequence iii) may be SEQ ID NO:53.

Also, in a further embodiment, there is provided use in the disclosed separation method of an ABD binding polypeptide as defined above, which comprises an amino acid sequence selected from:

v) (SEQ ID NO: 168)
YAK-[*BM*]-DPSQS SELL$X_c$ EAKKL NDSQA P;

wherein [BM] is an ABD binding motif as defined above and $X_c$ is selected from S and C; and vi) an amino acid sequence which has at least 83% identity to a sequence defined by v).

In another embodiment, there is provided use in the disclosed separation method of an ABD binding polypeptide as defined above, which comprises an amino acid sequence selected from:

vii) (SEQ ID NO: 169)
YAK-[*BM*]-DPSQS SELL$X_c$ EAKKL NDAQA P;

wherein [BM] is an ABD binding motif as defined above and $X_c$ is selected from A and C; and viii) an amino acid sequence which has at least 83% identity to a sequence defined by vii).

Alternatively, there is provided use in the disclosed separation method of an ABD binding polypeptide as defined above, which comprises an amino acid sequence selected from:

ix)

```
                                          (SEQ ID NO: 170)
    FNK-[BM]-DPSQS ANLLX_c EAKKL NDAQA P;
``` wherein [BM] is an ABD binding motif as defined above and $X_c$ is selected from A and C; and x) an amino acid sequence which has at least 83% identity to a sequence defined by ix).

As discussed above, use of polypeptides comprising minor changes as compared to the above amino acid sequences without largely affecting the tertiary structure and the function thereof are also within the scope of the present disclosure. Thus, in some embodiments, the ABD binding polypeptides as defined above may for example have a sequence which is at least 84%, at least 86%, at least 88%, at least 90%, at least 92%, at least 94%, at least 96%, or at least 98% identical to a sequence defined by v), vii) or ix).

In some embodiments, the ABD binding motif may form part of a polypeptide comprising an amino acid sequence selected from

```
                                          (SEQ ID NO: 171)
    ADNNFNK-[BM]-DPSQSANLLSEAKKLNESQAPK;

(SEQ ID NO: 172)
    ADNKFNK-[BM]-DPSQSANLLAEAKKLNDAQAPK;

(SEQ ID NO: 173)
    ADNKFNK-[BM]-DPSVSKEILAEAKKLNDAQAPK;

(SEQ ID NO: 174)
    ADAQQNNFNK-[BM]-DPSQSTNVLGEAKKLNESQAPK;

(SEQ ID NO: 175)
    AQHDE-[BM]-DPSQSANVLGEAQKLNDSQAPK;

(SEQ ID NO: 176)
    VDNKFNK-[BM]-DPSQSANLLAEAKKLNDAQAPK;

(SEQ ID NO: 177)
    AEAKYAK-[BM]-DPSESSELLSEAKKLNKSQAPK;

(SEQ ID NO: 178)
    VDAKYAK-[BM]-DPSQSSELLAEAKKLNDAQAPK;

(SEQ ID NO: 179)
    VDAKYAK-[BM]-DPSQSSELLAEAKKLNDSQAPK;

(SEQ ID NO: 180)
    AEAKYAK-[BM]-DPSQSSELLSEAKKLNDSQAPK;

(SEQ ID NO: 181)
    VDAKYAK-[BM]-DPSQSSELLSEAKKLNDSQAPK;

(SEQ ID NO: 182)
    VDAKYAK-[BM]-DPSQSSELLAEAKKLNKAQAPK;
    and (SEQ ID NO: 183)
    AEAKYAK-[BM]-DPSQSSELLAEAKKLNKAQAPK.
```

In one embodiment, the ABD binding polypeptide for use in the disclosed separation method comprises an amino acid sequence selected from:

xi)
```
                                          (SEQ ID NO: 184)
    VDAKYAK-[BM]-DPSQSSELLAEAKKLNDAQAPK;
``` wherein [BM] is an ABD binding motif as defined above; and xii) an amino acid sequence which has at least 84% identity to the sequence defined in xi).

Again, use of polypeptides comprising minor changes as compared to the above amino acid sequences without largely affecting the tertiary structure and the function thereof are also within the scope of the present disclosure. Thus, in some embodiments, the ABD binding polypeptides as defined above may for example have a sequence which is at least 86%, at least 87%, at least 89%, at least 91%, at least 93%, at least 94%, at least 96%, or at least 98% identical to the sequence defined by xi).

Sequence xi) in such a polypeptide may be selected from any one of SEQ ID NO:105-156. In particular, sequence xi) may be selected from any one of SEQ ID NO:105-111, such as selected from SEQ ID NO:105, SEQ ID NO:106, SEQ ID NO:107 and SEQ ID NO:108. In a specific embodiment of this polypeptide, sequence xi) is SEQ ID NO:105.

The polypeptide for use in the disclosed separation method may be in monomeric or multimeric forms. In one embodiment, the ABD binding polypeptide is present in multimeric form, comprising at least two ABD binding polypeptide monomer units, whose amino acid sequences may be the same or different. Multimeric forms of the polypeptide may be advantageous in that they may have enhanced binding properties.

In one embodiment, said ABD binding polypeptide monomer units are covalently coupled together. In a particular embodiment, the ABD binding polypeptide monomer units are expressed as a fusion protein.

The polypeptides may be joined by covalent coupling using known organic chemistry methods, or expressed as one or more fusion polypeptides in a system for recombinant expression of polypeptides, or joined in any other fashion, either directly or via a linker, for example an amino acid linker.

In one embodiment, said ABD binding polypeptide is in dimeric form. Possible multimeric forms also include trimeric forms. Multimeric forms of the polypeptide may comprise a suitable number of polypeptide sequences as defined above.

The skilled person will understand that various modifications and/or additions can be made to an ABD binding polypeptide according to any aspect disclosed herein in order to tailor the polypeptide to a specific application without departing from the scope of the present disclosure. For example, any ABD binding polypeptide disclosed herein may comprise further C-terminal and/or N-terminal amino acids. Such a polypeptide should be understood as a polypeptide having additional amino acid residues at the very first and/or the very last position in the polypeptide chain, i.e. at the N- and/or C-terminus. Thus, an ABD binding polypeptide may comprise any suitable number of additional amino acid residues, for example at least one additional amino acid residue. Each additional amino acid residue may individually or collectively be added in order to, for example, improve production, purification, stabilization in vivo or in vitro, coupling, or detection of the polypeptide. Such additional amino acid residues may comprise one or more amino acid residues added for the purpose of chemical coupling, which could for example allow coupling of the ABD binding polypeptide to a resin or matrix, for example a Sepharose-based resin or a SulfoLink coupling resin. One example of this is the addition of a cysteine residue as an additional amino acid residue, or as one of a number of additional amino acid residues. In one embodiment, the ABD binding polypeptide disclosed herein comprises a cysteine residue at the C-terminal end of the polypeptide, for example at the C-terminus. In one embodiment, said cysteine is a part of a C-terminal additional tripeptide VDC. In one embodiment, said cysteine is a lone C-terminal C.

In one particularly specific embodiment, the ABD binding polypeptide comprises a dimer of two ABD binding domains as defined above, as well as a C-terminal cysteine residue.

Such additional amino acid residues may also provide a "tag" for purification or detection of the polypeptide, such as a $His_6$ tag or a "myc" (c-myc) tag or a "FLAG" tag for interaction with antibodies specific to the tag or immobilized metal affinity chromatography (IMAC) in the case of the $His_6$-tag.

The further amino acids as discussed above may be coupled to the ABD binding polypeptide by means of chemical conjugation (using known organic chemistry methods) or by any other means, such as expression of the ABD binding polypeptide as a fusion protein.

While the invention has been described with reference to various exemplary embodiments, it will be understood by those skilled in the art that various changes may be made and equivalents may be substituted for elements thereof without departing from the scope of the invention. In addition, many modifications may be made to adapt a particular situation or molecule to the teachings of the invention without departing from the essential scope thereof. Therefore, it is intended that the invention not be limited to any particular embodiment contemplated for carrying out this invention, but that the invention will include all embodiments falling within the scope of the appended claims.

BRIEF DESCRIPTION OF THE FIGURES

FIG. 1A-1F is a listing of the amino acid sequences of examples of ABD binding motifs comprised in ABD binding polypeptides of the invention (SEQ ID NO:1-52), examples of 49-mer ABD binding polypeptides according to the invention (SEQ ID NO:53-104), examples of 58-mer ABD binding polypeptides according to the invention (SEQ ID NO:105-156) as well as the sequences of albumin binding domain variants (SEQ ID NO:157-162) used for selection and screening, or used in fusion proteins for illustration of the invention.

FIG. 5A represents the relative amounts of sample released from each of the ABD binding Z variant-coupled resins, or from an HSA-Sepharose resin included as a reference, after a first (a) or second (b) elution with 0.1 M sodium citrate, pH 3.0 or 0.5 M HAc, pH 2.5, respectively. FIG. 5B shows the result of SDS-PAGE analysis of the corresponding fractions eluted from the Z variant-coupled resin in FIG. 5A. "M" refers to Novex Sharp Pre-stained Protein standard (Invitrogen; Mw: 216, 160, 110, 80, 60, 50, 40, 30, 20, 15, 10, 3.5 kDa) and "Loaded sample" refers to the bacterial extract, containing PEP08515, initially loaded on each Z variant-coupled resin. 20 μl of the eluate from the Z variant-coupled resins, 5 μl of protein standard or bacterial extract were loaded in one lane each of the SDS-PAGE gel. FIG. 5C shows the result of SDS-PAGE analysis of the corresponding fractions eluted from HSA Sepharose resin in FIG. 5A. Lane 1: First elution with 0.1 M sodium citrate, pH 3.0 (pH 3 (a)). Lane 2: Second elution with 0.1 M sodium citrate, pH 3.0 (pH 3 (b)). Lane 3: First elution with 0.5 M HAc, pH 2.5 (pH 2.5 (a)). Lane 4: Second elution with 0.5 M HAc, pH 2.5 (pH 2.5 (b)). 20 μl of each eluate were loaded on the SDS-PAGE gel. "M" refers to Novex Sharp Pre-stained Protein standard (Invitrogen; Mw: 216, 160, 110, 80, 60, 50, 40, 30, 20, 15, 10, 3.5 kDa) of which 5 μl were loaded.

EXAMPLES

Figure 2:
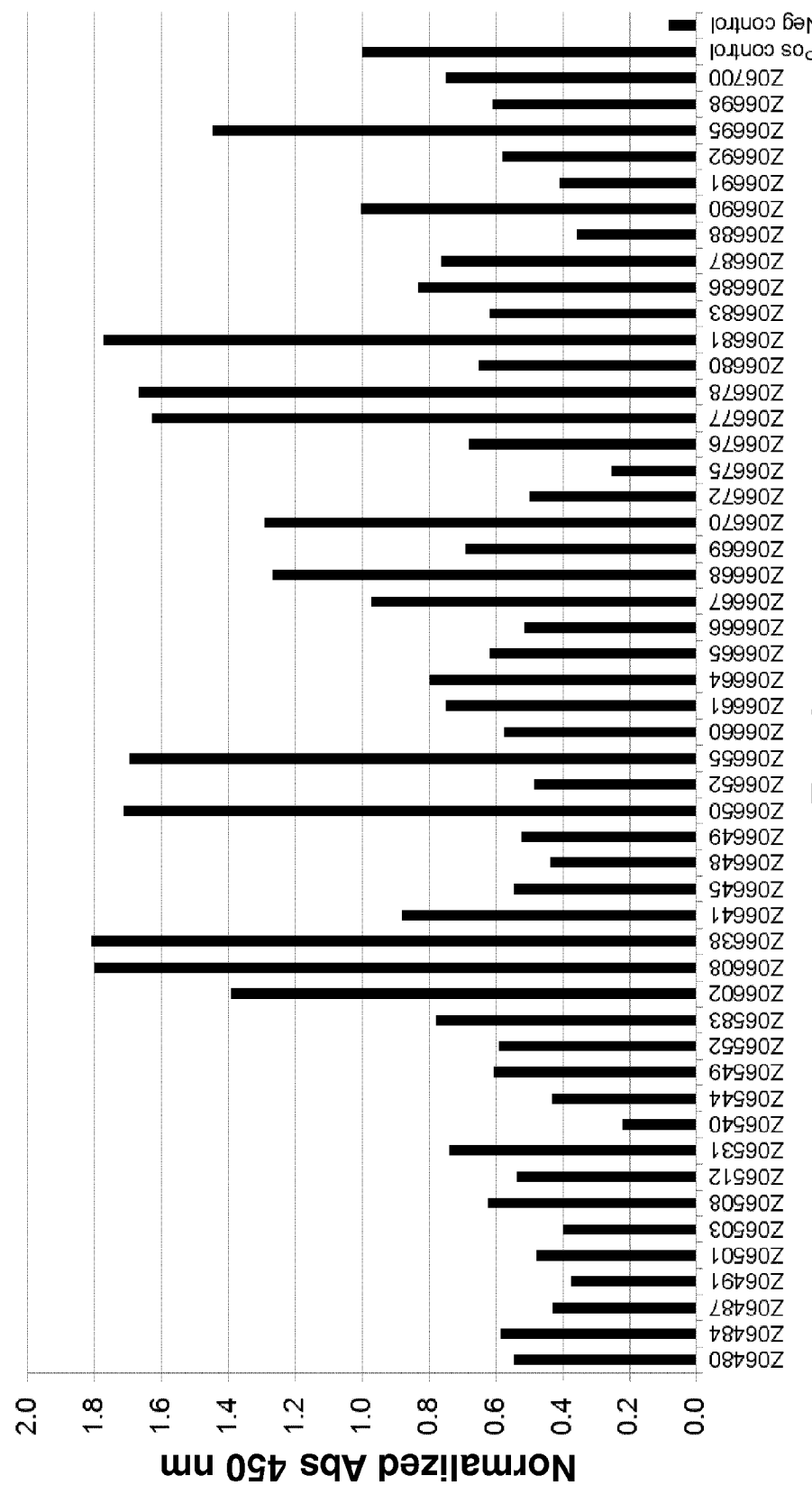
FIG. 2 shows the response in ELISA for a selection of Z variants assayed with 2 μg/ml of biotinylated PEP07911, as described in Example 1. The responses were normalized by dividing the absorbances with the signal from the positive control on the ELISA plate.

The following materials where used throughout this work except where otherwise noted:

Escherichia coli strain XL1-Blue (Agilent Technologies, cat. no. 200268)

Albumin binding domains ABD001 (SEQ ID NO:157), C-ABD001 (SEQ ID NO:158), ABD035 (SEQ ID NO:159), PP013 (SEQ ID NO:160), PEP07986 (SEQ ID NO:161) and PEP07911 (SEQ ID NO:162), produced essentially as described in WO2009/016043 or WO2012/004384.

Example 1

Selection and Screening of ABD Binding Z Variants

Materials and Methods

Biotinylation of Target Protein:

ABD001 with an N-terminal cysteine (C-ABD001; SEQ ID NO:158) and PEP07911 (SEQ ID NO:162) were biotinylated using EZ-Link Maleimide PEG$_2$-Biotin (Pierce, cat. no. 21901). In brief, protein was dissolved in 50 mM sodium phosphate, 150 mM NaCl, 2 mM EDTA, pH 7.5. Dithiothreitol (DTT) was added to a final concentration of 20 mM and the samples were incubated for 1 h at 34° C. with end-over-end mixing. The buffer was exchanged to conjugation buffer (50 mM sodium phosphate, 150 mM NaCl, 1 mM EDTA, pH 7.0) using disposable PD-10 columns (GE Healthcare, cat. no. 17-0851-01). A five times (5×) molar excess of EZ-Link Maleimide PEG$_2$-Biotin (dissolved in conjugation buffer) was added to the protein samples and incubation proceeded for 2 h at room temperature (RT) with end-over-end mixing. Subsequent buffer exchange to PBS (10 mM phosphate, 137 mM NaCl, 2.68 mM KCl, pH 7.4) was performed using PD-10 columns. PEP07986 (SEQ ID NO:161) was biotinylated according to the manufacturer's recommendations at RT for 30 min using No-Weigh EZ-Link Sulfo-NHS-LC-Biotin (Pierce, cat. no. 21327) at a 10× molar excess. Subsequent buffer exchange to PBS was performed using a dialysis cassette (Slide-a-lyzer 3.5 K, 3500 MWCO, Pierce, cat. no. 66333) according to the manufacturer's instructions.

Phage Display Selection of ABD Binding Z Variants:

A library of random variants of protein Z displayed on bacteriophage, constructed in phagemid pAY02047 essentially as described in Gronwall et al (J Biotechnol, 128:162-183, 2007), was used to select ABD binding polypeptides.

The library, Zlib004Naive.I, utilizes the Taq DNA polymerase binding molecule Z03639 (described in Gunneriusson et al, Protein Eng 12:873-878, 1999, where it was denoted $Z_{TaqS1-1}$) as fusion partner. The library had an actual size of $1.4 \times 10^{10}$ variants.

Phage stocks were prepared in a 20 l fermenter. Cells from a glycerol stock containing the phagemid library Zlib004Naive.I were inoculated in 20 l of TSB-YE (Tryptic Soy Broth-Yeast Extract; 30 g/l TSB, 5 g/l yeast extract) supplemented with 2% glucose and 100 µg/ml ampicillin. The cultivations were grown at 37° C. in a fermenter (Belach Bioteknik, BR20). When the cells reached an optical density (OD) of 0.7-0.8, approximately 2.6 l of the cultivation was infected using a 10× molar excess of M13K07 helper phage (New England Biolabs, cat. no. NO3155). The cells were incubated for 30 min, whereupon the fermenter was filled up to 20 l with TSB-YE supplemented with 0.1 mM IPTG (isopropyl-β-D-1-thiogalactopyranoside, for induction of expression), 25 µg/ml kanamycin and 12.5 µg/ml carbenicillin, and cells were grown at 30° C. for 22 h. The cells in the cultivation were pelleted by centrifugation at 15900 g and the phage particles remaining in the medium were precipitated twice in PEG/NaCl (polyethylene glycol/sodium chloride), filtered and dissolved in PBS and glycerol as described in Gronwall et al, supra. Phage stocks were stored at −80° C. before use.

Selections were performed in three cycles against the different variants of biotinylated ABD. Phage stock preparation, selection procedure and amplification of phage between selection cycles were performed essentially as described for selection against another target in WO2009/077175. PBS supplemented with 0.1% gelatine and 0.1% Tween20 was used as selection buffer and the target-phage complexes were directly captured by Dynabeads® M-280 Streptavidin (Dynal, cat. no. 112.06). 1 mg beads per 0.25 µg ABD was used. E. coli strain XL1-Blue was used for phage amplification. Selection was performed in three cycles divided into three tracks: one track using PEP07911, one track using C-ABD001 and one track alternating between C-ABD001 and PEP07986. In cycle 1 of the selections, 100 nM PEP07911 or C-ABD001 was used in the different selection tracks, and two washes with PBST 0.1% (PBS supplemented with 0.1% Tween-20) were performed. An increased stringency, using a lowered target concentration and an increased number of washes, was applied in the subsequent two cycles. For the selection tracks with only one target, 50 nM followed by 25 nM PEP07911 or C-ABD001, were used in cycle 2 and 3, respectively. In the track with alternating target, 75 nM PEP07986 was used in cycle 2 and 40 nM C-ABD001 was used in cycle 3. For all tracks, 4 and 8 washes were performed in cycle 2 and 3, respectively, using PBST 0.1%. After the wash, the bound phages were eluted with 500 µl 0.1 M glycine-HCl, pH 2.2 followed by immediate neutralization with 50 µl Tris-HCl, pH 8.0 and 450 µl PBS. In the last selection cycle, all tracks were first eluted with 0.5 M HAc, pH 4.0, followed by elution with glycine-HCl as described above. The different eluates were thereafter treated separately.

ELISA Screening of Z Variants:

To verify that the selected Z variant molecules could indeed interact with different variants of ABD, ELISA assays were performed. The Z variants were produced by inoculating single colonies from the selections into 1 ml TSB-YE medium supplemented with 100 µg/ml ampicillin and 0.1 mM IPTG in deep-well plates (Nunc, cat. no. 278752). The plates were incubated for 18-24 h at 37° C. Cells were pelleted by centrifugation, re-suspended in 400 µl PBST 0.05% and frozen at −80° C. to release the periplasmic fraction of the cells. Frozen samples were subsequently thawed in a water bath and the freeze-thawing was repeated eight times. 400 µl PBST 0.05% was added to the samples and cells were pelleted by centrifugation. The periplasmic supernatant contained the Z variants as fusions to the Taq DNA polymerase binding molecule Z03639, expressed as AQHDEALE-[Z#####]-VDYV-[Z03639]-YVPG (SEQ ID NO: 185). Z##### refers to individual 58 amino acid residue Z variants.

Half-area 96-well ELISA plates (Costar, cat. no. 3690) were coated with 50 µl/well of coating buffer (50 mM sodium carbonate, pH 9.6) containing 4 µg/ml of an antibody specific for Z variants (Affibody, cat. no. 20.1000.01.0005) and incubated over-night at 4° C. The antibody solution was poured off and the wells were blocked with 100 µl of PBSC (PBS supplemented with 0.5% casein; Sigma, cat. no. C8654) for 2 h at RT. The blocking solution was discarded and 50 µl periplasmic solution was added to the wells and incubated for 1.5 h at RT under slow shaking. The supernatants were poured off and the wells were washed 4 times with PBST 0.05%. Then, 50 µl of biotinylated PEP07986 or PEP07911, at a concentration of 2 µg/ml in PBSC, was added to each well. The plates were incubated for 1 h at RT followed by washes as described above. Streptavidin-HRP (Horseradish peroxidase; Thermo Scientific, cat. no. N100) diluted 1:30 000 in PBSC, was added to the wells and the plates were incubated for 45 min. After washing as described above, 50 µl ImmunoPure TMB substrate (Thermo Scientific, cat. no. 34021) was added to the wells and the plates were treated according to the manufacturer's recommendations. Absorbance of the wells was measured at 450 nm using a multi-well plate reader, Victor$^3$ (Perkin Elmer).

As positive control, a periplasmic fraction containing a Z variant binding to an irrelevant but specified target protein and expressed as above was assayed against 5 µg/ml of this target protein, biotinylated. As negative control, the same periplasmic preparation was assayed against PEP07986 or PEP07911. Sequencing was performed for the clones with positive absorbance values against PEP07986 or PEP07911.

Sequencing:

PCR fragments were amplified in two steps from single colonies using a standard PCR program and the primers AFFI-21 (5'-tgcttccggctcgtatgttgtgtg; SEQ ID NO:163) and AFFI-22 (5'-cggaaccagagccaccaccgg; SEQ ID NO:164). Sequencing of amplified fragments was performed using the biotinylated oligonucleotide AFFI-72 (5'-biotin-cggaaccagagccaccaccgg; SEQ ID NO:165) and a BigDye® Terminator v3.1 Cycle Sequencing Kit (Applied Biosystems, cat. no. 4336919), used in accordance with the manufacturer's protocol. The sequencing reactions were purified by binding to magnetic streptavidin coated beads (Detach Streptavidin Beads, Nordiag, cat. no. 2012-01) using a Magnatrix 8000 (Magnetic Biosolution) and analyzed on ABI PRISM® 3130xl Genetic Analyzer (PE Applied Biosystems).

Blocking ELISA:

A subset of clones from the initial ELISA screen were subjected to an ELISA blocking assay in order to elucidate if their target binding was affected by the presence of HSA. For the selected Z variants, the same periplasmic fractions as above were used. The ELISA blocking assay was run as the ELISA screening assay, with the following protocol modification introduced at the target step: HSA was mixed with the target protein before addition to the assay plate. 0.2 µg/ml of biotinylated PEP07911 was mixed with a 10× molar excess of HSA and then incubated for 15 min at RT to allow complex formation before addition to the plate. As positive control, a periplasmic fraction containing a molecule binding an irrelevant target protein and expressed as above was assayed against 5 μg/ml biotinylated specific target protein. As negative control, the same periplasmic preparation was assayed against biotinylated PEP07911. As blank, PBSC was added instead of periplasmic preparation and biotinylated PEP07911 added as target. All controls were prepared as samples with and without addition of HSA in the same manner as above.

Results

Phage Display Selection of ABD Binding Z Variants:

Individual clones were obtained after three cycles of phage display selections against different variants of biotinylated ABD. The phage particle yield (phage particles out/phage particles in) increased for each cycle, indicating enrichment in target binding clones.

ELISA Screening of Z Variants:

The clones obtained after three cycles of selection were produced in 96-well plates and screened for ABD binding activity in ELISA. The results of a selection of the positive clones (signals corresponding to at least 2× the negative control) assayed against PEP07911 are presented in FIG. 2. The control molecule specific for an irrelevant protein gave a positive signal for the specific protein, whereas no signal was obtained against PEP07986 or PEP07911.

Figure 3:
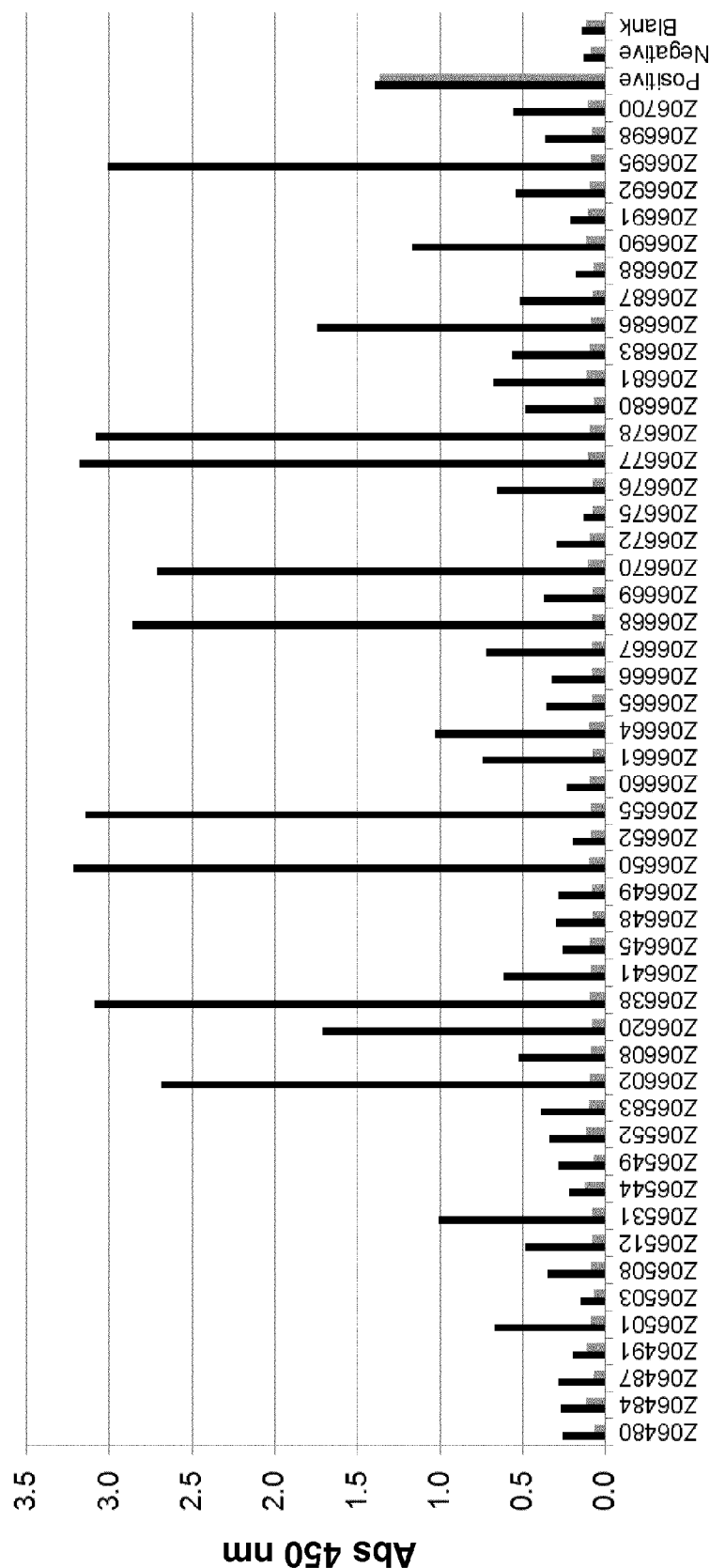
FIG. 3 shows the response for a selection of Z variants in a blocking ELISA assay, performed as described in Example 1. Periplasm preparations of Z variants were tested against 0.2 μg/ml PEP07911 with or without the addition of 10× excess HSA. Black bars correspond to samples without HSA and grey bars to samples with HSA added as blocking agent.

Blocking ELISA:

Clones positive for PEP07986 or PEP07911 were subjected to a blocking assay including HSA, to see if the Z variants had overlapping binding sites with the natural ligand HSA. For all tested clones, the binding signal to PEP07911 was completely extinguished by the presence of HSA, reaching the same level as the background (FIG. 3). The binding of the positive control was not affected by addition of an excess of HSA and the blank showed no background signal.

Sequencing:

Sequencing was performed for the clones with positive absorbance values against ABD in the ELISA screening. Each variant was given a unique identification number #####, and individual variants are referred to as Z#####. The amino acid sequences of the 58 amino acid residues long Z variants are listed in FIG. 1A-1F and in the sequence listing as SEQ ID NO:105-156 The deduced ABD binding motifs of these Z variants are denoted BM##### and listed in FIG. 1A-1F and in the sequence listing as SEQ ID NO:1-52. The amino acid sequences of the 49 amino acid residues long polypeptides predicted to constitute the complete three-helix bundle within each of these Z variants are denoted P##### and listed in FIG. 1A-1F and in the sequence listing as SEQ ID NO:53-104.

Example 2

Cloning and Production of ABD Binding Z Variants

Materials and Methods

Subcloning of Z Variants:

The DNA of seven ABD binding Z variants, Z06608 (SEQ ID NO:107), Z06620 (SEQ ID NO:110), Z06638 (SEQ ID NO:106), Z06650 (SEQ ID NO:108), Z06677 (SEQ ID NO:105), Z06678 (SEQ ID NO:109) and Z06695 (SEQ ID NO:111), were amplified from the library vector pAY02047. A subcloning strategy for construction of dimeric Z variant molecules with N-terminal His$_6$ tag and C-terminal Cys was applied using standard molecular biology techniques and as described in detail in WO 2009/077175 for Z variants binding another target. The Z gene fragments were subcloned into the expression vector pAY01449 resulting in the encoded sequence MGSSHHH-HHHLQ-[Z#####][Z#####]-VDC (SEQ ID NO: 186).

Cultivation and Purification:

E. coli BL21 (DE3) cells (Novagen) were transformed with plasmids containing the dimeric gene fragment of each respective Z variant and cultivated at 37° C. in 1 l of TSB+YE medium (Tryptic Soy Broth with Yeast Extract) supplemented with 50 μg/ml kanamycin. At OD$_{600}$=1, IPTG was added to induce protein expression at a final concentration of 0.17 mM and the cultivation was incubated at 37° C. for another 5 h. The cells were harvested by centrifugation.

4.8 g of each cell pellet were re-suspended in 30 ml of denaturing binding buffer (20 mM sodium phosphate, 0.5 M NaCl, 20 mM imidazole, 8 M urea, pH 7.4) supplemented with 29 U/ml Benzonase® (Merck, cat. no. 1.01654.0001) and incubated with agitation at RT for 1 h to release the expressed protein. Cell debris was removed by centrifugation and each supernatant was applied on a 1 ml His GraviTrap IMAC column (GE Healthcare, cat. no. 11-0033-99). Contaminants were removed by washing with denaturing binding buffer, native binding buffer (20 mM sodium phosphate, 0.5 M NaCl, 20 mM imidazole, pH 7.4) and wash buffer (20 mM sodium phosphate, 0.5 M NaCl, 60 mM imidazole, pH 7.4) and the ABD binding Z variants were subsequently eluted with elution buffer (20 mM sodium phosphate, 0.5 M NaCl, 250 mM imidazole, pH 7.4). Each purified ABD binding Z variant was transferred to 10 mM NH$_4$HCO$_3$ by size exclusion chromatography. Protein concentrations were determined by measuring the absorbance at 280 nm, using a NanoDrop® ND-1000 spectrophotometer, and using the extinction coefficient of the respective protein. The ABD binding Z variants were lyophilized and the purity of the final products was analyzed by SDS-PAGE stained with Coomassie Blue. The identity of each purified ABD binding Z variant was confirmed using HPLC-MS analysis.

Results

Cultivation and Purification:

The seven ABD binding Z variants Z06608 (SEQ ID NO:107), Z06620 (SEQ ID NO:110), Z06638 (SEQ ID NO:106), Z06650 (SEQ ID NO:108), Z06677 (SEQ ID NO:105), Z06678 (SEQ ID NO:109) and Z06695 (SEQ ID NO:111), constructed as dimers and with an N-terminal His$_6$ tag and a C-terminal Cys, expressed well in E. coli. The amount of IMAC-purified protein from 4.8 g bacterial pellets, determined spectrophotometrically by measuring the absorbance at 280 nm, ranged from 3 mg to 19 mg for the different ABD binding Z variants.

SDS-PAGE analysis of each final protein preparation showed that these predominantly contained respective ABD binding Z variant. The correct molecular weight of each ABD binding Z variant was confirmed by HPLC-MS.

Example 3

Assessment of Binding and Elution Characteristics of ABD Binding Z Variants

In this Example, the binding and elution characteristics of a set of ABD binding polypeptides, selected and produced as described in Example 1 and 2, respectively, were studied in a small-scale format using spin columns.

Materials and Methods

Coupling of the ABD Binding Z Variants to Resin:

1 mg of each lyophilized ABD binding Z variant Z06608, Z06620, Z06638, Z06650, Z06677, Z06678 and Z06695, in the format $His_6$-(Z#####)$_2$-Cys produced as described in Example 2, was resuspended in a reducing buffer (50 mM Tris-HCl, 5 mM EDTA, 20 mM DTT, pH 8.5) and incubated at RT for 2 h. Reduced protein solutions were transferred to a coupling buffer (50 mM Tris-HCl, 5 mM EDTA, pH 8.5) including 50 mM DTT, using size exclusion chromatography, and then mixed with portions of 0.2 ml SulfoLink Coupling Resin (Thermo Fisher Scientific, cat. no. 20401). This procedure enables site-directed reaction between the thiol groups of the C-terminal cysteine residues of the ABD binding Z variants and the iodoacetyl groups of the resin, forming a covalent thioether bond. The coupling reaction was carried out according to the instructions by the manufacturer. The degree of coupling, defined as mg of coupled ABD binding Z variant per ml of resin, was determined as follows: The amount of coupled ABD binding Z variant was calculated by subtracting the amount of uncoupled material from the original amount of sample, based on concentrations obtained by spectrophotometric measurements of the absorbance at 280 nm. The amount of coupled ABD binding Z variant in mg was then divided with the volume of the SulfoLink Coupling Resin.

Column Study I: Assessment of ABD Binding Z Variant-Coupled Resins Using a Pure Sample:

A first column study was performed to test binding, wash and elution properties of each of the seven ABD binding Z variants coupled to resin and by using a previously purified sample of the ABD fusion protein PEP08517. PEP08517 comprises the albumin binding domain PP013 (SEQ ID NO:160) fused at its N-terminus to a cytokine binding variant of protein Z. 0.1 ml portions of the resins were transferred to test tubes and 0.1 ml of a pure sample of PEP08517 at 2 mg/ml in coupling buffer was added. The tubes were incubated on a rotating wheel for 1 h at RT. Each sample-resin mix was transferred to an empty spin column. Unbound protein was collected by centrifugation (flow-through, FT). 0.1 ml of different solutions, specified in Table 1, were thereafter added to wash and subsequently elute bound PEP08517 molecules. Each wash and elution fraction was collected by centrifugation.

Collected fractions were analyzed in a spectrophotometer by measuring the absorbance at 280 nm.

TABLE 1

Specification of the sample and solutions in column study I

| Step | Sample/Solution | Abbreviation |
|---|---|---|
| 1 | Pure sample of PEP08517 in 50 mM Tris-HCl, 5 mM EDTA, pH 8.5 | PEP08517 |
| 2 | Unbound PEP08517 | FT |
| 3 | 2.68 mM KCl, 1.47 mM $KH_2PO_4$, 137 mM NaCl, 8.1 mM $Na_2HPO_4$, pH 7.4 | PBS |
| 4 | 5 mM Tris-HCl, pH 8 | Tris |
| 5 | 0.5M HAc/NaAc, pH 4 | pH 4 (a) |
| 6 | 0.5M HAc/NaAc, pH 4 | pH 4 (b) |
| 7 | 0.5M HAc, pH 2.5 | pH 2.5 (a) |
| 8 | 0.5M HAc, pH 2.5 | pH 2.5 (b) |

Column Study II: Assessment of ABD Binding Z Variant-Coupled Resins Using a Bacterial Extract:

A second column study was performed to further test binding, wash and elution properties of four ABD binding Z variant-coupled resins from column study I. The ligands of these resins were $His_6$-(Z06608)$_2$-Cys, $His_6$-(Z06638)$_2$-Cys, $His_6$-(Z06677)$_2$-Cys and $His_6$-(Z06650)$_2$-Cys. An additional column packed with HSA Sepharose (human serum albumin coupled, according to the instructions by the manufacturer, via free amines to CNBr-activated Sepharose 4 Fast Flow, GE Healthcare, cat. no. 17-0981) was included as a reference. A clarified bacterial extract, prepared from an *E. coli* pellet by sonication and centrifugation, was used as sample in this experiment. 0.17 ml of the bacterial extract, containing approximately 0.5 mg of PEP08515 (comprising the albumin binding domain PP013 (SEQ ID NO:160) fused at its N-terminus to a PDGFR-β (Platelet Derived Growth Factor Receptor beta) binding variant of protein Z) was transferred to spin columns packed with each respective ABD binding Z variant-coupled resin or HSA Sepharose. Flow-through was collected by centrifugation and reapplied twice to the columns. Different solutions, specified in Table 2, were added to remove bacterial host proteins and to subsequently elute bound PEP08515 molecules. Wash and elution fractions were collected by centrifugation and analyzed in a spectrophotometer by measuring the absorbance at 280 nm, and by SDS-PAGE.

TABLE 2

Specification of the sample and solutions in column study II

| Step | Sample/Solution | Abbreviation | Volume (ml) |
|---|---|---|---|
| 1 | Sample: bacterial extract containing PEP08515 | PEP08515 | 0.17 |
| 2 | Flow-through I collected after sample application | FT I | 0.17 |
| 3 | Flow-through II collected after re-application of flow-through I | FT II | 0.17 |
| 4 | 2.68 mM KCl, 1.47 mM $KH_2PO_4$, 137 mM NaCl, 8.1 mM $Na_2HPO_4$, pH 7.4 | PBS | 4 × 0.2 |
| 5 | 5 mM $NH_4Ac$, pH 5.5 | $NH_4Ac$ | 2 × 0.2 |
| 6 | 0.1M sodium citrate, pH 3.0 | pH 3.0 (a) | 0.1 |
| 7 | 0.1M sodium citrate, pH 3.0 | pH 3.0 (b) | 0.1 |
| 8 | 0.5M HAc, pH 2.5 | pH 2.5 (a) | 0.1 |
| 9 | 0.5M HAc, pH 2.5 | pH 2.5 (b) | 0.1 |

Results

Coupling Efficiency of ABD Binding Polypeptides:

The degree of coupling of each ABD binding polypeptide to the SulfoLink Coupling Resin is shown in Table 3.

TABLE 3

The degree of coupling of ABD binding Z variants to SulfoLink Resin

| ABD binding polypeptide | Amount polypeptide coupled per ml resin (mg) | Amount polypeptide coupled per ml resin (μmol) |
|---|---|---|
| $His_6$-(Z06608)$_2$-Cys | 2.8 | 0.19 |
| $His_6$-(Z06620)$_2$-Cys | 2.7 | 0.19 |
| $His_6$-(Z06638)$_2$-Cys | 2.9 | 0.20 |
| $His_6$-(Z06650)$_2$-Cys | 3.4 | 0.23 |
| $His_6$-(Z06677)$_2$-Cys | 2.2 | 0.15 |
| $His_6$-(Z06678)$_2$-Cys | 2.1 | 0.14 |
| $His_6$-(Z06695)$_2$-Cys | 3.9 | 0.27 |

Figure 4:
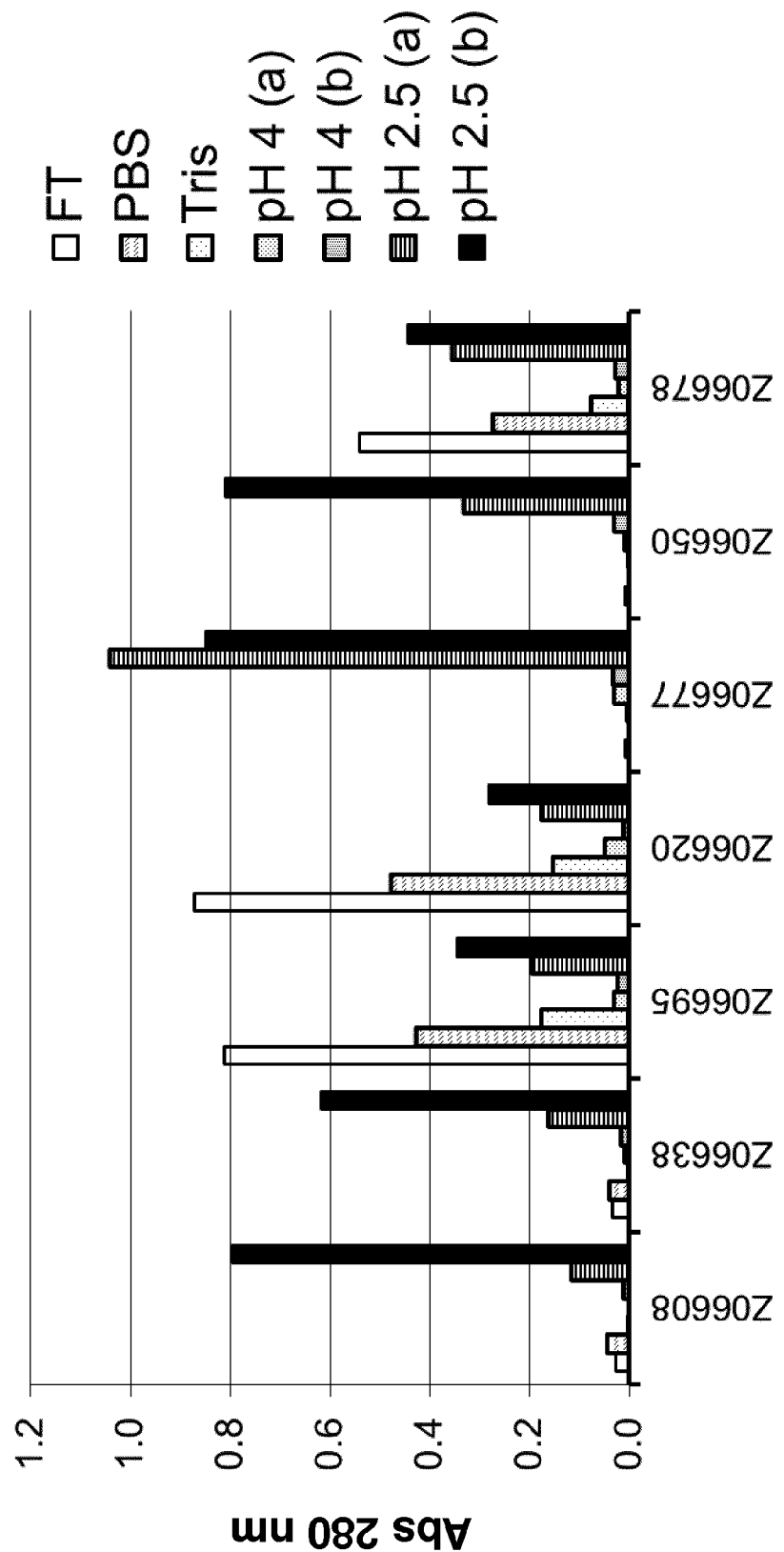
FIG. 4 shows the result from column study I described in Example 3. The bars in the diagram represent the relative amounts of the sample released from each of the ABD binding Z variant-coupled resins after the different wash and elution steps specified in Table 1.

Column Study I: Assessment of ABD Binding Z Variant-Coupled Resins Using a Pure Sample:

The amount of the sample PEP08517 released from each of the seven ABD binding Z variant-coupled resins after the different wash and elution steps specified in Table 1, and as determined by measuring the absorbance at 280 nm, is shown in FIG. 4.

Under the conditions studied, the resins coupled with the ABD binding Z variants (His$_6$-(Z06608)$_2$-Cys, His$_6$-(Z06638)$_2$-Cys, His$_6$-(Z06650)$_2$-Cys) and His$_6$-(Z06677)$_2$-Cys, respectively, showed the most favorable elution profile with minor sample leakage during sample application and wash and with the majority of sample being released at elution with pH 2.5 buffer.

None of the ABD binding Z variant-coupled resins eluted much of the sample at pH 4. Interestingly, some resins, for example His$_6$-(Z06608)$_2$-Cys, eluted most of the sample at the second addition of pH 2.5 buffer ("pH 2.5 (b)"), while for example His$_6$-(Z06677)$_2$-Cys eluted the majority of the sample at the first pH 2.5 buffer addition ("pH 2.5 (a)"), indicating that a higher elution pH could be used with the affinity ligand His$_6$-(Z06677)$_2$-Cys as compared with the other candidates.

Figure 5A:
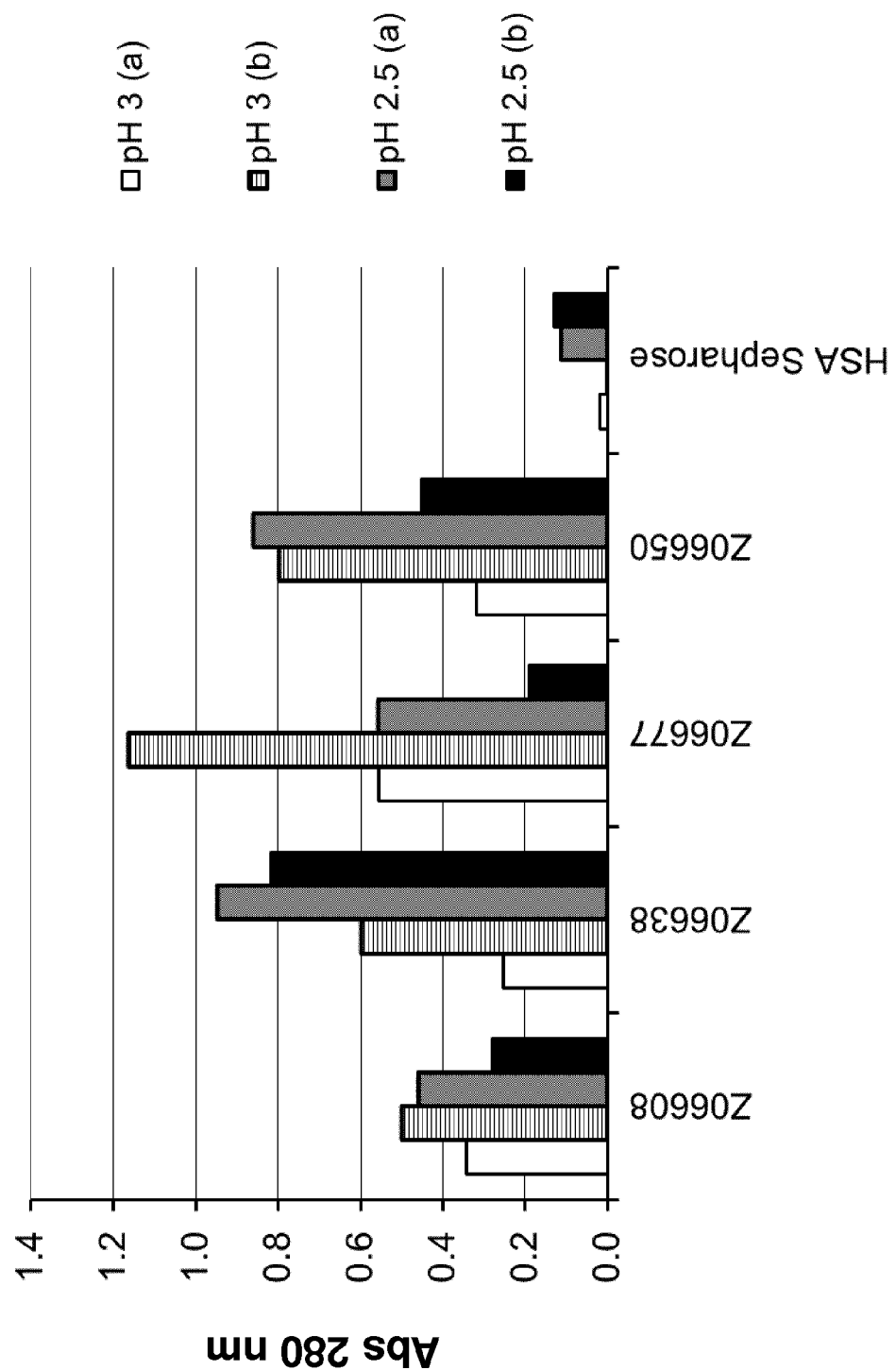
FIGS. 5A, 5B and 5C show the result from column study II described in Example 3.

Column Study II: Assessment of ABD Binding Z Variant-Coupled Resins Using a Bacterial Extract:

The four best performing ABD binding Z variant-coupled resins from column study I, including the affinity ligands His$_6$-(Z06608)$_2$-Cys, His$_6$-(Z06638)$_2$-Cys, His$_6$-(Z06650)$_2$-Cys and His$_6$-(Z06677)$_2$-Cys, were selected for further binding, wash and elution studies in which a bacterial extract containing PEP08515 was used as a sample. The amount of PEP08515 released from each of the four ABD binding Z variant-coupled resins, or from an HSA-Sepharose resin included as a reference, after the different elution steps specified in Table 2, and as determined by measuring the absorbance at 280 nm, is shown in FIG. 5A.

Figure 5B:
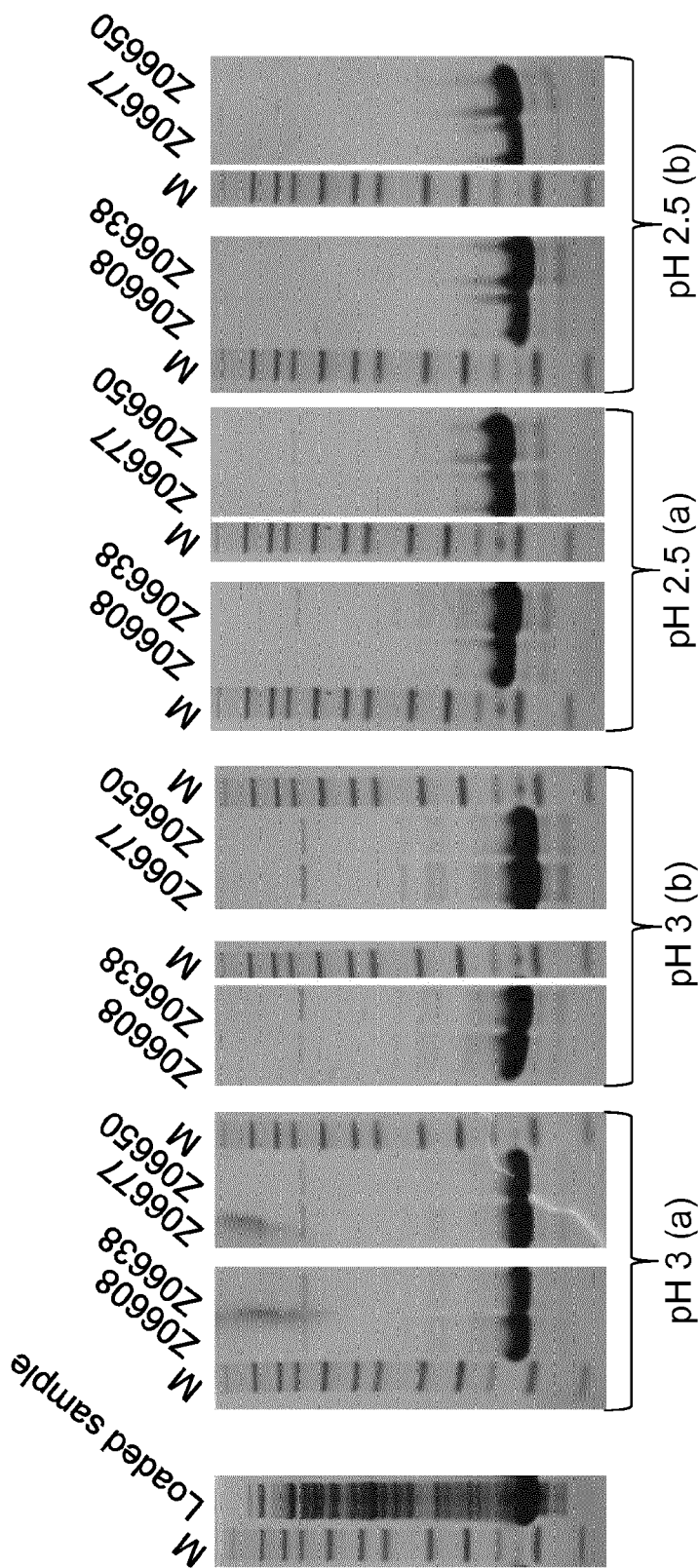

The SDS-PAGE analysis of the same eluted fractions is shown in FIG. 5B. The results from the two analyses agreed well, i.e. for a certain affinity ligand, an eluted fraction with a high absorbance reading also gave a thick band on the SDS-PAGE gel, and vice versa for fractions with a lower absorbance reading. As in column study I, the resin coupled with His$_6$-(Z06677)$_2$-Cys released a majority of its bound protein at the higher pH range of elution ("pH 3 (a)" and "pH 3 (b)").

The purity of all eluted samples was generally very high (exceeding 95%, as estimated from the SDS-PAGE analysis), but slight differences could be observed for the different ABD binding Z variants.

Figure 5C:
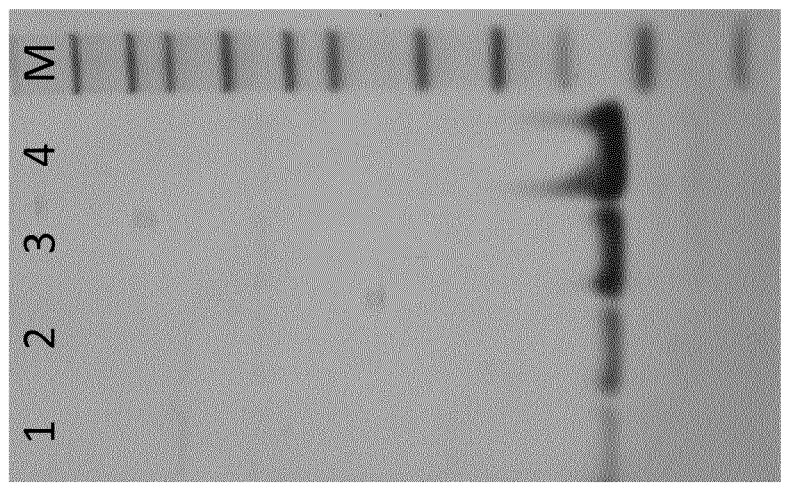

In comparison to the HSA Sepharose resin (SDS-PAGE analysis shown in FIG. 5C), the ABD binding Z variant-coupled resins appear to have a higher binding capacity as well as more favorable elution properties as judged both from the absorbance readings and the SDS-PAGE analysis. The difference in capacity cannot be due to differences in ligand density; in fact, the number of coupled HSA molecules on HSA Sepharose was approximately 1.5-2.2 times higher compared to the ABD binding Z variant-coupled resins.

Example 4

Further Characterization and Column Studies of an ABD Binding Z Variant

Based on the results presented in Example 3, His$_6$-(Z06677)$_2$-Cys was selected for further characterization and studies on columns connected to a chromatography system.

Materials and Methods

Determination of the Melting Point by Circular Dichroism Analysis:

Circular dichroism (CD) analysis was carried out to determine the melting point (Tm) of His$_6$-(Z06677)$_2$-Cys. The purified sample was diluted to 0.5 mg/ml in PBS. A variable temperature measurement (VTM) was performed, in which the absorbance at 220 nm was monitored during heating of the sample from 20° C. to 90° C., with a temperature slope of 5° C./min. Tm was determined from the midpoint of the transition in the CD signal vs. temperature plot. The CD measurement was performed on a Jasco J-810 spectropolarimeter (Jasco Scandinavia AB) using a cell with an optical path length of 1 mm.

Chromatography Study of Elution pH:

His$_6$-(Z06677)$_2$-Cys was immobilized on activated EAH-Sepharose 4B (GE Healthcare, cat. no. 17-0569-01). Activation and immobilization was carried out according to the manufacturer's instructions, and the degree of coupling was determined as described in Example 3. Activated EAH Sepharose contains an iodoacetyl group that enables site-directed coupling via the C-terminal cysteine of the affinity ligand. 0.43 ml of the resin was packed in a Tricorn 5/50 column (GE Healthcare). As a reference, 0.47 ml HSA Sepharose (see Example 3) was packed in the same kind of column.

The elution experiment was performed using an ÄKTA-explorer 10 chromatography system (GE Healthcare). The two columns were attached to the system and equilibrated with PBS. 2 ml of a sample containing 1 mg PEP08519 (comprising the albumin binding domain PP013 (SEQ ID NO:160) fused at its N-terminus to a Taq polymerase binding variant of protein Z) was loaded on each column followed by wash with PBS and 0.1 M sodium citrate, 0.9% NaCl, pH 5.5. Bound protein was eluted by a linear pH gradient ranging from pH 5.5 to pH 2.3 (using 0.1 M sodium citrate, 0.9% NaCl, pH 5.5, and 0.1 M sodium citrate, 0.9% NaCl, pH 2.3) over 16 column volumes (CV). The pH was monitored by the built-in pH meter of the ÄKTAexplorer system.

Chromatography Study of the Binding Capacity and Alkali Resistance of an ABD Binding Polypeptide:

In this experiment, the dynamic binding capacity and resistance to alkali was tested for the His$_6$-(Z06677)$_2$-Cys resin and an HSA Sepharose resin packed in the Tricorn 5/50 columns used in the chromatography study described in the previous section.

The experiment was performed using an ÄKTAexplorer 10 chromatography system. The two columns were attached to the system and equilibrated with PBS. For the capacity study, a sample containing 0.25 mg/ml of PEP08519 in PBS was loaded on each column at a flow-rate of 0.2 ml/min (corresponding to a residence time of 2.4 min) until the absorbance at 280 nm of the solution emerging from the columns reached 10% of the absorbance of the original sample (i.e. 10% breakthrough). The dead volume (i.e. tubing and column volume, measured by running a sample through a column comprising no affinity ligand) was subtracted from the sample volume. Bound protein was eluted with 0.1 M sodium citrate, 0.9 NaCl, pH 2.3. The columns were then re-equilibrated with PBS.

After the capacity runs, the columns were subjected to alkali treatment by applying 5 CV of 0.2 M NaOH at a flow-rate of 1 ml/min, followed by an incubation period without flow. The total incubation time in alkali was 25 min. Neutralization of the columns was performed by washing with 5 CV of PBS at 1 ml/min, followed by a new capacity measurement as described above.

Two more alkali treatments followed by capacity measurements were carried out as above, but with the NaOH concentration increased to 0.5 M and, in the last alkali treatment, the incubation time was extended to 2 h.

Figure 6:
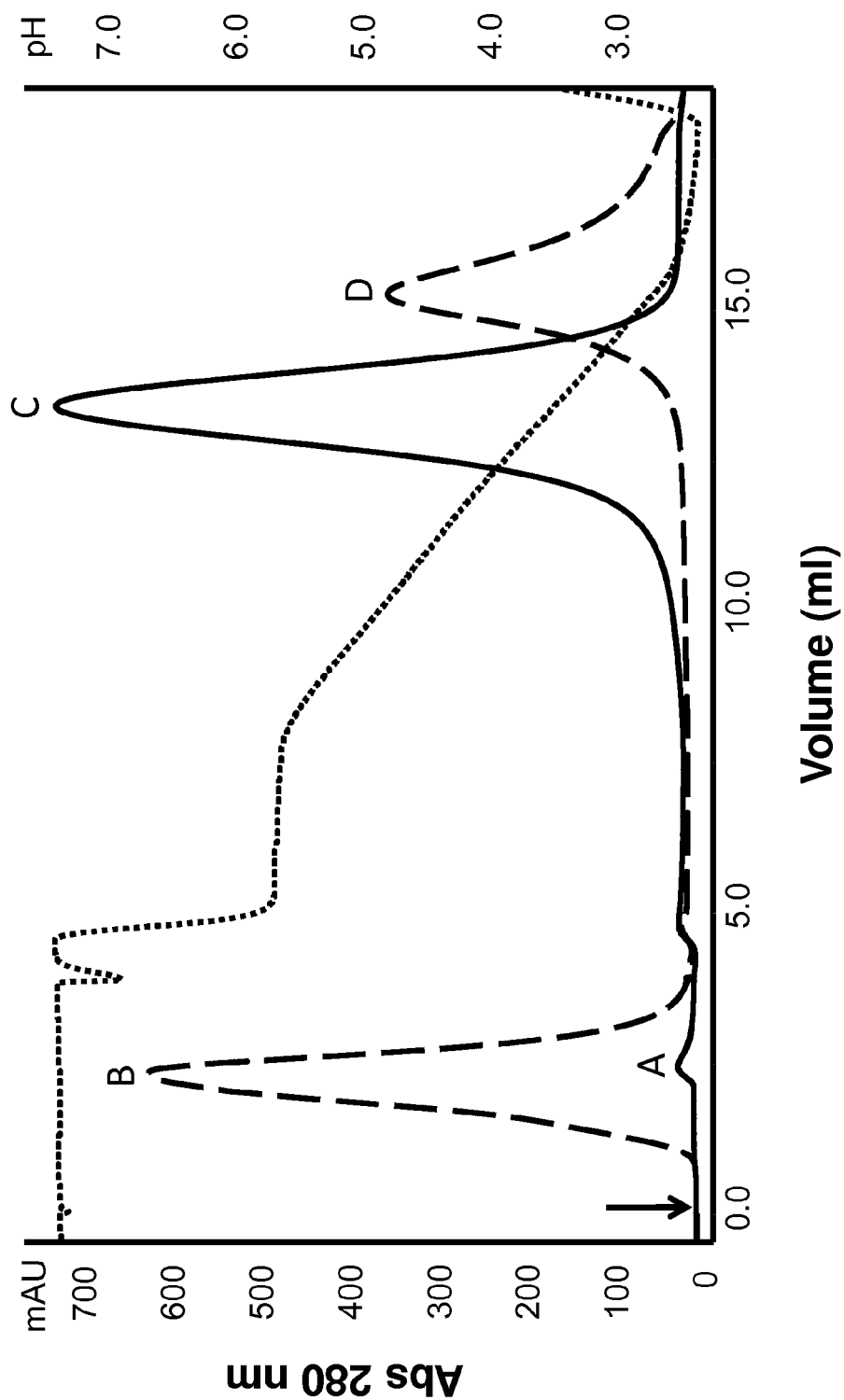
FIG. 6 shows a chromatogram from affinity purification, carried out as described in Example 4, of an ABD-fusion protein on an EAH-Sepharose resin coupled with $His_6$-$(Z06677)_2$-Cys (solid line). Purification of an identical sample on a Sepharose resin coupled with HSA (broken line), is included for reference. The sample injection point is indicated with an arrow. A and B indicate the flow-through fractions, and C and D the eluted fractions, from the $His_6$-$(Z06677)_2$-Cys-coupled resin and the HSA-coupled resin, respectively. Elution was performed with a linear pH gradient ranging from pH 5.5 to pH 2.3. The pH (dotted line) was monitored by the built-in pH meter of the HPLC system.
Figure 7:
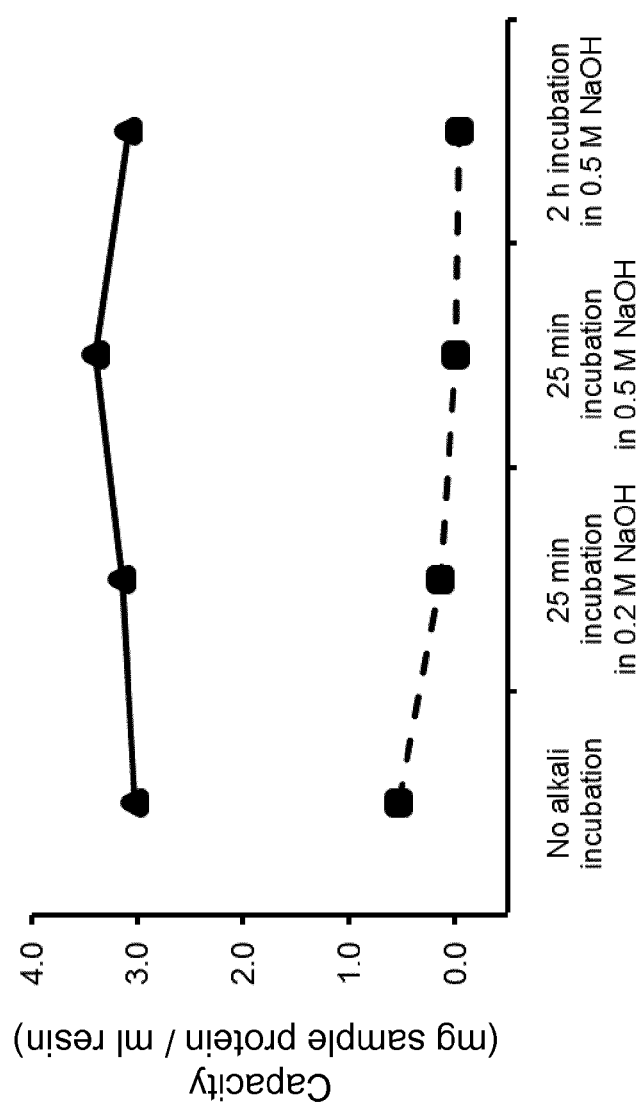
FIG. 7 shows the dynamic binding capacity of $His_6$-$(Z06677)_2$-Cys coupled to EAH-Sepharose resin (solid line), measured after repeated alkali incubations carried out as indicated and as further described in Example 4. The binding capacity of HSA coupled to Sepharose resin (broken line) is included for reference.

Results
  Circular Dichroism Analysis:
    The melting point of $His_6$-$(Z06677)_2$-Cys was determined to be 54° C.
  Chromatography Study of Elution pH of an ABD Binding Z Variant:
    The coupling degree of $His_6$-$(Z06677)_2$-Cys to the activated EAH Sepharose resin was determined to be 2.8 mg polypeptide per ml resin.
    As shown in FIG. 6, the elution of the ABD-fusion molecule PEP08519 from the column containing the $His_6$-$(Z06677)_2$-Cys resin appeared earlier in the gradient (i.e. at a higher pH) than from the column with the HSA Sepharose resin, which also showed lower binding capacity with a larger fraction emerging in the flow through.
    pH at peak maximum for the eluted peak from the $His_6$-$(Z06677)_2$-Cys column was 3.3, while the corresponding pH for the HSA Sepharose column was 2.6.
  Chromatography Study of the Binding Capacity and Alkali Resistance of an ABD Binding Z Variant:
    The dynamic binding capacity was determined by measuring the amount of sample loaded until 10% breakthrough. The dynamic binding capacity of the $His_6$-$(Z06677)_2$-Cys column was determined to be 3.0 mg PEP08519 per ml resin. The corresponding capacity for the HSA Sepharose column was determined to 0.5 mg per ml resin. As in Example 3, the difference in capacity cannot be explained by the difference in ligand density, since the number of immobilized HSA molecules were estimated to be twice the number of $His_6$-$(Z06677)_2$-Cys molecules on their respective resins.
    The dynamic binding capacity was re-measured after each alkali incubation. The results are shown in FIG. 7. The $His_6$-$(Z06677)_2$-Cys column maintained its original capacity after all incubations. This indicates a high resistance to relatively harsh alkali conditions, which is an important feature for cleaning in place (CIP) procedures enabling repeated use of the column. In contrast, the HSA Sepharose column, included as a reference, lost most of its capacity after 25 min in 0.2 M NaOH.

Example 5

Column Studies of an ABD Binding Z Variant Immobilized on Different Resins

In this example, the ABD binding Z variant $His_6$-$(Z06677)_2$-Cys was immobilized on four different types of resins, and the binding capacity and alkali resistance were assessed chromatographically.
Materials and Methods
  Coupling of $His_6$-$(Z06677)_2$-Cys to Different Resins:
    4 mg of the lyophilized $His_6$-$(Z06677)_2$-Cys (produced as described in Example 2) was dissolved in 1 ml 0.1 M $NaHCO_3$, 0.5 M NaCl, pH 8.3. One half of the sample was immobilized on 0.67 ml NHS-activated Sepharose 4 Fast Flow (GE Healthcare, cat. no. 17-0906) and one half of the sample was immobilized on 0.67 ml CNBr-activated Sepharose 4 Fast Flow (GE Healthcare, cat. no. 17-0981). Both coupling reactions were carried out according to the instructions by the manufacturer.
    2 mg of lyophilized $His_6$-$(Z06677)_2$-Cys was dissolved in 0.5 ml 50 mM Tris-HCl, 5 mM EDTA, 20 mM DTT, pH 8.5 and incubated for 2 h. DTT was removed by size exclusion chromatography and the reduced polypeptide was mixed with 0.67 ml SulfoLink Coupling Resin. The coupling reaction was performed according to the instructions by the manufacturer.
    The fourth resin assessed in this experiment was EAH Sepharose immobilized with $His_6$-$(Z06677)_2$-Cys as described in Example 4.
    The degree of coupling for each resin was determined as described in Example 3.
  Chromatography Study of the Binding Capacity and Alkali Resistance of Four ABD Binding Resins:
    The four $His_6$-$(Z06677)_2$-Cys-coupled resins were packed in Tricorn 5/50 columns. The dynamic binding capacity was tested, after which the resins were subjected to 0.5 M NaOH for 2 h, followed by a second dynamic binding capacity test. The capacity tests and alkali incubations were carried out as described in Example 4.
Results
  Coupling of the ABD Binding Z Variant $his_6$-$(Z06677)_2$-Cys to Different Resins:
    The degree of immobilization of $His_6$-$(Z06677)_2$-Cys to each of the four different resins assessed in this experiment are shown in Table 5.

TABLE 5

The degree of coupling of $His_6$-$(Z06677)_2$-Cys to different resins

| Type of resin | $His_6$-$(Z06677)_2$-Cys coupled per ml resin (mg) |
| --- | --- |
| NHS-activated Sepharose 4 Fast Flow | 2.6 |
| CNBr-activated Sepharose 4 Fast Flow | 2.6 |
| SulfoLink Coupling Resin | 1.9 |
| Activated EAH Sepharose | 2.8 |

Chromatography Study of the Binding Capacity and Alkali Resistance of Four ABD Binding Resins:
    The dynamic binding capacity determined after coupling of $His_6$-$(Z06677)_2$-Cys to each of the four resins is presented in Table 6.

TABLE 6

The dynamic binding capacity of $His_6$-$(Z06677)_2$-Cys coupled to different resins

| | Dynamic binding capacity | |
| --- | --- | --- |
| Type of resin | (mg sample/ ml resin) | (mol sample/ mol ligand) |
| NHS-activated Sepharose 4 Fast Flow | 0.9 | 0.4 |
| CNBr-activated Sepharose 4 Fast Flow | 2.0 | 0.9 |
| SulfoLink Coupling Resin | 2.3 | 1.4 |
| Activated EAH Sepharose | 3.4 | 1.4 |

The dynamic binding capacities of the two iodoacetyl-coupled resins, SulfoLink Coupling Resin and Activated EAH Sepharose, were determined to 2.3 and 3.4 mg sample per ml resin, respectively. However, when comparing the molar amount of sample that can bind per mole of affinity ligand, these resins show the same dynamic binding capacity (1.4 mol of sample/mol of $His_6$-$(Z06677)_2$-Cys ligand). In other words, for $His_6$-$(Z06677)_2$-Cys coupled to the SulfoLink resin, the two Z molecules within the dimer bind a sample molecule each to a higher extent compared to $His_6$-$(Z06677)_2$-Cys coupled to EAH Sepharose resin.

The dynamic binding capacities of the two amine-coupled resins, i.e. NHS-activated Sepharose and CNBr-activated Sepharose, were lower than for the two iodoacetyl-coupled resins. This indicates that the site-directed immobilization through a single cysteine, as used for coupling to the iodoacetyl resins, makes the binding sites of the ABD binding Z variant more accessible to the sample molecules in the mobile phase.

The dynamic binding capacity of the NHS resin was less than half compared with the CNBr resin, despite the fact that the NHS resin holds a spacer arm that would theoretically improve the capacity, by making the affinity ligands more accessible.

The dynamic binding capacities of the four different resins after alkali treatment with 0.5 M NaOH for 2 h are presented in Table 7. The dynamic binding capacities of the iodoacetyl-coupled resins were unaffected by the alkali incubation, while the capacities of the amine-coupled resins dropped by approximately 10%.

TABLE 7

Comparison of the dynamic binding capacities before and after alkali treatment.

| Type of resin | Original dynamic binding capacity (mol sample/mol affinity ligand) | Dynamic binding capacity after alkali incubation (mol sample/mol affinity ligand) |
|---|---|---|
| NHS-activated Sepharose 4 Fast Flow | 0.41 | 0.38 |
| CNBr-activated Sepharose 4 Fast Flow | 0.92 | 0.81 |
| SulfoLink Coupling Resin | 1.44 | 1.44 |
| Activated EAH Sepharose | 1.44 | 1.44 |

Example 6

Production of Anti-ABD Agarose

This Example describes a larger-scale production of the ABD binding Z variant Z006677 in a dimeric format and with an C-terminal Cys, i.e. (Z06677)$_2$-Cys, and its subsequent immobilization on a SulfoLink Coupling Resin.

Materials and Methods

Cultivation and Purification:

The ABD binding Z variant Z06677 was subcloned as a dimer into an expression vector in which expression is regulated by a T7 promoter. The ABD binding polypeptide was expressed with the additional N-terminal amino acid sequence GSSLQ and the additional C-terminal amino acid sequence VDC. Thus, the expressed polypeptide has the sequence GSSLQ-[Z06677][Z06677]-VDC (SEQ ID NO: 187). E. coli BL21 (DE3) cells (Novagen) were transformed with the plasmid and cultivated at 37° C. in 20 l of TSB+YE medium (Tryptic Soy Broth with Yeast Extract) supplemented with 50 μg/ml kanamycin. At $OD_{600}$=1, IPTG, at a final concentration of 0.17 mM, was added to induce protein expression and the cultivation was incubated at 37° C. for another 5 h. The cells were harvested by centrifugation.

As seen in Example 4 and Example 5, His$_6$-(Z06677)$_2$-Cys was proven to be resistant to alkali. This property was taken advantage of in the purification of (Z06677)$_2$-Cys, as high concentrations of NaOH contribute to both cell disruption and purification, and a large part of E. coli host proteins denature at high pH, whereas (Z06677)$_2$-Cys remains in solution.

165 g of cell pellet was re-suspended in 1.2 l of 0.5 M NaOH by use of Ultra-Turrax T-50 basic (IKA WERKE). The suspension was incubated for 1 h at RT under stirring and then frozen at −20° C. The frozen sample was thawed and titrated to pH 8.2 by addition of 300 ml of 2 M HCl and Tris base to a final concentration of 20 mM. Cell debris, denatured protein and DNA were removed by centrifugation. To the clarified sample, 800 ml of [20 mM Tris-HCl, pH 8.0, 4.6 g DTT] and Benzonase® (Merck, cat. no. 1.01654.0001) to a final concentration of 10 U/ml were added and incubation proceeded for 1 h at RT. Thereafter, 300 g of ammonium sulphate was added to a concentration of 1 M, and the sample was incubated at RT under stirring for 40 min. Protein precipitated after the addition of ammonium sulphate was removed by centrifugation, followed by filtration through a Nalgene bottle top filter (0.45 μm).

Acetonitrile (ACN) was added to the sample to a concentration of 2% (v/v). The sample was loaded onto a FineLine 35 column (GE Healthcare) packed with 125 ml SOURCE 30 RPC (GE Healthcare) by use of an ÄKTAexplorer 100 chromatography system (GE Healthcare). The column was washed with 2% ACN in Milli-Q water containing 0.1% TFA (tri-fluoro acetic acid) followed by wash with an identical buffer, containing 4% of ACN. Bound protein was eluted by increasing the ACN concentration from 4% to 25° A) ACN over 15 CV. Eluted fractions were collected and analyzed by SDS-PAGE and LC-MS. Relevant fractions were pooled and transferred to coupling buffer (50 mM Tris-HCl, 5 mM EDTA, pH 8.5) by size exclusion chromatography using an XK-50 column (GE Healthcare) packed with 500 ml Sephadex G-25 (GE Healthcare). The buffer exchanged sample was analyzed spectrophotometrically by measuring the absorbance at 280 nm, and by SDS-PAGE, loading several different quantities of (Z06677)$_2$-Cys, and subsequent staining with Coomassie Blue.

Coupling of the ABD Binding Polypeptide (Z06677)$_2$-Cys to Resin:

The sample containing (Z06677)$_2$-Cys at a concentration of 3.4 mg/ml in coupling buffer was reduced by addition of DTT to a concentration of 20 mM, followed by incubation under stirring for 1 h at RT. DTT was removed by size exclusion chromatography using an XK-50 column packed with 500 ml Sephadex G-25, pre-equilibrated with coupling buffer. The reduced (Z06677)$_2$-Cys was mixed with Sulfo-Link Coupling Resin (Thermo Scientific, cat. no. 20404) at a ratio of 6 mg (Z06677)$_2$-Cys per ml resin. The subsequent coupling reaction was carried out according to the instructions by the manufacturer, but the incubation of the protein-resin mixture was extended from 15 to 35 min. The coupling efficiency was estimated by SDS-PAGE analysis of the uncoupled protein.

Results

Cultivation and Purification:

The purified dimeric ABD binding Z variant (Z06677)$_2$-Cys was analyzed in a spectrophotometer by measuring the absorbance at 280 nm and by SDS-PAGE. (Z06677)$_2$-Cys lacks tryptophans, resulting in low absorbance readings at 280 nm. The concentration of the Z variant molecule was therefore estimated from the SDS-PAGE analysis, which included several different quantities of (Z06677)$_2$-Cys. Visual inspection of the SDS-PAGE gel estimated the concentration of (Z06677)$_2$-Cys to 3.4 mg/ml at a purity of approximately 95%.

Coupling of the ABD Binding Polypeptide (Z06677)$_2$-Cys to Resin:

The ligand density was estimated to 5.8 mg (Z06677)$_2$-Cys/ml SulfoLink Coupling Resin by visually inspecting an SDS-PAGE gel run on the uncoupled protein fraction of the coupling reaction.

The produced (Z06677)$_2$-Cys-coupled resin is further referred to as "anti-ABD agarose", and in the following Examples it was used to demonstrate the wide applicability of the resin, in terms of binding to different albumin binding domain moieties in fusion with different proteins of varying size and functions. It is shown that successful purification is achieved regardless of where in the target protein the ABD moiety is situated. In other words, the ABD moiety may be placed at the N-terminus, at the C-terminus or even within a fusion protein such that it is flanked by other protein moieties on either side.

Example 7

Purification of PEP10986 Using Anti-ABD Agarose

In this example, PEP10986 (12.5 kDa), comprising an albumin binding domain (PP013, SEQ ID NO:160) fused at its N-terminus to a cytokine binding variant of protein Z, was purified using a column packed with anti-ABD agarose.
Materials and Methods Pelleted E. coli cells harboring soluble PEP10986 were suspended in TST-buffer (Tris, Saline, Tween: 25 mM Tris-HCl, 1 mM EDTA, 200 mM NaCl, 0.05% Tween 20, pH 8.0) supplemented with 20 U/ml Benzonase®. Cells were disrupted by sonication and the cell debris removed by centrifugation. Chromatography was performed using an ÄKTAexplorer 100 system. The clarified sample was applied on an XK-50 column packed with 100 ml anti-ABD agarose (prepared as described in Example 6) and pre-equilibrated with TST. The column was washed with 8 CV of TST followed by 8 CV of 5 mM NH$_4$Ac pH 5.5. Bound protein was eluted by applying 3 CV of 0.1 M HAc, pH 2.9. Flow-through fractions, wash fractions and eluted fractions were collected for further analyses by SDS-PAGE and HPLC-MS.

Figure 8A:
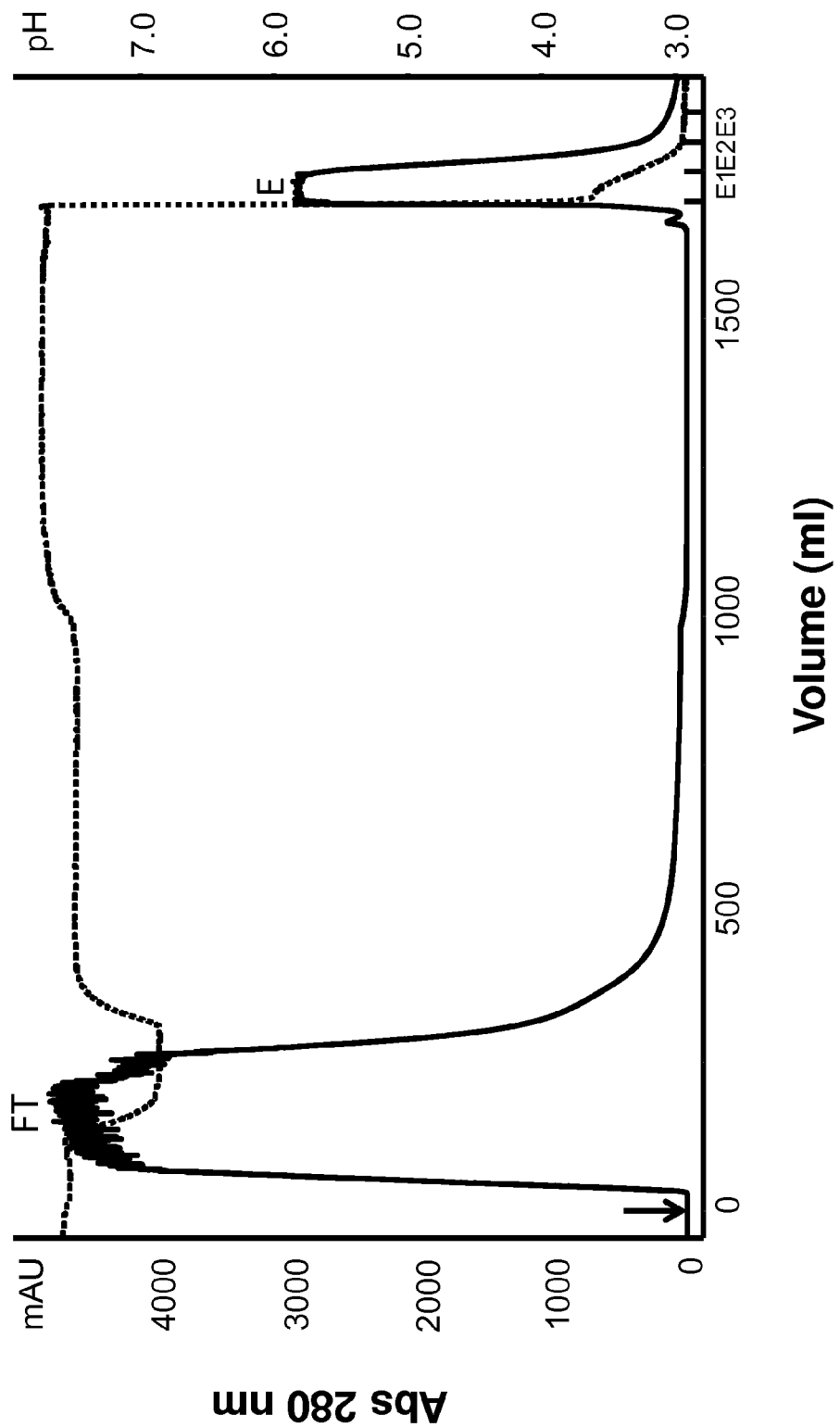
FIG. 8A shows a chromatogram from affinity purification of the ABD-fusion protein PEP10986 on anti-ABD agarose performed as described in Example 7. The sample injection point is indicated by an arrow. The absorbance signal at 280 nm is shown (solid line). FT and E refer to the flow-through fraction and eluted fraction, respectively. Elution was performed with 0.1 M HAc, pH 2.9 and the pH (dotted line) was monitored by the built-in pH meter of the HPLC system.
Figure 8B:
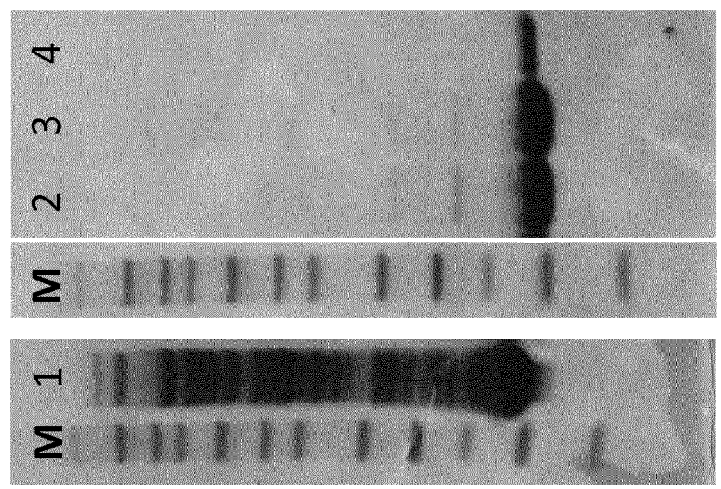
FIG. 8B shows the result of SDS-PAGE analysis of selected fractions from the purification described in Example 7. Lane 1: Clarified bacterial extract loaded on the column, Lane 2: Fraction E1, Lane 3: Fraction E2 and Lane 4: Fraction E3. "M" refers to Novex Sharp Pre-stained Protein standard (Invitrogen; Mw: 216, 160, 110, 80, 60, 50, 40, 30, 20, 15, 10, 3.5 kDa). 5 μl of each sample were loaded in respective lanes of the SDS-PAGE gel, except for lane 2 where 1.25 μl was loaded.

To investigate the robustness and alkali stability of the anti-ABD agarose resin, several purifications, each followed by a CIP (Cleaning In Place) cycle of 2-3 column volumes of 0.5 M NaOH, were subsequently performed using the same column as above.
Results The chromatogram from purification of PEP10986 on the anti-ABD agarose resin is presented in FIG. 8A and the SDS-PAGE analysis of selected fractions is shown in FIG. 8B. The eluted fractions E1, E2 and E3, corresponding to lane 2, 3 and 4 respectively in FIG. 8B, were pooled. The correct mass of PEP10986 was verified by HPLC-MS analysis and the purity was estimated to be higher than 95% as judged from SDS-PAGE analysis. According to spectrophotometrical analysis, the pool contained 908 mg of purified PEP10986, corresponding to a yield of approximately 90%.

Robustness and alkali stability of the anti-ABD agarose resin was confirmed by additional purifications of both PEP10986 and other ABD fusion molecules, each followed by a CIP (Cleaning In Place) cycle of 2-3 column volumes of 0.5 M NaOH, using the same column as in this Example. After 23 CIP cycles, no significant decrease in capacity had yet been observed.

Example 8

Purification of PEP03973 Using Anti-ABD Agarose

Figure 9A:
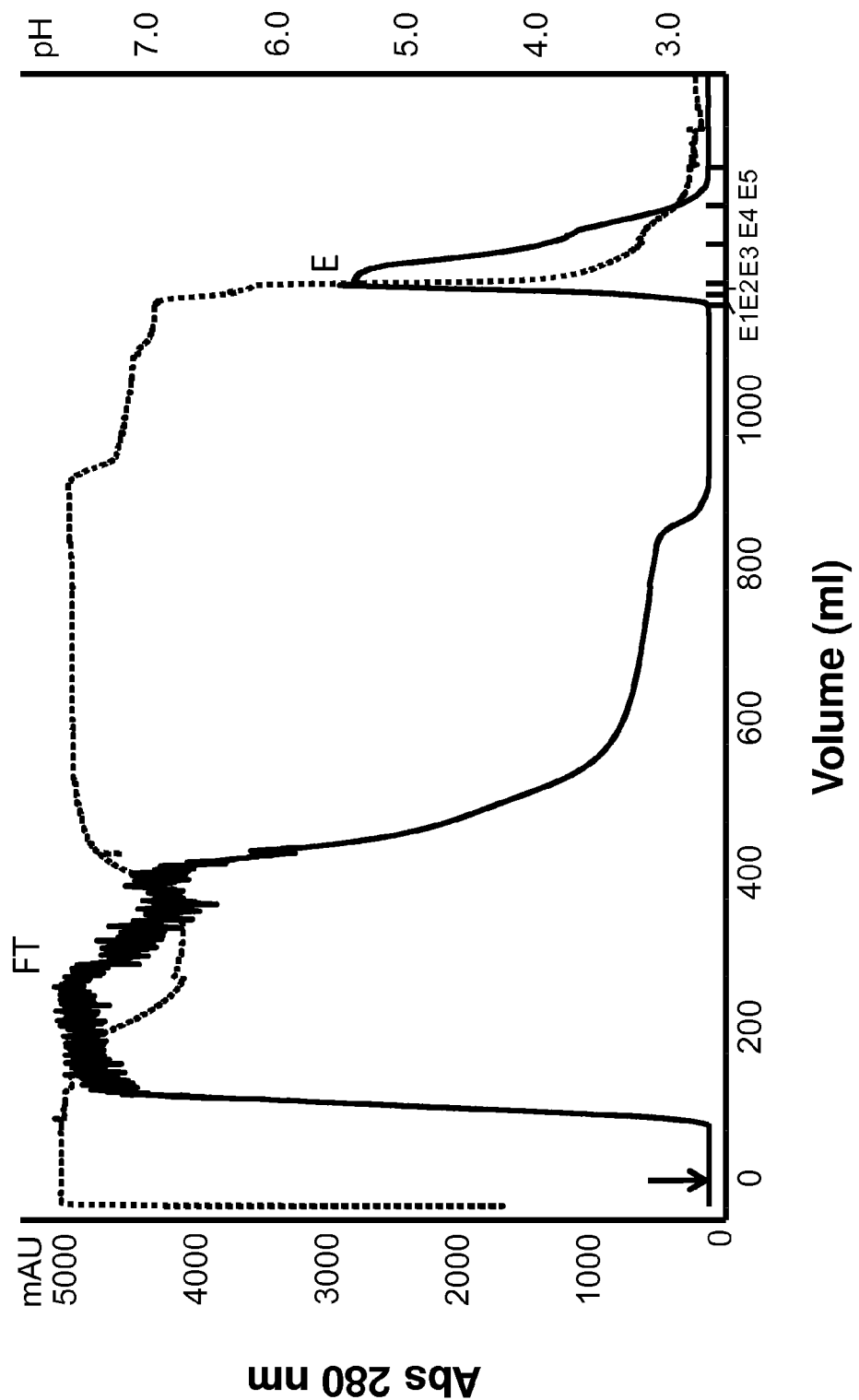
FIG. 9A shows a chromatogram from affinity purification of the ABD-fusion protein PEP03973 on anti-ABD agarose performed as described in Example 8. The sample injection point is indicated by an arrow. The absorbance signal at 280 nm is shown (solid line). FT and E refer to the flow-through fraction and eluted fraction, respectively. Elution was performed with 0.1 M HAc, pH 2.9 and the pH (dotted line) was monitored by the built-in pH meter of the HPLC system.
Figure 9B:
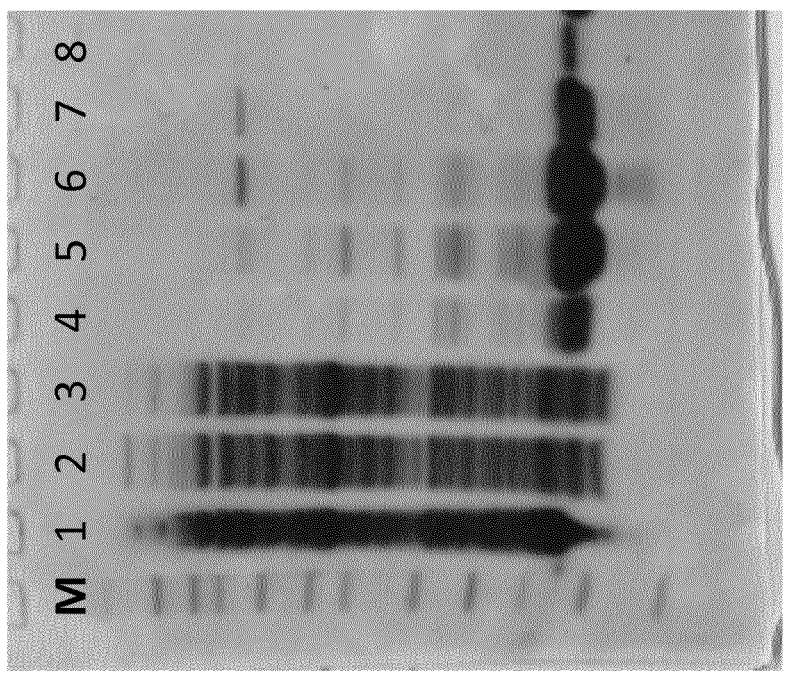
FIG. 9B shows the result of SDS-PAGE analysis of selected fractions from the purification described in Example 8. Lane 1: Clarified bacterial extract loaded on the column, Lane 2 and Lane 3: Flow-through, Lane 4: Fraction E1, Lane 5: Fraction E2, Lane 6: Fraction E3, Lane 7: Fraction E4, Lane 8: Fraction E5. "M" refers to Novex Sharp Pre-stained Protein standard (Invitrogen; Mw: 216, 160, 110, 80, 60, 50, 40, 30, 20, 15, 10, 3.5 kDa). 5 μl of each sample were loaded in respective lanes of the SDS-PAGE gel.

In this example, PEP03973 (12.4 kDa), comprising the wild-type albumin binding domain (ABD001, SEQ ID NO:157) fused at its N-terminus to a HER2 (Human Epidermal growth factor Receptor 2) binding variant of protein Z, was purified using a column packed with anti-ABD agarose.
Materials and Methods Pelleted E. coli cells harboring soluble PEP03973 were suspended in TST-buffer supplemented with 20 U/ml Benzonase®. Cells were disrupted by sonication and the cell debris removed by centrifugation. Chromatography was performed using an ÄKTAexplorer 100 system. The clarified sample was applied on an XK-50 column packed with 100 ml anti-ABD agarose (prepared as described in Example 6) and pre-equilibrated with TST. The column was washed with 5 CV of TST followed by 3 CV of 5 mM NH$_4$Ac pH 5.5. Bound protein was eluted by applying 3 CV of 0.1 M HAc, pH 2.9. Flow-through fractions, wash fractions and eluted fractions were collected for further analyses by SDS-PAGE and HPLC-MS.
Results The chromatogram from purification of PEP03973 on the anti-ABD agarose resin is presented in FIG. 9A and the SDS-PAGE analysis of selected fractions is shown in FIG. 9B. The eluted fractions E2, E3 and E4, corresponding to lane 5, 6 and 7 respectively in FIG. 9B, were pooled. The correct mass of PEP03973 was verified by HPLC-MS analysis and the purity was estimated to be higher than 95% as judged from SDS-PAGE analysis. According to spectrophotometrical analysis, the pool contained 1036 mg of purified PEP03973, corresponding to a yield of approximately 97%.

Example 9

Purification of PEP06548 Using Anti-ABD Agarose

In this example, PEP06548 (20.3 kDa), comprising an albumin binding domain (ABD035, SEQ ID NO:159, with the C-terminal extension VDC) fused at its N-terminus to two moieties (i.e. a dimer) of a variant of protein Z binding to TNF-α (tumor necrosis factor alpha), was purified using a column packed with anti-ABD agarose. PEP06548 also comprises an N-terminal hexahistidine tag and a C-terminal cysteine residue.
Materials and Methods Pelleted E. coli cells harboring soluble PEP06548 were suspended in TST-buffer supplemented with 27 U/ml Benzonase®. Cells were disrupted by sonication and the cell debris removed by centrifugation. The C-terminal cysteines of the PEP06548 sample molecules were reduced by addition of DTT to a final concentration of 20 mM, followed by incubation for 30 min at RT. Chromatography was performed using an ÄKTAexplorer 100 system. The clarified and reduced sample was applied on an XK-16 column packed with 9 ml anti-ABD agarose and pre-equilibrated with TST. This batch of anti-ABD agarose was prepared essentially as described in Example 6, except for a lower ligand density of approximately 2.3 mg (Z06677)$_2$-Cys per ml of resin. The column was washed with 5.5 CV of TST followed by 3.3 CV of 5 mM NH$_4$Ac pH 5.5. Bound protein was eluted by applying 2.9 CV of 0.1 M HAc, pH 2.9. Fractions were collected for further analyses by SDS-PAGE and HPLC-MS.

Results

Figure 10A:
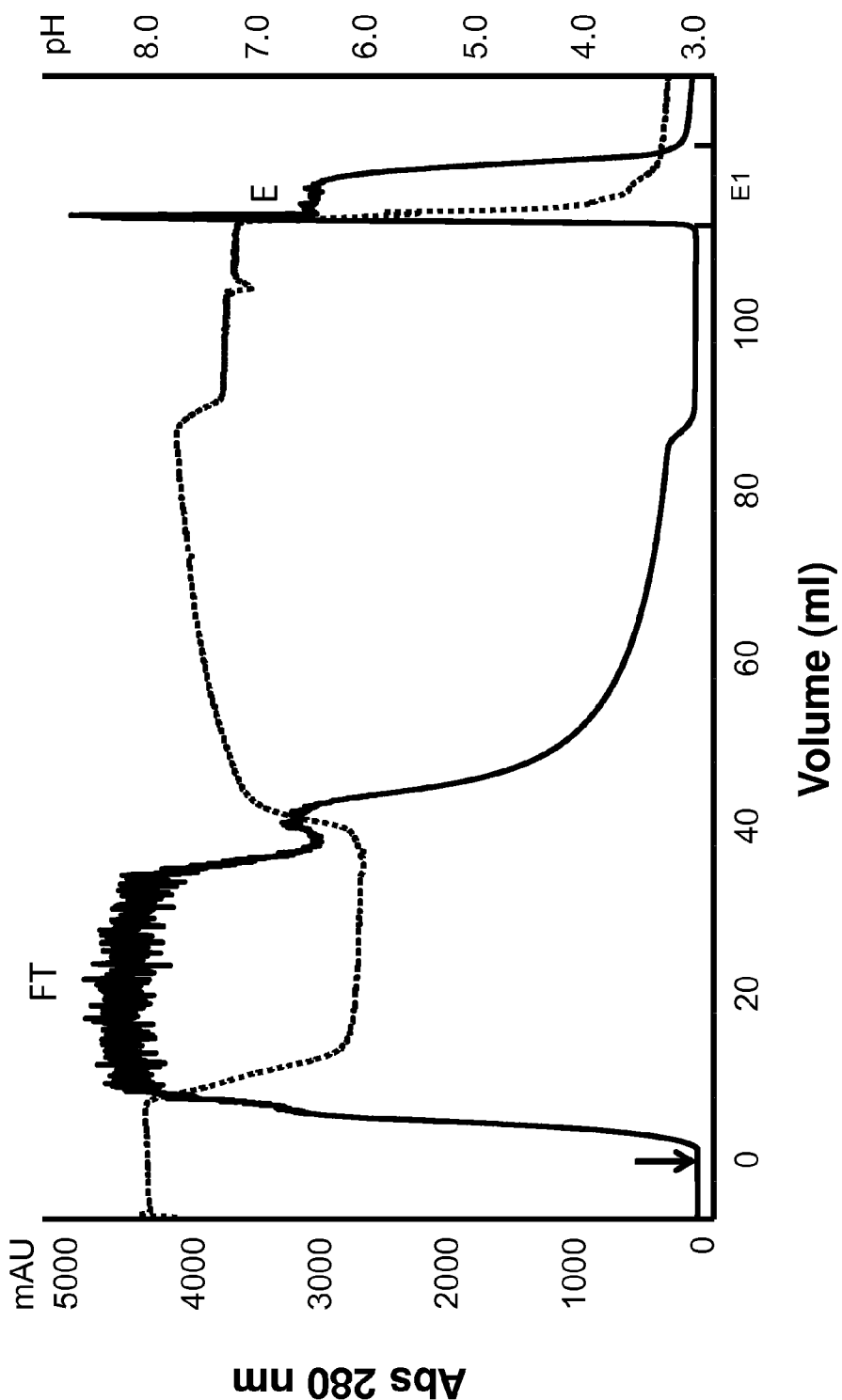
FIG. 10A shows a chromatogram from affinity purification of the ABD-fusion protein PEP06548 on anti-ABD agarose performed as described in Example 9. The sample injection point is indicated by an arrow. The absorbance signal at 280 nm is shown (solid line). FT and E refer to the flow-through fraction and eluted fraction, respectively. Elution was performed with 0.1 M HAc, pH 2.9 and the pH (dotted line) was monitored by the built-in pH meter of the HPLC system.
Figure 10B:
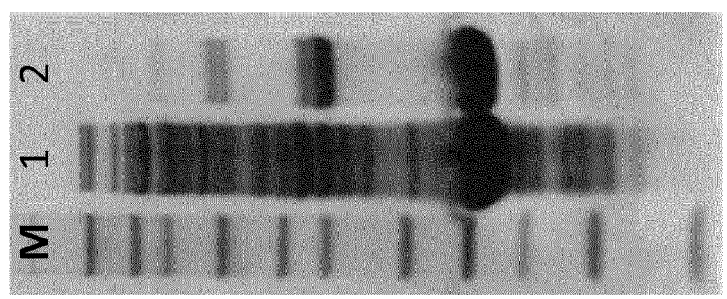
FIG. 10B shows the result of SDS-PAGE analysis of selected fractions from the purification described in Example 9. Lane 1: Clarified bacterial extract loaded on the column, Lane 2: Fraction E1. "M" refers to Novex Sharp Pre-stained Protein standard (Invitrogen; Mw: 216, 160, 110, 80, 60, 50, 40, 30, 20, 15, 10, 3.5 kDa). 5 μl were loaded in lane M and in lane 1 and 5.8 μl were loaded in lane 2 of the SDS-PAGE gel.

The chromatogram from purification of PEP06548 on the anti-ABD agarose resin is presented in FIG. 10A and the SDS-PAGE analysis of the eluted fraction E1 is shown in FIG. 10B. The purity was estimated to be higher than 95% as judged from the SDS-PAGE analysis. Bands at around 40 kDa were most probably derived from dimers formed by reaction between the C-terminal cysteines of the sample molecules. The correct masses of PEP06548, as well as a minor portion of the dimeric variant, were also identified in HPLC-MS analysis.

According to absorbance measurements, 3.7 mg purified PEP06548 per ml of resin was obtained, or approximately one PEP06548 molecule per (Z06677)$_2$-Cys ligand.

Example 10

Purification of PEP17081 Using Anti-ABD Agarose

In this example, PEP17081 (18.6 kDa), comprising an albumin binding domain (PEP07986, SEQ ID NO:161) fused to two moieties of a cytokine binding variant of protein Z in the format Z-PEP07986-Z, was purified using a column packed with anti-ABD agarose. Subsequent purification is also described.

Materials and Methods

Pelleted E. coli cells harboring soluble PEP17081 were suspended in TST-buffer. Cells were disrupted by heat treatment in a water bath (83° C., 10 min), followed by cooling on ice. Benzonase® was added to a final concentration of 15 U/ml to reduce viscosity caused by nucleic acids. Cell debris was removed by centrifugation and filtration (0.45 μm filter).

A first purification step was performed by anti-ABD agarose affinity chromatography using an ÄKTApurifier 100 system. The clarified sample was applied on an XK-26 column packed with 25 ml anti-ABD agarose and pre-equilibrated with 2×TST (i.e. TST buffer with all components at double concentration). The column was washed with 5 CV of 2×TST followed by 8 CV of 5 mM NH$_4$Ac, pH 5.5. Bound protein was eluted by applying 3 CV of 0.1 M HAc, pH 2.9. Fractions were collected for further analyses by SDS-PAGE and HPLC-MS.

A second purification step was performed by RPC, using an ÄKTAexplorer 100 system. The protein eluted from the anti-ABD agarose column was supplemented with acetonitrile to a final concentration of 10% and loaded on an HR-16 column (GE Healthcare) packed with 24 ml SOURCE 15 RPC (GE Healthcare) and pre-equilibrated with 10% acetonitrile, 0.1% trifluoroacetic acid (TFA) in Milli-Q water (Solvent A). The column was washed with 3.9 CV Solvent A. Bound material was eluted with a 15 CV linear gradient of increasing concentration of 80% acetonitrile, 0.1% TFA in Milli-Q water (Solvent B), ending at 50% Solvent B. Fractions were collected for further analyses by SDS-PAGE and HPLC-MS.

A third purification and buffer exchange step was performed by size exclusion chromatography (SEC) using an ÄKTAexplorer 100 system. Selected fractions eluted from the RPC column were pooled and buffer exchanged to 1×PBS on a XK-50 column packed with 500 ml Sephadex G-25 (GE Healthcare). Fractions were collected for further analyses by SDS-PAGE and HPLC-MS.

Results

Figure 11A:
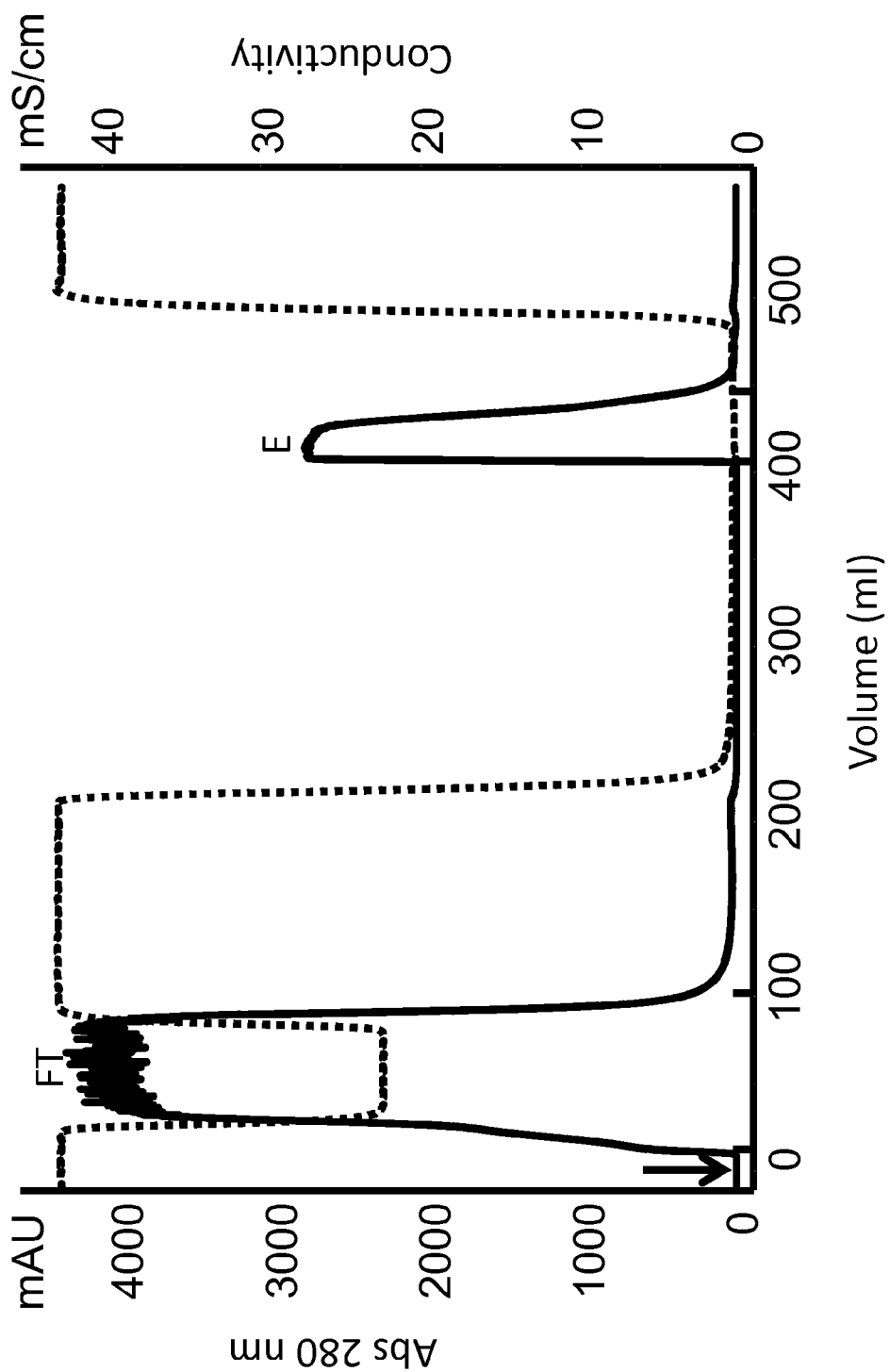
FIG. 11A shows a chromatogram of the purification of the ABD-fusion protein PEP17081 on anti-ABD agarose performed as described in Example 10. The absorbance signal at 280 nm (solid line) and the conductivity (dotted line) are shown. The sample injection point is indicated by an arrow. FT and E refer to the flow-through fraction and eluted fraction, respectively.
Figure 11B:
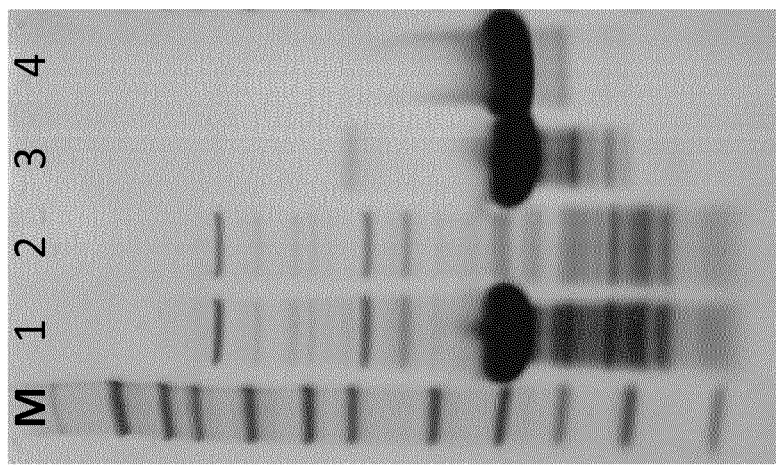
FIG. 11B shows the result of SDS-PAGE analysis of selected fractions from different stages of the purification described in Example 10. Lane M: 5 μl Novex Sharp Pre-stained Protein standard, Invitrogen (216, 160, 110, 80, 60, 50, 40, 30, 20, 15, 10, 3.5 kDa). Lane 1: 5 μl of the clarified, heat treated E. coli lysate that was loaded on the anti-ABD agarose column. Lane 2: 5 μl of the flow-through from the anti-ABD agarose column (FT in FIG. 11A). Lane 3: 3.6 μl of the eluted pool from the anti-ABD agarose column (E in FIG. 11A). Lane 4: 12 μl of PEP17081 further purified by RPC (reversed phase chromatography) and buffer exchanged.

The chromatogram from purification of PEP17081 on the anti-ABD agarose resin is presented in FIG. 11A, and the SDS-PAGE analysis is shown in FIG. 11B.

Heat treatment of the E. coli cells served both as a cell disruption step and a purification step. PEP17081 is resistant to heat while many other E. coli proteins are not and consequently precipitated upon heating. As a result, the material loaded on the anti-ABD agarose column was relatively pure (lane 1, FIG. 11B).

The vast majority of PEP17081 bound to the anti-ABD agarose resin, which is demonstrated by the apparent absence of PEP17081 in the flow through sample (lane 2, FIG. 11B). According to spectrophotometric analysis, the eluted pool contained 330 mg PEP17081, corresponding to a binding capacity of 13 mg PEP17081 per ml resin and a yield exceeding 95%. The purity of eluted PEP17081 was estimated to be higher than 95% as judged from the SDS-PAGE analysis (lane 3, FIG. 11B). A further increase in purity was obtained after RPC and buffer exchange by SEC (lane 4, FIG. 11B). The correct mass of PEP17081 was verified by HPLC-MS analysis.

Example 11

Purification of a Protein Hormone Using Anti-ABD Agarose

In this example, Protein 1 (22.6 kDa; pI 10), comprising an albumin binding domain (ABD035, SEQ ID NO: 159) fused at its C-terminus to a protein hormone, was purified on an ÄKTAexplorer system using a column packed with anti-ABD agarose.

Materials and Methods

Protein 1 was expressed in E. coli in the form of inclusion bodies. After solubilization and refolding of the inclusion bodies the material was run three times on size-exclusion chromatography (SEC) for buffer exchange and purification. 8 mg of the SEC purified Protein 1, in PBS diluted 1:10 in TST, was loaded at 0.5 ml/min on an XK 16/20 column (GE Healthcare) packed with 10-12 ml anti-ABD agarose and pre-equilibrated with TST. The column was washed with 4 CV of TST, followed by an additional 3 CV wash with 5 mM NH$_4$Ac, pH 5.5, at a flow rate of 1 ml/min. Bound protein was eluted with 3 CV of 0.1 M HAc, pH 2.9, and then neutralized to pH 7 with 1 M Tris-HCl, pH 9. Flow-through fractions, wash fractions and eluted fractions were collected for further analysis by SDS-PAGE. 4-12% Bis-Tris NuPAGE gels (Invitrogen) were run non-reduced and the protein stained with Simply Blue (Life Technologies). The column was re-equilibrated with TST after elution and cleaned in place (CIP) with 3 CV of 0.5 M NaOH followed by 3 CV of TST. Between purifications, the resin was stored in TST+20% ethanol.

Results

Figure 12A:
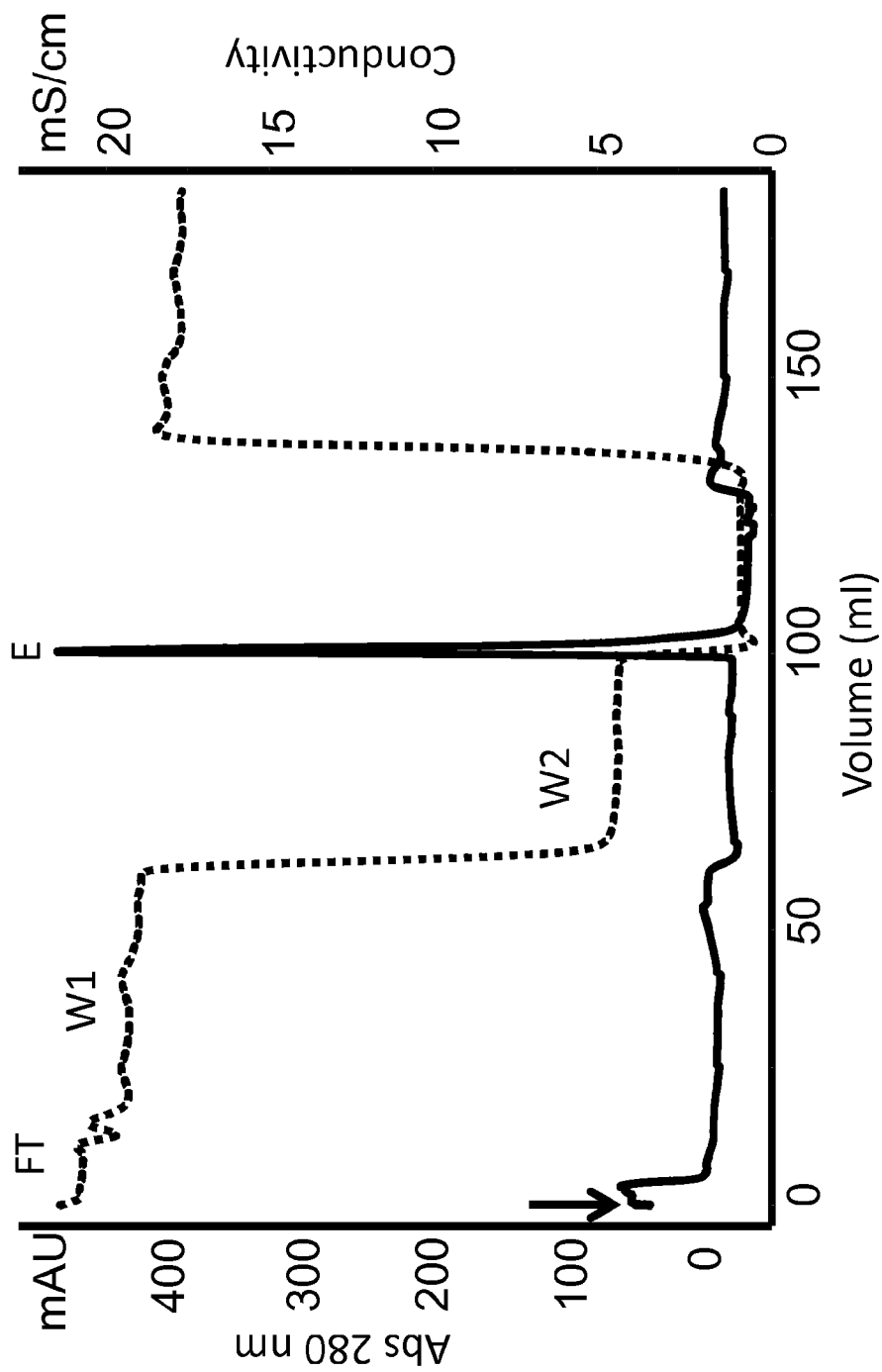
FIG. 12A shows a chromatogram from affinity purification of Protein 1, comprising ABD035 (SEQ ID NO:159) fused at its C-terminus to a protein hormone, on anti-ABD agarose performed as described in Example 11. The sample injection point is indicated by an arrow. The absorbance signal at 280 nm (solid line) and the conductivity (dotted line) are shown. FT, W and E refer to the flow-through fraction, wash fractions and eluted fraction, respectively. First wash step, W1, was performed with 4 CV of TST and second wash step, W2, with 3 CV of 5 mM NH$_4$Ac, pH 5.5.
Figure 12B:
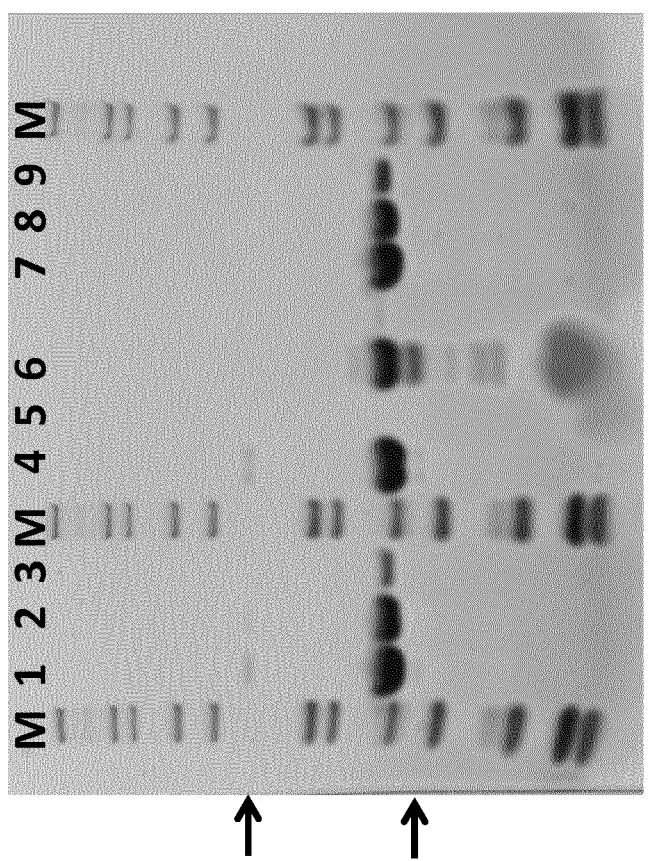
FIG. 12B shows the result of SDS-PAGE analysis of selected fractions from the purification described in Example 11. Lanes 1-3: SEC purified protein: 10 μg (1), 5 μg (2) and 1 μg (3). Lane 4: Protein sample loaded on the anti-ABD agarose column, i.e. SEC purified protein diluted 1:10 in TST. Lane 5: FT concentrated 20 times. Lane 6: W1 concentrated 60 times. Lanes 7, 8 and 9: Eluted protein: 10 μg (7), 5 μg (8) and 1 μg (9), respectively. Lanes marked with "M" were loaded with a protein molecular weight marker (Mw: 200, 116.3, 97.4, 66.3, 55.4, 36.5, 31, 21.5, 14.4, 6, 3.5, 2.5 kDa). Arrows indicate weak bands of contaminating proteins which were visible on the SDS-PAGE gel in samples purified by SEC only, but which were efficiently removed by purification on the anti-ABD agarose resin.

The chromatogram from purification of Protein 1 on the anti-ABD agarose resin is presented in FIG. 12A and the SDS-PAGE analysis of selected fractions is shown in FIG. 12B. The purity of the SEC purified Protein 1 loaded on the anti-ABD agarose column was high. However, weak bands of contaminating protein were visible on the SDS-PAGE gel, see arrows in FIG. 12B. These contaminants were effectively eliminated by purification on the anti-ABD agarose column. A sample from the wash step concentrated 60 times was analyzed on SDS-PAGE and revealed contaminants (as well as leakage of Protein 1; lane 6, FIG. 12B). No contaminants were seen in the eluted protein sample (lanes 7-9, FIG. 12B). The purity of the eluted sample was estimated to be higher than 98% as judged from SDS-PAGE analysis. The correct mass of the eluted Protein 1 was verified by HPLC-MS analysis.

Of the initial 8 mg of SEC purified Protein 1, 5.4 mg was collected in the eluted fractions from the anti-ABD agarose column, resulting in a yield of approximately 68%. Although no protein was detected in the flow through sample loaded in lane 5 (FIG. 12B), there was some leakage of Protein 1 upon washing with TST as well as removal of dimers and contaminating proteins.

Example 12

Purification of a Peptide Hormone Using Anti-ABD Agarose

In this example, Protein 2 (9.5 kDa, pI 6.6), comprising an albumin binding domain (ABD035, SEQ ID NO: 159) fused at its N-terminus to a peptide hormone, was expressed in *Pichia Pink* and purified in a single step on an ÄKTAexplorer system using a column packed with anti-ABD agarose.

Materials and Methods 100 ml of *Pichia Pink* supernatant containing secreted Protein 2 was lyophilized and resuspended in 2 ml DMSO (dimethyl sulfoxide) and subsequently diluted with 200 ml of TST. The sample was loaded at 1 ml/min on an XK 16/20 column packed with 10-12 ml anti-ABD agarose and pre-equilibrated with TST. The column was washed with 8 CV of TST, followed by an additional 3 CV wash with 5 mM $NH_4Ac$, pH 5.5. The usual wash of 4 CV TST was increased due to the high density of contaminating proteins from the media. Bound protein was eluted with 3 CV of 0.1 M HAc, pH 2.9 and then adjusted to pH 4 with 1 M Tris-HCl, pH 9. The column was re-equilibrated with TST after elution followed by CIP and storage in TST+20% ethanol. Flow-through fractions, wash fractions and eluted fractions were collected for further analysis by SDS-PAGE.

Results

Figure 13A:
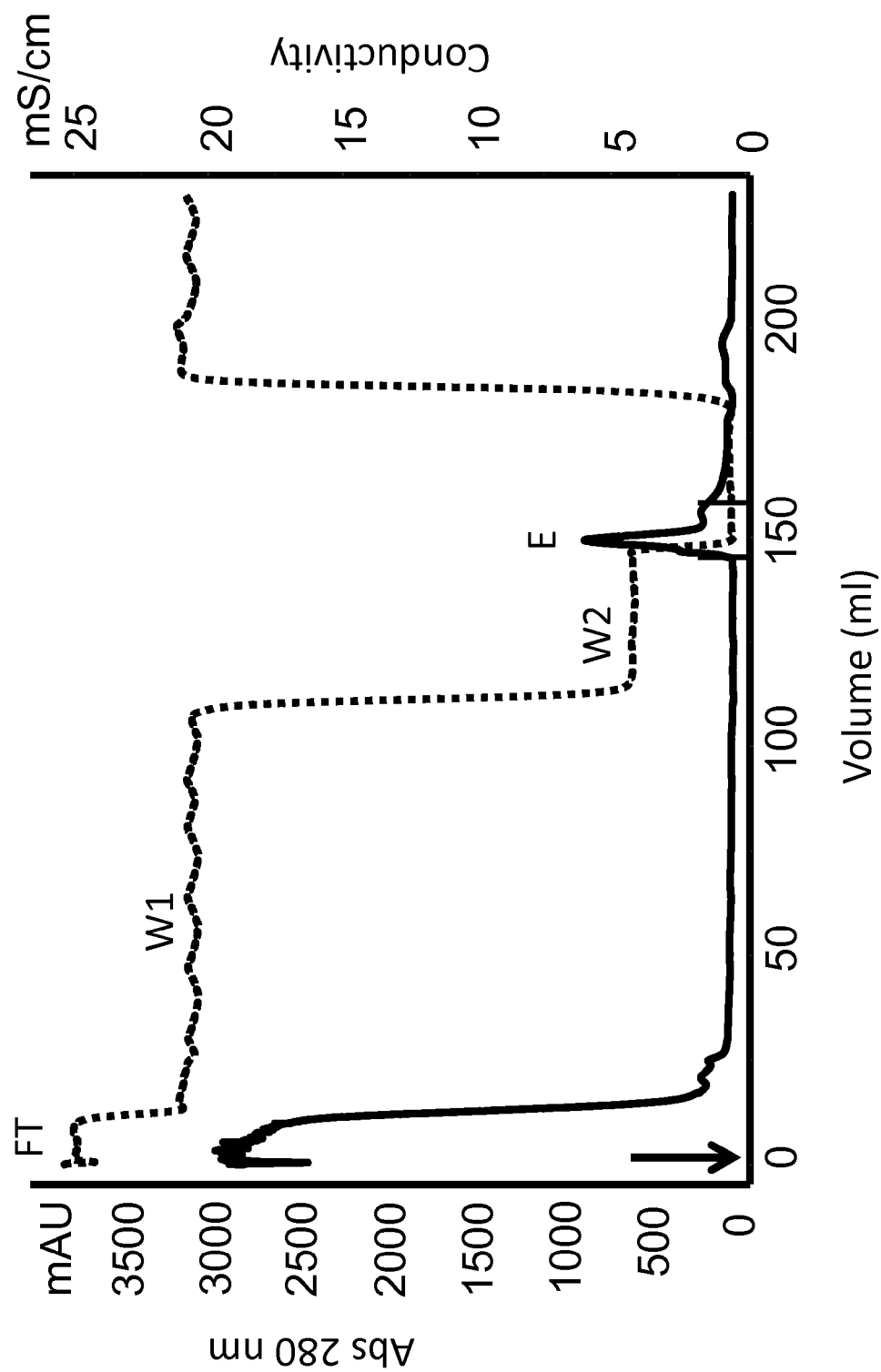
FIG. 13A shows a chromatogram from affinity purification of Protein 2, comprising ABD035 (SEQ ID NO:159) fused at its N-terminus to a peptide hormone, on anti-ABD agarose performed as described in Example 12. The sample injection point is indicated by an arrow. The absorbance signal at 280 nm (solid line) and the conductivity (dotted line) are shown. FT, W and E refer to the flow-through fraction, wash fractions and eluted fraction, respectively. First wash step, W1, was performed with 8 CV of TST and second wash step, W2, with 3 CV of 5 mM NH$_4$Ac, pH 5.5.
Figure 13B:
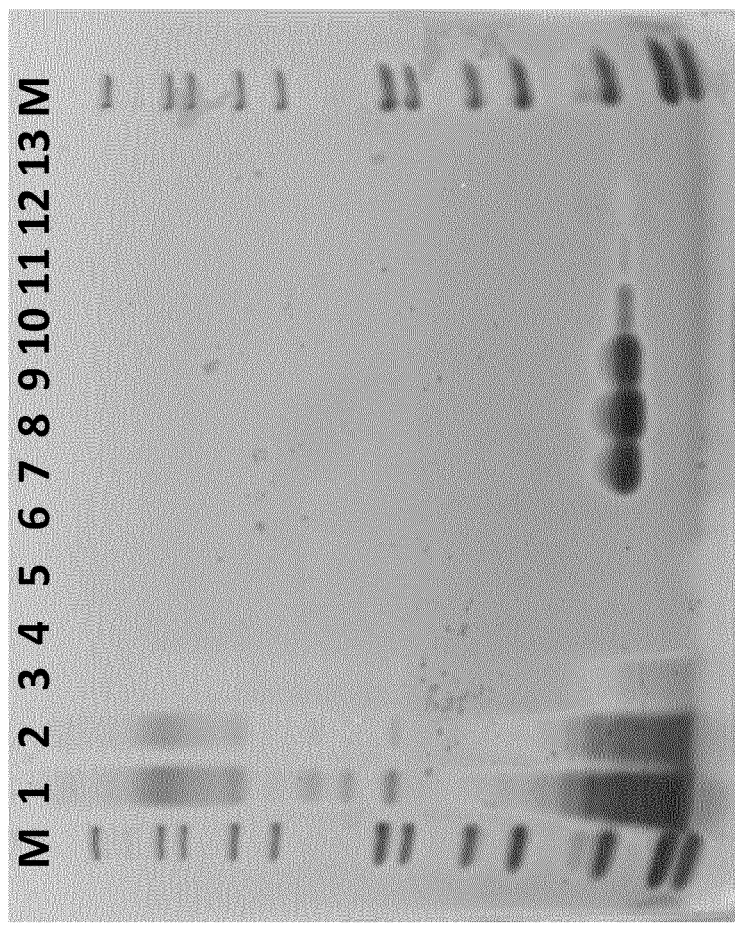
FIG. 13B shows the result of SDS-PAGE analysis of selected fractions from the purification described in Example 12. Lane 1: Protein sample loaded on the anti-ABD agarose column. Lane 2: FT. Lanes 4-6: Wash fractions. Lanes 7-13: Eluted protein fractions within the double peak marked in FIG. 13A. Fractions corresponding to the first peak within the double peak were loaded in lanes 7-10. Lanes marked with "M" were loaded with a protein molecular weight marker (Mw: 200, 116.3, 97.4, 66.3, 55.4, 36.5, 31, 21.5, 14.4, 6, 3.5, 2.5 kDa).

The chromatogram from purification of Protein 2 on the anti-ABD agarose resin is presented in FIG. 13A and the SDS-PAGE analysis of selected fractions is shown in FIG. 13B. The elution peak from the anti-ABD agarose column contained 3-5 mg of Protein 2, corresponding to a yield of approximately 75% (estimated from a Western blot). The correct mass of the eluted Protein 2 was verified by HPLC-MS analysis. The purity was estimated to be higher than 98% as judged from SDS-PAGE analysis followed by Simply Blue staining. No contaminating media proteins could be detected in the elution fractions (lanes 7-13, FIG. 13B). It is recognized that Protein 2 runs smaller on SDS-PAGE gels as indicated by the molecular weight standards included on the gels.

Itemized Listing of Embodiments

1. Method of separation of at least one ABD-containing molecule present in a liquid from other constituents in the liquid, comprising a step of affinity separation, in which step is used, as affinity ligand, an ABD binding polypeptide comprising an ABD binding motif BM, which motif consists of an amino acid sequence selected from:

i)
(SEQ ID NO: 166)
$EX_2X_3X_4AX_6X_7EIX_{10}X_{11}LPNLX_{16}X_{17}X_{18}QX_{20}X_{21}AFIX_{25}X_{26}LX_{28}D$ wherein, independently from each other,
 $X_2$ is selected from F, I and L;
 $X_3$ is selected from H, K, N, Q, R, S, T and V;
 $X_4$ is selected from A, D, F, G, H, I, K, L, M, N, Q, R, S, T, V, W and Y;
 $X_6$ is selected from F, I, L and Y;
 $X_7$ is selected from A, H, I, K, L, N, Q, R, S, T and V;
 $X_{10}$ is selected from G, H, K, N, Q, R and S;
 $X_{11}$ is selected from A, D, F, G, I, K, L, N, Q, R, S, T, V and Y;
 $X_{16}$ is selected from N and T;
 $X_{17}$ is selected from F, H, L, S and T;
 $X_{18}$ is selected from D, E, H, I, K, L, M, N, Q, R, S, T and V;
 $X_{20}$ is selected from H, K and R;
 $X_{21}$ is selected from I, L and V;
 $X_{25}$ is selected from F, I, L, V and Y;
 $X_{26}$ is selected from K and S;
 $X_{28}$ is selected from D and E;
and
ii) an amino acid sequence which has at least 89% identity to the sequence defined in i).

2. Method according to item 1, comprising the steps:
 a) applying the liquid to an affinity matrix comprising said ABD binding polypeptide under conditions that are conducive to binding of an ABD-containing molecule to the affinity matrix;
 b) washing the affinity matrix for removal of substances not bound thereto; and
 c) eluting any bound ABD-containing molecule from the affinity matrix, thus obtaining an ABD-containing molecule fraction with an enriched content of ABD-containing molecule; and
 d) recovering said ABD-containing molecule fraction.

3. Method according to item 1, comprising the steps:
 a) applying the liquid to an affinity matrix comprising said ABD binding polypeptide under conditions that are conducive to binding of an ABD-containing molecule to the affinity matrix;
 b) washing the affinity matrix for recovery of substances not bound thereto, thus obtaining a depleted fraction with a substantially reduced ABD-containing molecule content; and
 c) recovering said depleted fraction.

4. Method according to item 1, comprising the steps:
 a) applying the liquid to an affinity matrix comprising said ABD binding polypeptide under conditions that are conducive to binding of an ABD-containing molecule to the affinity matrix;
 b) washing the affinity matrix for recovery of substances not bound thereto, thus obtaining a depleted fraction with a substantially reduced ABD-containing molecule content; and
 c) eluting the bound ABD-containing molecule from the affinity matrix, thus obtaining an ABD-containing molecule fraction with an ABD-containing molecule content; and
 d) recovering said ABD-containing molecule fraction and said depleted fraction.

5. Method according to any preceding item, which is carried out in a setup selected from batch, column, expanded bed and mixtures thereof.

6. Method according to item 5, which is carried out in a column setup.

7. Method according to item 5, which is carried out in a batch setup.

8. Method according to any preceding item, wherein $X_2$ in sequence i) is selected from F and L.

9. Method according to item 8, wherein $X_2$ in sequence i) is F.

10. Method according to item 8, wherein $X_2$ in sequence i) is L.

11. Method according to any preceding item, wherein $X_3$ in sequence i) is selected from H, K, R, T and V.

12. Method according to item 11, wherein $X_3$ in sequence i) is selected from H, K, R and V.

13. Method according to item 12, wherein $X_3$ in sequence i) is selected from K and R.

14. Method according to item 13, wherein $X_3$ in sequence i) is K.

15. Method according to item 13, wherein $X_3$ in sequence i) is R.

16. Method according to any preceding item, wherein $X_4$ in sequence i) is selected from A, H, I, L, N, V and W.

17. Method according to item 16, wherein $X_4$ in sequence i) is selected from H, L, N and V.

18. Method according to item 17, wherein $X_4$ in sequence i) is V.

19. Method according to any preceding item, wherein $X_6$ in sequence i) is selected from F and L.

20. Method according to item 19, wherein $X_6$ in sequence i) is F.

21. Method according to item 19, wherein $X_6$ in sequence i) is L.

22. Method according to any preceding item, wherein $X_7$ in sequence i) is selected from K, L, N, Q, R and S.

23. Method according to item 22, wherein $X_7$ in sequence i) is selected from K, N, Q, R and S.

24. Method according to item 23, wherein $X_7$ in sequence i) is selected from K, Q, R and S.

25. Method according to item 24, wherein $X_7$ in sequence i) is selected from K and R.

26. Method according to item 25, wherein $X_7$ in sequence i) is K.

27. Method according to item 25, wherein $X_7$ in sequence i) is R.

28. Method according to any preceding item, wherein $X_{10}$ in sequence i) is selected from H, K, N, and R.

29. Method according to item 28, wherein $X_{10}$ in sequence i) is selected from H, K and N.

30. Method according to item 28, wherein $X_{10}$ in sequence i) is selected from K, N and R.

31. Method according to item 29 or 30, wherein $X_{10}$ in sequence i) is N.

32. Method according to item 30, wherein $X_{10}$ in sequence i) is selected from K and R.

33. Method according to item 32, wherein $X_{10}$ in sequence i) is K.

34. Method according to item 32, wherein $X_{10}$ in sequence i) is R.

35. Method according to any one of the preceding items, wherein $X_{11}$ in sequence i) is selected from A, F, L, R, T and Y.

36. Method according to item 35, wherein $X_{11}$ in sequence i) is selected from A, F, T and Y.

37. Method according to item 36, wherein $X_{11}$ in sequence i) is T.

38. Method according to any preceding item, wherein $X_{16}$ in sequence i) is T.

39. Method according to any preceding item, wherein $X_{17}$ in sequence i) is selected from F, H and L.

40. Method according to item 39, wherein $X_{17}$ in sequence i) is selected from F and H.

41. Method according to item 39, wherein $X_{17}$ in sequence i) is selected from H and L.

42. Method according to item 40, wherein $X_{17}$ in sequence i) is F.

43. Method according to item 40 or 41, wherein $X_{17}$ in sequence i) is H.

44. Method according to item 41, wherein $X_{17}$ in sequence i) is L.

45. Method according to any preceding item, wherein $X_{18}$ in sequence i) is selected from D, H, I, K and Q.

46. Method according to item 45, wherein $X_{18}$ in sequence i) is selected from D, H and Q.

47. Method according to item 46, wherein $X_{18}$ in sequence i) is selected from H and Q.

48. Method according to item 47, wherein $X_{18}$ in sequence i) is H.

49. Method according to item 47, wherein $X_{18}$ in sequence i) is Q.

50. Method according to any preceding item, wherein $X_{20}$ in sequence i) is selected from H and R.

51. Method according to any one of items 1-49, wherein $X_{20}$ in sequence i) is selected from K and R.

52. Method according to item 50 or 51, wherein $X_{20}$ in sequence i) is R.

53. Method according to item 51, wherein $X_{20}$ in sequence i) is K.

54. Method according to any preceding item, wherein $X_{21}$ in sequence i) is selected from I and L.

55. Method according to item 54, wherein $X_{21}$ in sequence i) is I.

56. Method according to item 54, wherein $X_{21}$ in sequence i) is L.

57. Method according to any preceding item, wherein $X_{25}$ in sequence i) is selected from I, L and V.

58. Method according to item 57, wherein $X_{25}$ in sequence i) is selected from V and I.

59. Method according to item 58, wherein $X_{25}$ in sequence i) is I.

60. Method according to item 58, wherein $X_{25}$ in sequence i) is V.

61. Method according to any preceding item, wherein $X_{26}$ in sequence i) is K.

62. Method according to any preceding item, wherein $X_{28}$ in sequence i) is D.

63. Method according to any preceding item, wherein sequence i) fulfills at least four of the eight conditions I-VIII:
I. $X_2$ is F or L;
II. $X_6$ is F or L;
III. $X_{16}$ is T;
IV. $X_{20}$ is H or R;
V. $X_{21}$ is I or L;
VI. $X_{25}$ is I or V;
VII. $X_{26}$ is K; and
VIII. $X_{28}$ is D.

64. Method according to item 63, wherein sequence i) fulfills at least five of the eight conditions I-VIII.

65. Method according to item 64, wherein sequence i) fulfills at least six of the eight conditions I-VIII.

66. Method according to item 65, wherein sequence i) fulfills at least seven of the eight conditions I-VIII.

67. Method according to item 66, wherein sequence i) fulfills all of the eight conditions I-VIII.

68. Method according to any preceding item, wherein sequence i) is selected from SEQ ID NO:1-52.

69. Method according to item 68, wherein sequence i) is selected from SEQ ID NO:1-7.

70. Method according to item 69, wherein sequence i) is selected from SEQ ID NO:1-4.

71. Method according to item 70, wherein sequence i) is SEQ ID NO:1.

72. Method according to any preceding item, wherein said ABD binding motif forms part of a three-helix bundle protein domain.

73. Method according to item 72, wherein said ABD binding motif essentially forms part of two helices with an interconnecting loop, within said three-helix bundle protein domain.

74. Method according to any one of items 72-73, wherein said three-helix bundle protein domain is selected from bacterial receptor domains.

75. Method according to item 74, wherein said three-helix bundle protein domain is selected from domains of protein A from *Staphylococcus aureus* or derivatives thereof.

76. Method according to any preceding item, in which said ABD binding polypeptide comprises an amino acid sequence selected from:

```
iii)                                    (SEQ ID NO: 167)
K-[BM]-DPSQS XaXbLLXc EAKKL NDXdQ;
``` wherein
[BM] is an ABD binding motif as defined in any one of items 1 and 8-71,
$X_a$ is selected from A and S;
$X_b$ is selected from N and E;
$X_c$ is selected from A, S and C;
$X_d$ is selected from A and S;
and
iv) an amino acid sequence which has at least 81% identity to a sequence defined by iii).

77. Method according to item 76, wherein $X_a$ in sequence iii) is A.

78. Method according to item 76, wherein $X_a$ in sequence iii) is S.

79. Method according to any one of items 76-78, wherein $X_b$ in sequence iii) is N.

80. Method according to any one of items 76-78, wherein $X_b$ in sequence iii) is E.

81. Method according to any one of items 76-80, wherein $X_c$ in sequence iii) is A.

82. Method according to any one of items 76-80, wherein $X_c$ in sequence iii) is S.

83. Method according to any one of items 76-80, wherein $X_c$ in sequence iii) is C.

84. Method according to any one of items 76-83, wherein $X_d$ in sequence iii) is A.

85. Method according to any one of items 76-83, wherein $X_d$ in sequence iii) is S.

86. Method according to item 76, wherein, in sequence iii), $X_a$ is A; $X_b$ is N; $X_c$ is A and $X_d$ is A.

87. Method according to item 76, wherein, in sequence iii), $X_a$ is A; $X_b$ is N; $X_c$ is C and $X_d$ is A.

88. Method according to item 76, wherein, in sequence iii), $X_a$ is S; $X_b$ is E; $X_c$ is S and $X_d$ is S.

89. Method according to item 76, wherein, in sequence iii), $X_a$ is S; $X_b$ is E; $X_c$ is C and $X_d$ is S.

90. Method according to item 76, wherein, in sequence iii), $X_a$ is S; $X_b$ is E; $X_c$ is C and $X_d$ is A.

91. Method according to item 76, wherein, in sequence iii), $X_a$ is S; $X_b$ is E; $X_c$ is A and $X_d$ is A.

92. Method according to item 91, wherein sequence iii) is selected from any one of SEQ ID NO:53-104.

93. Method according to item 92, wherein sequence iii) is selected from any one of SEQ ID NO:53-59.

94. Method according to item 93, wherein sequence iii) is selected from any one of SEQ ID NO:53-56.

95. Method according to item 94, wherein sequence iii) is SEQ ID NO:53.

96. Method according to any one of items 1-76, in which said ABD binding polypeptide comprises an amino acid sequence selected from:

```
v)                                      (SEQ ID NO: 168)
YAK-[BM]-DPSQS SELLXc EAKKL NDSQA P;
``` wherein [BM] is an ABD binding motif as defined in any one of items 1 and 8-71 and $X_c$ is selected from S and C; and
vi) an amino acid sequence which has at least 83% identity to a sequence defined by v).

97. Method according to any one of items 1-76, in which said ABD binding polypeptide comprises an amino acid sequence selected from:

```
vii)                                    (SEQ ID NO: 169)
YAK-[BM]-DPSQS SELLXc EAKKL NDAQA P;
``` wherein [BM] is an ABD binding motif as defined in any one of items 1 and 8-71 and $X_c$ is selected from A and C; and
viii) an amino acid sequence which has at least 83% identity to a sequence defined by vii).

98. Method according to any one of items 1-76, in which said ABD binding polypeptide comprises an amino acid sequence selected from:

```
ix)                                     (SEQ ID NO: 170)
FNK-[BM]-DPSQS ANLLXc EAKKL NDAQA P;
``` wherein [BM] is an ABD binding motif as defined in any one of items 1 and 8-71 and $X_c$ is selected from A and C; and
x) an amino acid sequence which has at least 83% identity to a sequence defined by ix).

99. Method according to item 75, in which said ABD binding polypeptide comprises an amino acid sequence selected from:

```
                                        (SEQ ID NO: 171)
ADNNFNK-[BM]-DPSQSANLLSEAKKLNESQAPK;

(SEQ ID NO: 172)
ADNKFNK-[BM]-DPSQSANLLAEAKKLNDAQAPK;

(SEQ ID NO: 173)
ADNKFNK-[BM]-DPSVSKEILAEAKKLNDAQAPK;

(SEQ ID NO: 174)
ADAQQNNFNK-[BM]-DPSQSTNVLGEAKKLNESQAPK;

(SEQ ID NO: 175)
AQHDE-[BM]-DPSQSANVLGEAQKLNDSQAPK;

(SEQ ID NO: 176)
VDNKFNK-[BM]-DPSQSANLLAEAKKLNDAQAPK;

(SEQ ID NO: 177)
AEAKYAK-[BM]-DPSESSELLSEAKKLNKSQAPK;

(SEQ ID NO: 178)
VDAKYAK-[BM]-DPSQSSELLAEAKKLNDAQAPK;

(SEQ ID NO: 179)
VDAKYAK-[BM]-DPSQSSELLAEAKKLNDSQAPK;
```

```
                                                         (SEQ ID NO: 180)
AEAKYAK-[BM]-DPSQSSELLSEAKKLNDSQAPK;

(SEQ ID NO: 181)
VDAKYAK-[BM]-DPSQSSELLSEAKKLNDSQAPK;

(SEQ ID NO: 182)
VDAKYAK-[BM]-DPSQSSELLAEAKKLNKAQAPK;
and (SEQ ID NO: 183)
AEAKYAK-[BM]-DPSQSSELLAEAKKLNKAQAPK;
``` wherein [BM] is an ABD binding motif as defined in any one of items 1 and 8-71.

100. Method according to according to any preceding item, which comprises an amino acid sequence selected from:

```
xi)
                                                         (SEQ ID NO: 184)
VDAKYAK-[BM]-DPSQSSELLAEAKKLNDAQAPK;
``` wherein [BM] is an ABD binding motif as defined in any one of items 1 and 8-71; and xii) an amino acid sequence which has at least 84% identity to the sequence defined in xi).

101. Method according to item 100, in which sequence xi) is selected from SEQ ID NO:105-156.

102. Method according to item 101, in which sequence xi) is selected from SEQ ID NO 105-111.

103. Method according to item 102, in which sequence xi) is selected from SEQ ID NO:105-108.

104. Method according to item 103, in which sequence xi) is SEQ ID NO:105.

105. Method according to any preceding item, in which said ABD binding polypeptide is present in multimeric form, comprising at least two ABD binding polypeptide monomer units, whose amino acid sequences may be the same or different.

106. Method according to item 105, wherein said ABD binding polypeptide monomer units are covalently coupled together.

107. Method according to item 105, wherein the ABD binding polypeptide monomer units are expressed as a fusion protein.

108. Method according to any preceding item, in which said ABD binding polypeptide further comprises a cysteine residue at the C terminal end of the polypeptide, for example at the C terminus.

The invention claimed is:

1. A method of separation of at least one ABD-containing molecule present in a liquid from other constituents in the liquid, comprising a step of affinity separation, in which step is used, as affinity ligand, an ABD binding polypeptide comprising an ABD binding motif BM, which motif consists of an amino acid sequence selected from:

i)
(SEQ ID NO: 166)
$EX_2X_3X_4AX_6X_7EIX_{10}X_{11}LPNLX_{16}X_{17}X_{18}QX_{20}X_{21}AFIX_{25}X_{26}LX_{28}D$ wherein, independently from each other,
$X_2$ is selected from F, I and L;
$X_3$ is selected from H, K, N, Q, R, S, T and V;
$X_4$ is selected from A, D, F, G, H, I, K, L, M, N, Q, R, S, T, V, W and Y;
$X_6$ is selected from F, I, L and Y;
$X_7$ is selected from A, H, I, K, L, N, Q, R, S, T and V;
$X_{10}$ is selected from G, H, K, N, Q, R and S;
$X_{11}$ is selected from A, D, F, G, I, K, L, N, Q, R, S, T, V and Y;
$X_{16}$ is selected from N and T;
$X_{17}$ is selected from F, H, L, S and T;
$X_{18}$ is selected from D, E, H, I, K, L, M, N, Q, R, S, T and V;
$X_{20}$ is selected from H, K and R;
$X_{21}$ is selected from I, L and V;
$X_{25}$ is selected from F, I, L, V and Y;
$X_{26}$ is selected from K and S;

$X_{28}$ is selected from D and E; and ii) an amino acid sequence which has at least 89% identity to the sequence defined in i).

2. The method according to claim 1, comprising the steps of:
   a) applying the liquid to an affinity matrix comprising said ABD binding polypeptide under conditions that are conducive to binding of an ABD-containing molecule to the affinity matrix;
   b) washing the affinity matrix for removal of substances not bound thereto; and
   c) eluting any bound ABD-containing molecule from the affinity matrix, thus obtaining an ABD-containing molecule fraction with an enriched content of ABD-containing molecule; and
   d) recovering said ABD-containing molecule fraction.

3. The method according to claim 1, comprising the steps of:
   a) applying the liquid to an affinity matrix comprising said ABD binding polypeptide under conditions that are conducive to binding of an ABD-containing molecule to the affinity matrix;
   b) washing the affinity matrix for recovery of substances not bound thereto, thus obtaining a depleted fraction with a substantially reduced ABD-containing molecule content; and
   c) recovering said depleted fraction.

4. The method according to claim 1, comprising the steps:
   a) applying the liquid to an affinity matrix comprising said ABD binding polypeptide under conditions that are conducive to binding of an ABD-containing molecule to the affinity matrix;
   b) washing the affinity matrix for recovery of substances not bound thereto, thus obtaining a depleted fraction with a substantially reduced ABD-containing molecule content; and
   c) eluting the bound ABD-containing molecule from the affinity matrix, thus obtaining an ABD-containing molecule fraction with an ABD-containing molecule content; and
   d) recovering said ABD-containing molecule fraction and said depleted fraction.

5. The method according to claim 1, wherein sequence i) fulfills at least four of the eight conditions I-VIII:
   I. $X_2$ is F or L;
   II. $X_6$ is F or L;
   III. $X_{16}$ is T;
   IV. $X_{20}$ is H or R;
   V. $X_{21}$ is I or L;
   VI. $X_{25}$ is I or V;
   VII. $X_{26}$ is K; and
   VIII. $X_{28}$ is D.

6. The method according to claim 1, wherein sequence i) is selected from SEQ ID NO:1-52.

7. The method according to claim 6, wherein sequence i) is selected from SEQ ID NO:1-7.

8. The method according to claim 1, wherein said ABD binding motif forms part of a three-helix bundle protein domain selected from domains of protein A from *Staphylococcus aureus* or derivatives thereof.

9. The method according to claim 1, in which said ABD binding polypeptide comprises an amino acid sequence selected from:

iii)                                              (SEQ ID NO: 167)
K-[BM]-DPSQS X$_a$X$_b$LLX$_c$ EAKKL NDX$_d$Q;

wherein
   [BM] is an ABD binding motif as defined in claim 1;
   $X_a$ is selected from A and S;
   $X_b$ is selected from N and E;
   $X_c$ is selected from A, S and C;
   $X_d$ is selected from A and S; and
   iv) an amino acid sequence which has at least 81% identity to a sequence defined by iii).

10. The method according to claim 9, wherein sequence iii) is selected from any one of SEQ ID NO:53-104.

11. The method according to claim 10, wherein sequence iii) is selected from any one of SEQ ID NO:53-59.

12. The method according to according to claim 1, which comprises an amino acid sequence selected from:

xi)                                              (SEQ ID NO: 184)
VDAKYAK-[BM]-DPSQSSELLAEAKKLNDAQAPK;

wherein [BM] is an ABD binding motif as defined in claim 1; and
   xii) an amino acid sequence which has at least 84% identity to the sequence defined in xi).

13. The method according to claim 12, in which sequence xi) is selected from SEQ ID NO:105-156.

14. The method according to claim 13, in which sequence xi) is selected from SEQ ID NO 105-111.

* * * * *